(12) United States Patent
Yamashita et al.

(10) Patent No.: US 7,605,382 B2
(45) Date of Patent: Oct. 20, 2009

(54) ION IMPLANTER

(75) Inventors: Takatoshi Yamashita, Kyoto (JP); Hideki Fujita, Kyoto (JP)

(73) Assignee: Nissin Ion Equipment Co., Ltd., Kyoto (JP)

( * ) Notice: Subject to any disclaimer, the term of this patent is extended or adjusted under 35 U.S.C. 154(b) by 160 days.

(21) Appl. No.: 11/927,839

(22) Filed: Oct. 30, 2007

(65) Prior Publication Data

US 2008/0135753 A1   Jun. 12, 2008

Related U.S. Application Data

(60) Provisional application No. 60/873,981, filed on Dec. 11, 2006.

(30) Foreign Application Priority Data

Oct. 31, 2006   (JP) .................... P.2006-295859

(51) Int. Cl.
- H01J 37/317 (2006.01)
- H01J 37/256 (2006.01)
- G05F 3/02 (2006.01)

(52) U.S. Cl. .............. 250/492.21; 250/492.2; 250/492.3; 250/423 R; 250/426; 250/427

(58) Field of Classification Search ........... 250/492.21, 250/492.2, 492.3, 423 R, 426, 427; 315/111.21, 315/111.91
See application file for complete search history.

(56) References Cited

U.S. PATENT DOCUMENTS

| | | | |
|---|---|---|---|
| 7,491,953 B2* | 2/2009 | Horsky et al. | 250/492.21 |
| 2006/0097193 A1* | 5/2006 | Horsky et al. | 250/492.21 |
| 2009/0090872 A1* | 4/2009 | Horsky et al. | 250/427 |

FOREIGN PATENT DOCUMENTS

| | | |
|---|---|---|
| JP | 2000-315473 | 11/2000 |
| JP | 2005-38689 | 2/2005 |

* cited by examiner

*Primary Examiner*—Nikita Wells
(74) *Attorney, Agent, or Firm*—Finnegan, Henderson, Farabow, Garrett & Dunner, L.L.P.

(57) ABSTRACT

The ion implanter has: an ion source which generates an ion beam; electron beam sources which emit an electron beam to be scanned in the Y direction in the ion source; a power source for the sources; an ion beam monitor which, in the vicinity of an implanting position, measures a Y-direction ion beam current density distribution of the ion beam; and a controlling device. The controlling device has a function of homogenizing the Y-direction ion beam current density distribution measured by the monitor, by, while controlling the power sources on the basis of measurement data of the monitor, increasing a scanning speed of the electron beam in a position corresponding to a monitor point where an ion beam current density measured by the monitor is large; and decreasing the scanning speed of the electron beam in a position corresponding to a monitor point where the measured ion beam current density is small.

15 Claims, 43 Drawing Sheets

FIG. 23
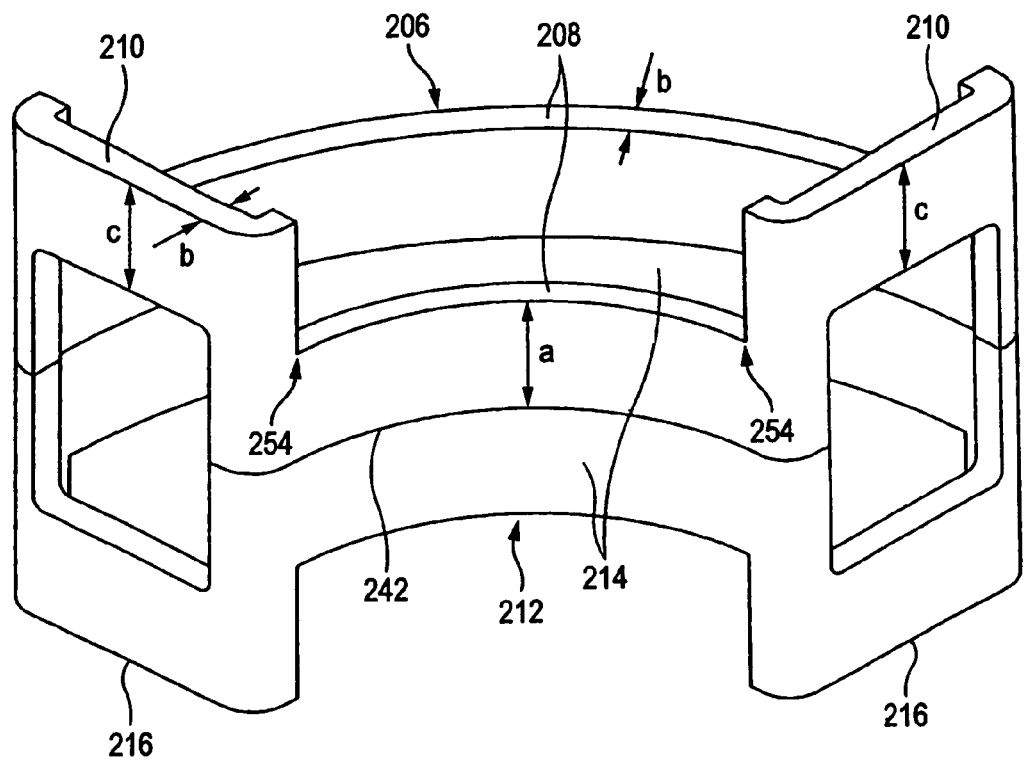
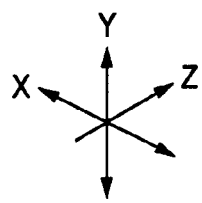

FIG. 37
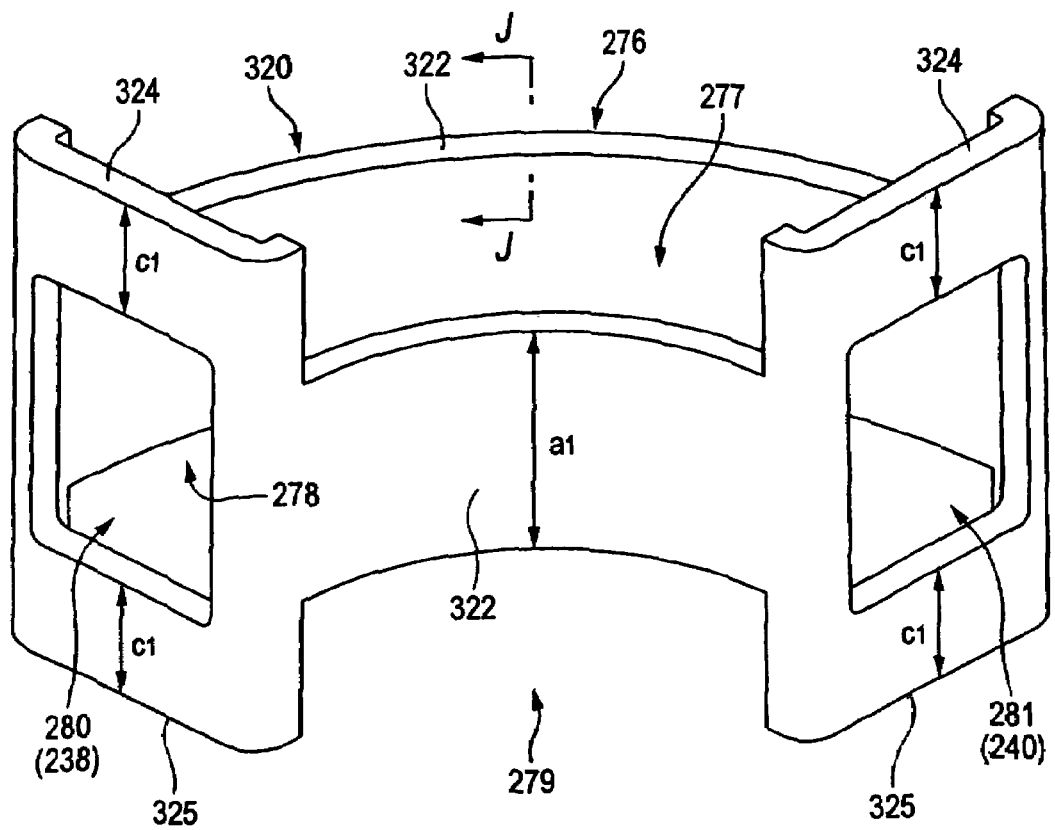
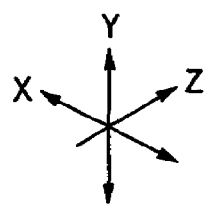

ION IMPLANTER

CROSS REFERENCE TO RELATED APPLICATIONS

This application claims the priority of Japanese Patent Application No. 2006-295859, filed Oct. 31, 2006, and claims the benefit of U.S. Provisional Application No. 60/873,981, filed Dec. 11, 2006, the contents of both of which are incorporated herein by reference.

TECHNICAL FIELD

The present disclosure relates to an ion implanter in which ion implantation is performed on a substrate by combinedly using incidence of a ribbon-like ion beam on the substrate, and movement of the substrate in a direction intersecting the principal face of the ion beam.

RELATED ART

In an ion implanter of this kind, in order to enhance the homogenization of ion implantation on a substrate, it is important to improve the homogenization of the ion beam current density distribution in the longitudinal direction (in the specification, the Y direction) of a ribbon-like (this is called also a sheet-like or a strip-like, the same shall apply hereinafter) ion beam.

As a technique for improving the homogenization of the ion beam current density distribution in the longitudinal direction of a ribbon-like ion beam, for example, Patent Reference 1 discloses a technique in which filament currents of an ion source having plural filaments are controlled to improve the homogenization of the ion beam current density distribution in the vicinity of an implanting position where an ion beam is incident on a substrate.

Patent Reference 2 discloses a technique in which an electron beam that is one-dimensionally scanned is incident into a plasma vessel of an ion source, and a gas is ionized by the electron beam to produce a plasma, thereby improving the ion beam current density distribution of an ion beam extracted an ion source.

[Patent Reference 1] JP-A-2000-315473 (Paragraphs 0012 to 0015, FIG. 1)

[Patent Reference 2] JP-A-2005-38689 (Paragraphs 0006 to 0008, FIG. 1)

In the technique disclosed by Patent Reference 1, even when the plural filaments are arranged in the longitudinal direction of the ion beam, spaces unavoidably exist between the filaments, and hence the plasma density and therefore the ion beam current density are inevitably lowered. Therefore, there is a limit to the enhancement of the homogenization of the ion beam current density distribution.

In the technique disclosed by Patent Reference 2, even when the homogenization of the ion beam extracted an ion source can be improved, there is case where the homogenization is impaired during traveling of the ion beam. Consequently, there is no guarantee that the homogenization of the ion beam current density distribution in the implanting position is excellent.

SUMMARY

Exemplary embodiments of the present invention provide an ion implanter in which the homogenization of the ion beam current density distribution in the longitudinal direction (Y direction) in the implanting position on a substrate can be improved.

According to a first aspect of the present invention, the first ion implanter of the present invention is an ion implanter in which a traveling direction of an ion beam is set as a Z direction, two directions which are substantially orthogonal to each other in a plane that is substantially orthogonal to the Z direction are set as X and Y directions, respectively, and a ribbon-like ion beam in which a dimension in the Y direction is larger than a dimension in the X direction is transported to irradiate a substrate, thereby performing ion implantation. The ion implanter comprises:

an ion source that has one or more filaments for generating an arc discharge in a plasma vessel into which a gas is introduced, and that generates the ribbon-like ion beam in which a Y-direction dimension is larger than a Y-direction dimension of the substrate;

a substrate driving device which, in an implanting position where the ion beam is caused to be incident on the substrate, moves the substrate in a direction intersecting with a principal face of the ion beam;

one or more electron beam sources which generate an electron beam, which emit the electron beam into the plasma vessel of the ion source to ionize the gas, thereby producing a plasma, and which scans the electron beam in the Y direction in the plasma vessel;

one or more electron-beam power sources which supply an extraction voltage for controlling a generation quantity of the electron beam, and a scan voltage for the scan to the electron beam sources;

an ion beam monitor which, in the implanting position or a vicinity of the position, measures a Y-direction ion beam current density distribution of the ion beam at plural monitor points in the Y direction; and a controlling device having a function of homogenizing the Y-direction ion beam current density distribution measured by the ion beam monitor, by, while controlling the electron-beam power sources on the basis of measurement data of the ion beam monitor to maintain the quantity of the electron beam generated from the electron beam sources to a substantially constant value, performing at least one of: a relative increase of a scanning speed of the electron beam in a position in the ion source corresponding to a monitor point where an ion beam current density measured by the ion beam monitor is relatively large; and a relative decrease of the scanning speed of the electron beam in a position in the ion source corresponding to a monitor point where the ion beam current density measured by the ion beam monitor is relatively small.

In the first ion implanter, the Y-direction ion beam current density distribution of the ion beam in the implanting position or the vicinity of the position is measured by the ion beam monitor. Then, the controlling device controls the electron-beam power sources on the basis of measurement data of the ion beam monitor, and controls the scanning speed of the electron beam in the plasma vessel of the ion source to control the density of the plasma produced by the electron beam. Specifically, while maintaining the quantity of the electron beam generated from the electron beam sources to a substantially constant value, at least one of: a relative increase of the scanning speed of the electron beam in a position in the ion source corresponding to a monitor point where an ion beam current density measured by the ion beam monitor is relatively large; and a relative decrease of the scanning speed of the electron beam in a position in the ion source corresponding to a monitor point where the ion beam current density measured by the ion beam monitor is relatively small is performed, thereby performing the control of homogenizing the Y-direction ion beam current density distribution measured by the ion beam monitor. According to the configuration, the homogenization of the ion beam current density distribution in the Y direction in the implanting position can be improved.

According to second and third aspects of the present invention, (a) the controlling device may have functions of: supplying a scan signal which is an original of the scan voltage to be supplied from the electron-beam power source to the electron beam source, to the electron-beam power source; calculating an average value of ion beam current densities in a Y-direction distribution measured by the ion beam monitor; uniformly controlling filament currents to be flown through the filaments of the ion source so that the calculate average value is substantially equal to a preset predetermined ion beam current density; calculating an error of the Y-direction distribution which is a difference between the ion beam current density in a Y-direction distribution measured by the ion beam monitor, and the preset ion beam current density; determining a monitor point where the calculated error is larger than a predetermined allowable error, and a sign of an error at the monitor point; determining a scan voltage corresponding to the determined monitor point; based on the determined sign of the error, increasing the scanning speed of the electron beam at a scan voltage corresponding to a monitor point where the measured ion beam current density is larger, in proportion to a degree of the error, and decreasing the scanning speed of the electron beam at a scan voltage corresponding to a monitor point where the measured ion beam current density is smaller, in proportion to a degree of the error, thereby shaping a waveform of the scan signal so that the error is equal to or less than the allowable error at substantially all monitor points on which the ion beam impinges; and storing data of the shaped scan signal, and data of the filament currents, and (b) the electron-beam power source may have an amplifier which amplifies the scan signal supplied from the controlling device, to produce the scan voltage.

In the specification, "substantially all monitor points" means that all monitor points are preferable, but several unimportant monitor points may be excluded.

According to a fourth aspect of the present invention, the second ion implanter of the present invention is an ion implanter in which a traveling direction of an ion beam is set as a Z direction, two directions which are substantially orthogonal to each other in a plane that is substantially orthogonal to the Z direction are set as X and Y directions, respectively, and a ribbon-like ion beam in which a dimension in the Y direction is larger than a dimension in the X direction is transported to irradiate a substrate, thereby performing ion implantation. The ion implanter comprises: an ion source that has one or more filaments for generating an arc discharge in a plasma vessel into which a gas is introduced, and that generates the ribbon-like ion beam in which a Y-direction dimension is larger than a Y-direction dimension of the substrate; a substrate driving device which, in an implanting position where the ion beam is caused to be incident on the substrate, moves the substrate in a direction intersecting with a principal face of the ion beam; one or more electron beam sources which generate an electron beam, and emit the electron beam into the plasma vessel of the ion source to ionize the gas, thereby producing a plasma, and which scans the electron beam in the Y direction in the plasma vessel; one or more electron-beam power sources which supply an extraction voltage for controlling a generation quantity of the electron beam, and a scan voltage for the scan to the electron beam sources; an ion beam monitor which, in the implanting position or a vicinity of the position, measures a Y-direction ion beam current density distribution of the ion beam at plural monitor points in the Y direction; and a controlling device having a function of homogenizing the Y-direction ion beam current density distribution measured by the ion beam monitor, by, while controlling the electron-beam power sources on the basis of measurement data of the ion beam monitor to maintain a scanning speed of the electron beam generated by the electron beam source to a substantially constant value, performing at least one of: a relative decrease of the generation quantity of the electron beam in a position in the ion source corresponding to a monitor point where an ion beam current density measured by the ion beam monitor is relatively large; and a relative increase of the generation quantity of the electron beam in a position in the ion source corresponding to a monitor point where the ion beam current density measured by the ion beam monitor is relatively small.

In the second ion implanter, the Y-direction ion beam current density distribution of the ion beam in the implanting position or the vicinity of the position is measured by the ion beam monitor. Then, the controlling device controls the electron-beam power sources on the basis of measurement data of the ion beam monitor, and controls the generation quantity of the electron beam from the electron beam source, thereby controlling the density of the plasma produced by the electron beam in the plasma vessel. Specifically, while maintaining the y-direction scanning speed of the electron beam generated by the electron beam source to a substantially constant value, at least one of: a relative decrease of the generation quantity of the electron beam in a position in the ion source corresponding to a monitor point where an ion beam current density measured by the ion beam monitor is relatively large; and a relative increase of the generation quantity of the electron beam in a position in the ion source corresponding to a monitor point where the ion beam current density measured by the ion beam monitor is relatively small is performed, thereby performing the control of homogenizing the Y-direction ion beam current density distribution measured by the ion beam monitor. According to the configuration, the homogenization of the ion beam current density distribution in the Y direction in the implanting position can be improved.

According to fifth and sixth aspects of the present invention, (a) the controlling device may have functions of: supplying an extraction signal which is an original of the extraction voltage to be supplied from the electron-beam power source to the electron beam source, to the electron-beam power source; calculating an average value of ion beam current densities in a Y-direction distribution measured by the ion beam monitor; uniformly controlling filament currents to be flown through the filaments of the ion source so that the calculate average value is substantially equal to a preset predetermined ion beam current density; calculating an error of the Y-direction distribution which is a difference between the ion beam current density in a Y-direction distribution measured by the ion beam monitor, and the preset ion beam current density; determining a monitor point where the calculated error is larger than a predetermined allowable error, and a sign of an error at the monitor point; determining a scan voltage corresponding to the determined monitor point; based on the determined sign of the error, decreasing the extraction voltage at a scan voltage corresponding to a monitor point where the measured ion beam current density is larger, in proportion to a degree of the error, and increasing the extraction voltage at a scan voltage corresponding to a monitor point where the measured ion beam current density is smaller, in proportion to a degree of the error, thereby shaping a waveform of the extraction signal so that the error is equal to or less than the allowable error at substantially all monitor points on which the ion beam impinges; and storing data of the shaped extraction signal, and data of the filament currents, and (b) the electron-beam power source may have an amplifier which amplifies the scan signal supplied from the controlling device, to produce the scan voltage.

The ion implanter may further comprise an analyzing electromagnet which is disposed between the ion source and the implanting position, and which bends the ion beam from the ion source in the X direction to analyze a momentum.

The ion implanter may further comprise an accelerating/decelerating device which is disposed between the analyzing electromagnet and the implanting position, which bends the ion beam in the X direction by means of an electrostatic field, and which accelerates or decelerates the ion beam.

The present inventions set forth in the first to sixth aspects have the above-described configuration. Therefore, the homogenization of the ion beam current density distribution in the Y direction in the implanting position on a substrate can be improved. As a result, the homogenization of ion implantation on the substrate can be enhanced.

Moreover, the plasma production using the filaments, and the homogenization of the ion beam current density distribution due to the control of the plasma density distribution control using the electron beam sources are combinedly used. Therefore, ion implantation can be easily performed with illuminating the substrate with an ion beam having a large current and high homogenization.

According to a seventh aspect of the present invention, the ion implanter may further comprise:

an analyzing electromagnet which is disposed between the ion source and the implanting position, and which bends the ion beam from the ion source in the X direction to analyze a momentum, the analyzing electromagnet comprising:

a coil having: one set of body portions that are opposed to each other in the X direction across a beam path through which the ion beam passes; and at least one set of connecting portions that connect end portions of the body portions in the Z direction with each other, while avoiding the beam path, the coil generating a magnetic field which bends the ion beam in the X direction; and a yoke which collectively surrounds outer sides of the body portions of the coil, the coil having a configuration in which a notched portion is disposed in a fan-shaped cylindrical stacked coil while leaving the body portions and the connecting portions, the stacked coil being configured by: stacking laminations of an insulation sheet and conductor sheet in which a principal face extends along the Y direction, on an outer peripheral face of a laminated insulator, while winding the laminations in multiple turns; and forming a laminated insulator on an outer peripheral face of the stack.

According to an eighth aspect of the present invention, the ion implanter may further comprise:

an analyzing electromagnet which is disposed between the ion source and the implanting position, and which bends the ion beam from the ion source in the X direction to analyze a momentum, the analyzing electromagnet comprising:

a first coil which is a saddle-shaped coil having: one set of body portions that are opposed to each other in the X direction across a beam path through which the ion beam passes, and that cover about a half or more of one side of the ion beam in the Y direction; and one set of connecting portions that connect end portions of the body portions in the Z direction with each other, while avoiding the beam path, the first coil cooperating with a second coil to generate a magnetic field which bends the ion beam in the X direction;

the second coil which is a saddle-shaped coil having: one set of body portions that are opposed to each other in the X direction across the beam path, and that cover about a half or more of another side of the ion beam in the Y direction; and one set of connecting portions that connect end portions of the body portions in the Z direction with each other, while avoiding the beam path, the second coil being disposed overlappingly with the first coil in the Y direction, and cooperating with the first coil to generate a magnetic field which bends the ion beam in the X direction; and a yoke which collectively surrounds outer sides of the body portions of the first and second coils, each of the first and second coils having a configuration in which a notched portion is disposed in a fan-shaped cylindrical stacked coil while leaving the body portions and the connecting portions, the stacked coil being configured by: stacking laminations of an insulation sheet and conductor sheet in which a principal face extends along the Y direction, on an outer peripheral face of a laminated insulator, while winding the laminations in multiple turns; and forming a laminated insulator on an outer peripheral face of the stack.

According to a ninth aspect of the present invention, the ion implanter may further comprise:

an analyzing electromagnet which is disposed between the ion source and the implanting position, and which bends the ion beam from the ion source in the X direction to analyze a momentum, the analyzing electromagnet comprising:

an inner coil having: one set of body portions that are opposed to each other in the X direction across a beam path through which the ion beam passes; and a connecting portion which connects end portions of the body portions in the Z direction with each other, while avoiding the beam path, the inner coil generating a main magnetic field which bends the ion beam in the X direction;

one or more first outer coils which are saddle-shaped coils having: one set of body portions that are outside the inner coil, and that are opposed to each other in the X direction across the beam path; and one set of connecting portions that connect end portions of the body portions in the Z direction with each other, while avoiding the beam path, the first outer coils generating a sub-magnetic field which assists or corrects the main magnetic field;

one or more second outer coils which are saddle-shaped coils having: one set of body portions that are outside the inner coil, and that are opposed to each other in the X direction across the beam path; and one set of connecting portions that connect end portions of the body portions in the Z direction with each other, while avoiding the beam path, the second outer coils being disposed overlappingly with the first outer coils in the Y direction, and generating a sub-magnetic field which assists or corrects the main magnetic field; and a yoke which collectively surrounds outer sides of the body portions of the inner coil, and the first and second outer coils, each of the inner coil, and the first and second outer coils having a configuration in which a notched portion is disposed in a fan-shaped cylindrical stacked coil while leaving the body portions and the connecting portions, the stacked coil being configured by: stacking laminations of an insulation sheet and conductor sheet in which a principal face extends along the Y direction, on an outer peripheral face of a laminated insulator, while winding the laminations in multiple turns; forming a laminated insulator on an outer peripheral face of the stack; stacking laminations of an insulation sheet and conductor sheet in which a principal face extends along the Y direction, on an outer peripheral face of the stack, while winding the laminations in multiple turns; and forming a laminated insulator on an outer peripheral face of the stack.

According to a tenth aspect of the present invention, the ion implanter may further comprise:

an analyzing electromagnet which is disposed between the ion source and the implanting position, and which bends the ion beam from the ion source in the X direction to analyze a momentum, the analyzing electromagnet comprising:

a first inner coil which is a saddle-shaped coil having: one set of body portions that are opposed to each other in the X direction across a beam path through which the ion beam passes, and that cover about a half or more of one side of the ion beam in the Y direction; and one set of connecting portions that connect end portions of the body portions in the Z direction with each other, while avoiding the beam path, the first coil cooperating with a second inner coil to generate a main magnetic field which bends the ion beam in the X direction;

the second inner coil which is a saddle-shaped coil having: one set of body portions that are opposed to each other in the X direction across the beam path, and that cover about a half or more of another side of the ion beam in the Y direction; and one set of connecting portions that connect end portions of the body portions in the Z direction with each other, while avoiding the beam path, the second inner coil being disposed overlappingly with the first inner coil in the Y direction, and cooperating with the first inner coil to generate the main magnetic field which bends the ion beam in the X direction;

one or more first outer coils which are saddle-shaped coils having: one set of body portions that are outside the first inner coil, and that are opposed to each other in the X direction across the beam path; and one set of connecting portions that connect end portions of the body portions in the Z direction with each other, while avoiding the beam path, the first outer coils generating a sub-magnetic field which assists or corrects the main magnetic field;

one or more second outer coils which are saddle-shaped coils having: one set of body portions that are outside the second inner coil, and that are opposed to each other in the X direction across the beam path; and one set of connecting portions that connect end portions of the body portions in the Z direction with each other, while avoiding the beam path, the second outer coils being disposed overlappingly with the first outer coils in the Y direction, and generating a sub-magnetic field which assists or corrects the main magnetic field; and a yoke which collectively surrounds outer sides of the body portions of the first and second inner coils, and the first and second outer coils, each of the first inner coil and the first outer coil having a configuration in which a notched portion is disposed in a fan-shaped cylindrical stacked coil while leaving the body portions and the connecting portions, the stacked coil being configured by: stacking laminations of an insulation sheet and conductor sheet in which a principal face extends along the Y direction, on an outer peripheral face of a laminated insulator, while winding the laminations in multiple turns; forming a laminated insulator on an outer peripheral face of the stack; stacking laminations of an insulation sheet and conductor sheet in which a principal face extends along the Y direction, on an outer peripheral face of the stack, while winding the laminations in multiple turns; and forming a laminated insulator on an outer peripheral face of the stack, and each of the second inner coil and the second outer coil having a configuration in which a notched portion is disposed in a fan-shaped cylindrical stacked coil while leaving the body portions and the connecting portions, the stacked coil being configured by: stacking laminations of an insulation sheet and conductor sheet in which a principal face extends along the Y direction, on an outer peripheral face of a laminated insulator, while winding the laminations in multiple turns; forming a laminated insulator on an outer peripheral face of the stack; stacking laminations of an insulation sheet and conductor sheet in which a principal face extends along the Y direction, on an outer peripheral face of the stack, while winding the laminations in multiple turns; and forming a laminated insulator on an outer peripheral face of the stack.

According to an eleventh aspect of the present invention, the analyzing electromagnet may further comprise one set of magnet poles which are inwardly projected from the yoke so as to be opposed to each other in the Y direction across the beam path.

The present inventions set forth in the seventh to eleventh aspects comprise the above-described analyzing electromagnet, and therefore attain the following further effects.

Each coil of the analyzing electromagnet is configured so that the notched portion is disposed in the fan-shaped cylindrical stacked coil as described above while leaving the body portions and the connecting portions, and hence the connecting portions are in a state where the portions are extended in the Y direction from end portions of the body portions in substantially parallel. Even in the case where the dimension in the Y direction of the body portions is increased, the case is coped with by correspondingly increasing the dimension in the Y direction of the connecting portions. As a result, the projection distances of the connecting portions in the directions of beam incidence and emission are not increased. According to the structure, the distances where the connecting portions of the coil are projected from the yoke in the directions of beam incidence and emission can be reduced.

Therefore, the size of the analyzing electromagnet can be reduced, and the area required for installing the analyzing electromagnet can be reduced. Also the weight of the analyzing electromagnet can be reduced. Moreover, the possibility that the magnetic field generated by the connecting portions of the coils disturbs the form of the ion beam is reduced.

In accordance with that the projection distances of the connecting portions of each coil can be reduced, also the lengths of the connecting portions can be shortened, and hence wasteful power consumption in the connecting portions can be reduced. Moreover, each coil has the structure in which the conductor sheets are stacked with interposing the insulation sheet therebetween. As compared with a multi-turn coil in which a coated conductor is wound many times, therefore, the space factor of the conductor is high, and the power loss is correspondingly low. Consequently, the power consumption can be reduced.

As a result, in accordance with the miniaturization of the analyzing electromagnet, the size of the ion implanter can be reduced, and therefore the area required for installing the ion implanter can be reduced. Also the weight of the ion implanter can be reduced. Moreover, in accordance with the reduction of the power consumption of the analyzing electromagnet, the power consumption of the ion implanter can be reduced.

The present invention set forth in the eight aspect can attain the following further effect. Namely, since the analyzing electromagnet comprises the first and second coils, it is possible to easily cope with an ion beam having a large Y-direction dimension.

The present invention set forth in the ninth aspect can attain the following further effect. Namely, since the analyzing electromagnet comprises the first and second outer coils in addition to the inner coil, it is possible to generate a magnetic field in which the homogenization of the magnetic flux density distribution in the Y direction is high, in the beam path of the ion beam. As a result, the disturbance of the form of the ion beam at emission can be suppressed to a lower level. This effect is more remarkable in the case where the ion beam has a large Y-direction dimension.

The present invention set forth in the tenth aspect can attain the following further effects. Namely, since the analyzing electromagnet comprises the first and second outer coils in addition to the first and second inner coils, it is possible to easily cope with an ion beam having a large Y-direction dimension, and also to generate a magnetic field in which the homogenization of the magnetic flux density distribution in the Y direction is high, in the beam path of the ion beam. As a result, the disturbance of the form of the ion beam at emission can be suppressed to a lower level. This effect is more remarkable in the case where the ion beam has a large Y-direction dimension.

The present invention set forth in the eleventh aspect can attain the following further effect. Namely, since the analyzing electromagnet further comprises the magnetic poles, the magnetic field can be easily concentrated in the gap between the magnetic poles, and hence it is possible to easily generate a magnetic field of a high magnetic flux density in the beam path.

According to a twelfth aspect of the present invention, the ion implanter may further comprise:

an accelerating/decelerating device which is disposed between an analyzing electromagnet that bends the ion beam from said ion source in the X direction to analyze a momentum, and the implanting position, which bends the ion beam in the X direction by means of an electrostatic field, and which accelerates or decelerates the ion beam, said accelerating/decelerating device having first to third electrodes which are arranged in a sequence of said first electrode, said second electrode, and said third electrode in the ion beam traveling direction with starting from an upstream side, and accelerating or decelerating the ion beam in two stages between said first and second electrodes, and said second and third electrodes, said second electrode being configured by two electrode members which are opposed to each other in the X direction across the path of the ion beam, and to which different potentials are applied to deflect the ion beam in the X direction, said third electrode being disposed along an orbit of an ion beam having a specific energy after the deflection.

The present invention set forth in the twelfth aspect comprises the above-described accelerating/decelerating device, and therefore attains the following further effects.

Namely, in the accelerating/decelerating device, the ion beam can be deflected by the portion of the second electrode which is dividedly configured by two electrode members, thereby attaining the effect of energy separation. The existence of the third electrode enables an ion beam having a specific energy to be efficiently derived, and ions other than the ion beam, and neutral particles can be efficiently blocked by the third electrode. Therefore, energy contamination can be suppressed more effectively. Particularly, it is empirically known that, in the deceleration mode, neutral particles are easily generated by charge conversion in ion deceleration between the first and second electrodes. Even when many neutral particles are generated, however, they straightly travel and impinge on the third electrode to be blocked. Therefore, neutral particles can be effectively eliminated in the accelerating/decelerating device.

Furthermore, the ion beam can be accelerated in two stages, and, before acceleration in the latter one of the stages, can be deflected. Therefore, the deflection is facilitated. Moreover, electrons which are generated by collision of unwanted ions are bent by the second electrode to prevent the electrons from reaching the first electrode. Therefore, the energy of X rays generated by collision of the electrons can be lowered.

Other features and advantages may be apparent from the following detailed description, the accompanying drawings and the claims.

BRIEF DESCRIPTION OF THE DRAWINGS

FIG. 23 is a perspective view showing first and second inner coils shown in FIG. 22.

FIG. 37 is a perspective view showing another example of a coil of the analyzing electromagnet.

DETAILED DESCRIPTION (1) About Whole Ion Implanter

Figure 1:
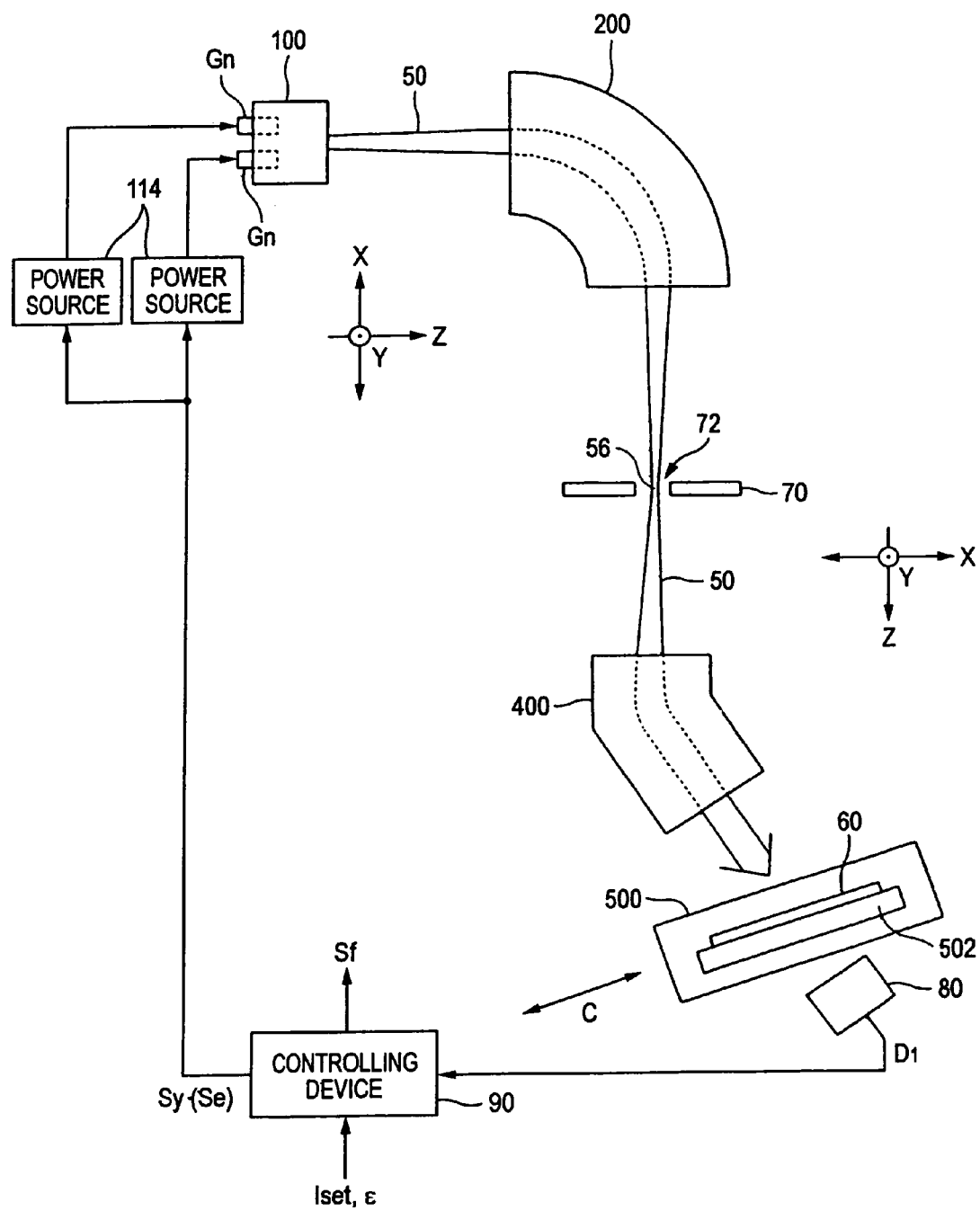
FIG. 1 is a schematic plan view showing an embodiment of the ion implanter of the present invention.

FIG. 1 is a schematic plan view showing an embodiment of the ion implanter of the invention. In the specification and the drawings, the traveling direction of an ion beam 50 is always set as the Z direction, and two directions which are substantially orthogonal to each other in a plane that is substantially orthogonal to the Z direction are set as X and Y directions, respectively. For example, the X and Z directions are horizontal directions, and the Y direction is a vertical direction. The Y direction is a constant direction, but the X direction is not an absolute direction but changes in accordance with the position of the ion beam 50 on the path (for example, see FIG. 1). In the specification, the case where ions constituting the ion beam 50 are positive ions will be described as an example.

The ion implanter is an apparatus for irradiating a substrate 60 with the ribbon-like ion beam 50 to perform ion implantation, and comprises: an ion source 100 that generates the ribbon-like ion beam 50; an analyzing electromagnet 200 which bends the ion beam 50 from the ion source 100 in the X direction to analyze a momentum (for example, mass analysis, the same shall apply hereinafter), and which forms a focus (the focus in the X direction, the same shall apply hereinafter) 56 of the ion beam 50 of a desired momentum, in a downstream side; and a substrate driving device 500 which, in an implanting position where the ion beam 50 passed through the analyzing electromagnet 200 is caused to be incident on the substrate 60, moves (see the arrow C) the substrate 60 in a direction intersecting with the principal face 52 (see FIGS. 2 and 3) of the ion beam 50. For example, the movement is a reciprocal linear movement. The substrate driving device 500 has a holder 502 which holds the substrate 60.

The path of the ion beam 50 from the ion source 100 to the substrate 60 is in a vacuum vessel which is not shown, and maintained to a vacuum atmosphere.

In the specification, "principal face" does not mean an end face of a ribbon-like or sheet-like member (for example, the ion beam 50, and insulation sheets 266, 267 and conductor sheets 268, 269 which will be described later), but means a larger face of the member. The term "downstream side" or "upstream side" means the downstream side or the upstream side in the traveling direction Z of the ion beam 50. The ion beam 50 generated from the ion source 100, and the ion beam 50 derived from the analyzing electromagnet 200 are different from each other in content. Namely, the former is the ion beam before momentum analysis, and the latter is that after momentum analysis. The difference between the ion beams is obvious. In the specification, therefore, the ion beams are not distinguished from each other, and the both are indicated as the ion beam 50.

Figure 2:
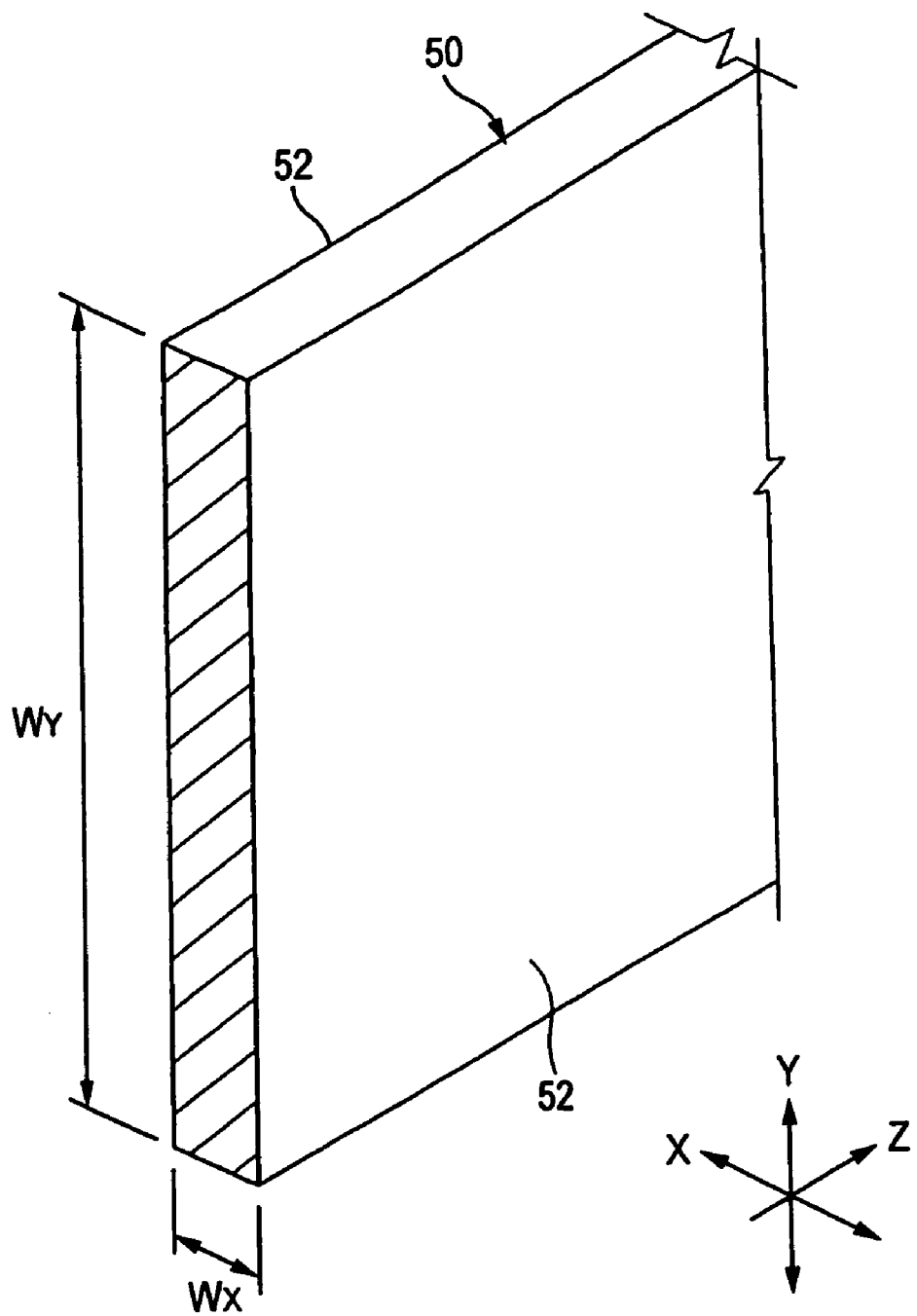
FIG. 2 is a schematic perspective view partially showing an example of a ribbon-like ion beam.

The ion beam 50 which is generated from the ion source 100 and transported to the substrate 60 has a ribbon-like shape in which, as shown in FIG. 2, for example, the dimension $W_Y$ in the Y direction is larger than the dimension $W_X$ in the X direction, or namely $W_Y > W_X$. Although the ion beam 50 has a ribbon-like shape, this does not mean that the dimension $W_X$ in the X direction is as thin as paper or cloth. For example, the dimension $W_X$ in the X direction of the ion beam 50 is about 30 to 80 mm, and, although depending on the dimension of the substrate 60, the dimension $W_Y$ in the Y direction is about 300 to 500 mm. The plane in which the ion beam 50 is larger, i.e., the plane along the YZ plane is the principal face 52.

Figure 3:
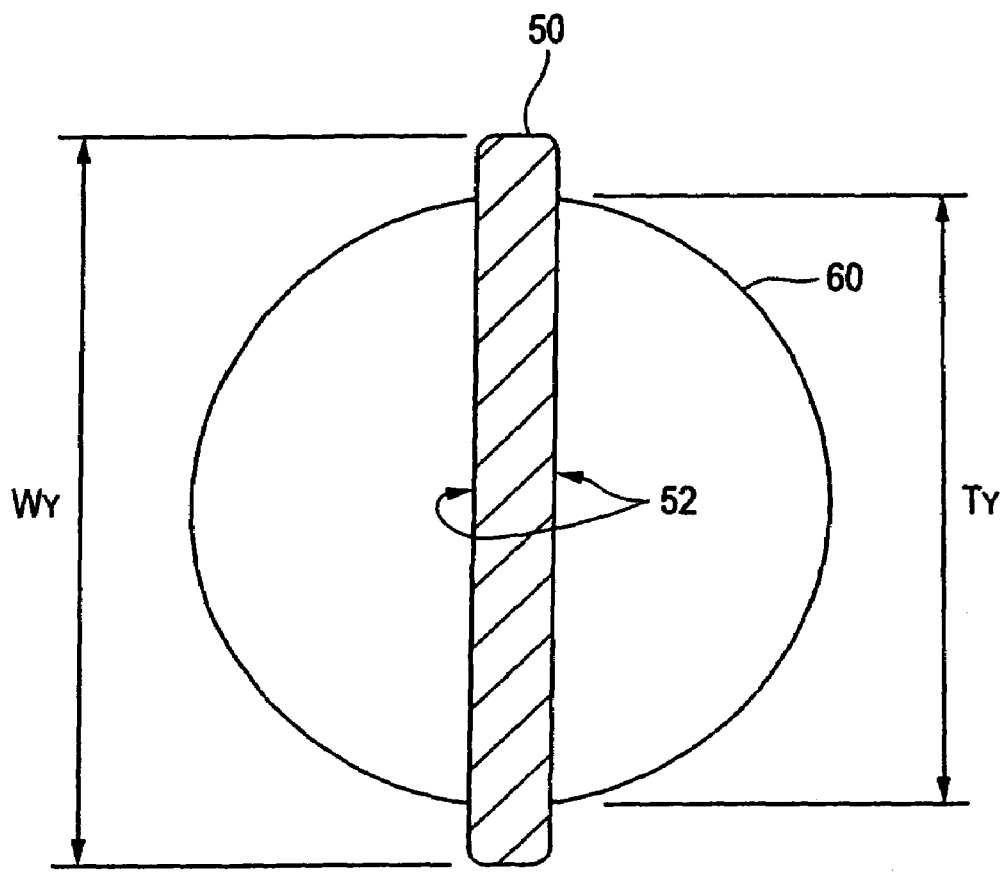
FIG. 3 is a view showing an example of dimensional relationships in the Y direction between an ion beam and a substrate.

The ion source 100 generates the ribbon-like ion beam 50 in which, as in an example shown in FIG. 3, the dimension $W_Y$ in the Y direction is larger than the dimension $T_Y$ in the Y direction of the substrate 60. When the dimension $T_Y$ is 300 to 400 mm, for example, the dimension $W_Y$ is about 400 to 500 mm. Because of such dimensional relationships and the above-described movement of the substrate 60, the whole face of the substrate 60 can be illuminated with the ion beam 50 to perform the ion implantation.

For example, the substrate 60 is a semiconductor substrate, a glass substrate, or another substrate. The plan-view shape of the substrate is circular or rectangular.

In the vicinity of a focus 56 of the ion beam 50 emitted from the analyzing electromagnet 200, a slit 70 which cooperates with the analyzing electromagnet 200 to analyze the momentum of the ion beam 50 is disposed. The analysis slit 70 has a slit 72 which extends substantially parallel to the Y direction. The reason why the analysis slit 70 is disposed in the vicinity of the focus 56 of the ion beam 50 is that both the transport efficiency of the ion beam 50 and the resolution of momentum analysis are enhanced.

The analyzing electromagnet 200, the analysis slit 70, and an accelerating/decelerating device 400 which will be described later can be disposed as required.

As described in detail later, plural electron beam sources Gn are disposed in the ion source 100 (specifically, a plasma vessel 118 constituting the ion source). An extraction voltage for controlling the generation quantity of the electron beam, and a scan voltage for scanning in the Y direction are supplied to each of the electron beam sources Gn from a corresponding electron-beam power source 114. In the embodiment, the numbers of the electron beam sources Gn and electron-beam power sources 114 are two respectively. The numbers are not restricted to this value. Each of the numbers may be one, or a plural number other than two. Namely, both of the numbers are arbitrary numbers of one or more.

An ion beam monitor 80 is disposed which measures the Y-direction ion beam current density distribution of the ion beam 50 in an implanting position where the ion beam 50 is caused to be incident on the substrate 60 or a vicinity of the position, and at plural monitor points in the Y direction. Measurement data $D_1$ indicative of the beam current density distribution is output from the ion beam monitor 80, and then supplied to a controlling device 90.

As in the example shown in FIG. 1, for example, the ion beam monitor 80 may be disposed in the vicinity of the rear side (in other words, downstream side) of the implanting position. Alternatively, the monitor may be disposed in the vicinity of the front side (in other words, upstream side) of the implanting position, or may be configured so as to be movable to the implanting position. The ion beam monitor 80, the substrate 60, and the holder 502 are requested to be disposed so as not to interfere with each other. In the case where the ion beam monitor 80 is disposed in the vicinity of the rear side of the implanting position, during the measurement, the substrate 60 and the holder 502 may be moved to a position where interference to the measurement does not occur. In the case where the ion beam monitor 80 is disposed in the vicinity of the front side of the implanting position, during the implantation, the ion beam monitor 80 may be moved to a position where interference to the implantation does not occur.

The ion implanter further comprises the controlling device 90 which controls the electron-beam power sources 114 on the basis of the measurement data $D_1$ supplied from the ion beam monitor 80. In the embodiment, the controlling device 90 can control also a filament current If which will be described later.

Figure 4:
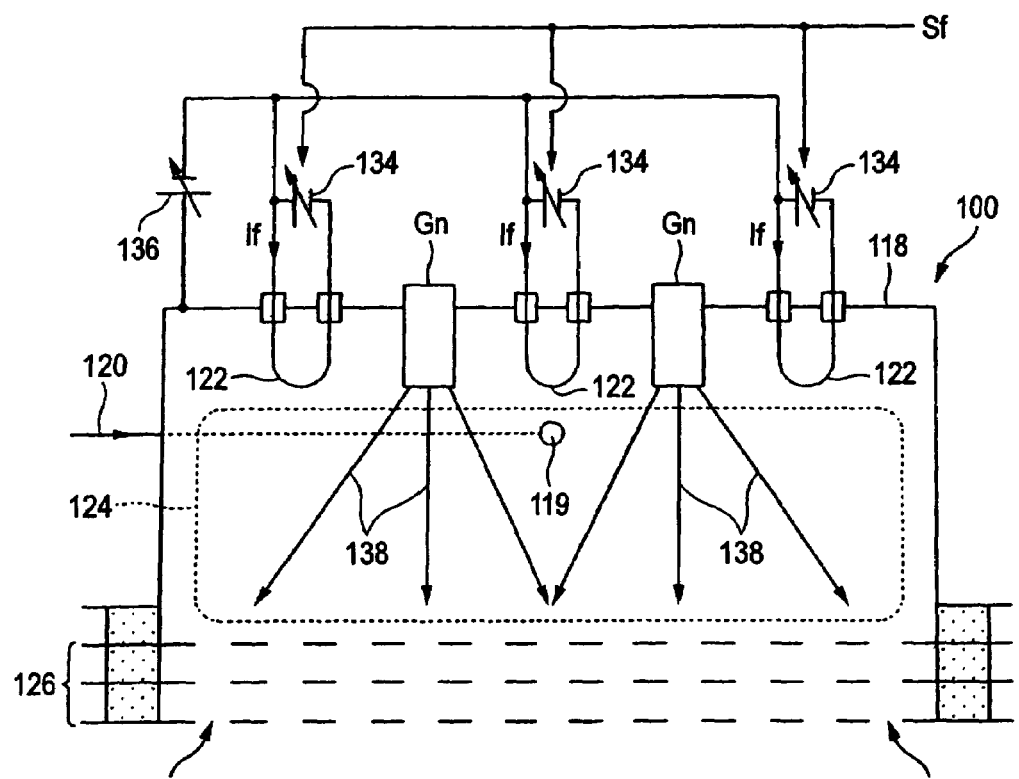
FIG. 4 is a schematic section view showing an example of the configuration of an ion source shown in FIG. 1.

(2) About Ion Source 100, Electron Beam Sources Gn, and the Like, and their Control As shown in FIG. 4, the ion source 100 has a configuration where a gas (including the case of vapor) 120 for producing a plasma is introduced via a gas introduction port 119, one or more (in the embodiment, three) filaments 122 are disposed in the plasma vessel 118 which has, for example, a rectangular parallelepiped shape, arc discharges are generated between the filaments 122 and the plasma vessel 118 which functions also as an anode, the gas 120 is ionized to produce a plasma 124, and the above-described ribbon-like ion beam 50 is extracted from the plasma 124 by an extraction electrode system 126.

The gas 120 is a gas containing desired elements (for example, dopants such as B, P, and As). Specific examples of the gas are gases containing a source gas such as $BF_3$, $PH_3$, $AsH_3$, or $B_2H_6$.

As required, the gas introduction port 119 may be in plural places arranged in the Y direction. According to the configuration, it is easy to homogenize the gas concentration distribution in the plasma vessel 118, thereby facilitating homogenization of the plasma density distribution.

The extraction electrode system 126 has one or more (in the illustrated example, three) electrodes. The electrodes have ion extraction holes 128 in corresponding positions, respectively. The shape, arrangement, and the like of the ion extraction holes 128 of the extraction electrode system 126 (specifically, the electrodes of the system) are adequately determined in accordance with the section shape of the extracted ion beam 50. As in an example shown in FIG. 5, the ion extraction holes 128 may be plural (many) small holes which are arranged in the Y direction, or slits which extend in the Y direction. In accordance with the dimension $W_X$ in the X direction of the ion beam 50, plural (for example, two or three) rows each consisting of plural such ion extraction holes 128 may be arranged in the X direction.

The number of the filaments 122 is an arbitrary number of one or more. In order to generate the ion beam 50 having a large Y-direction dimension $W_Y$ and high homogenization, it is preferable to arrange plural filaments 122 in the Y direction.

Figure 5:
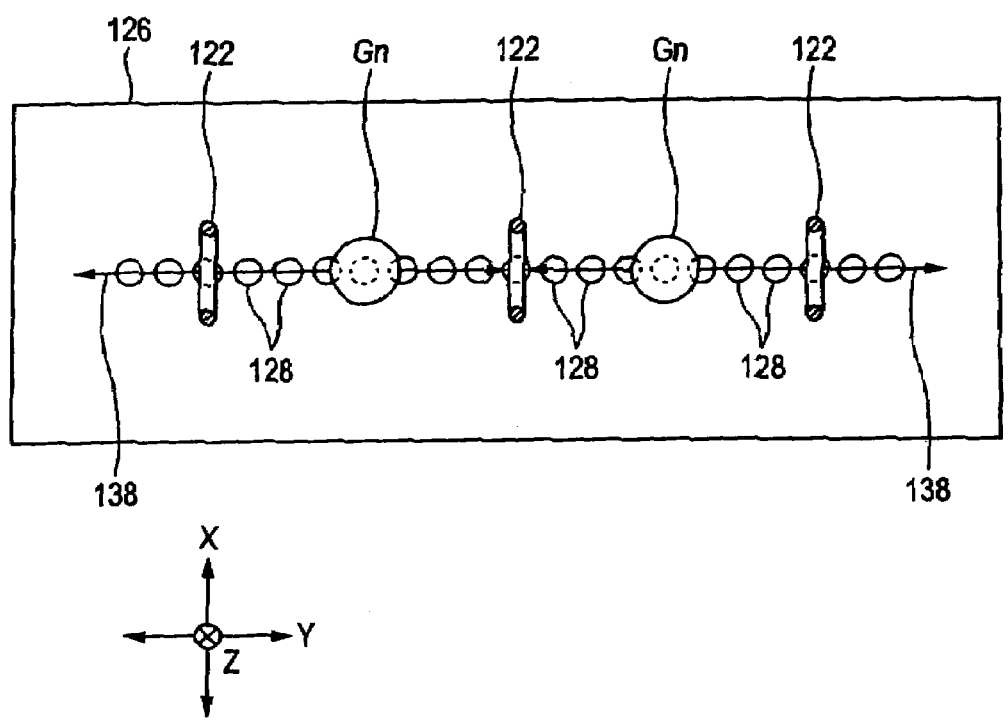
FIG. 5 is a schematic plan view showing an example of arrangement of filaments and electron beam sources in the ion source shown in FIG. 4, the scan locus of an electron beam, etc.
Figure 6:
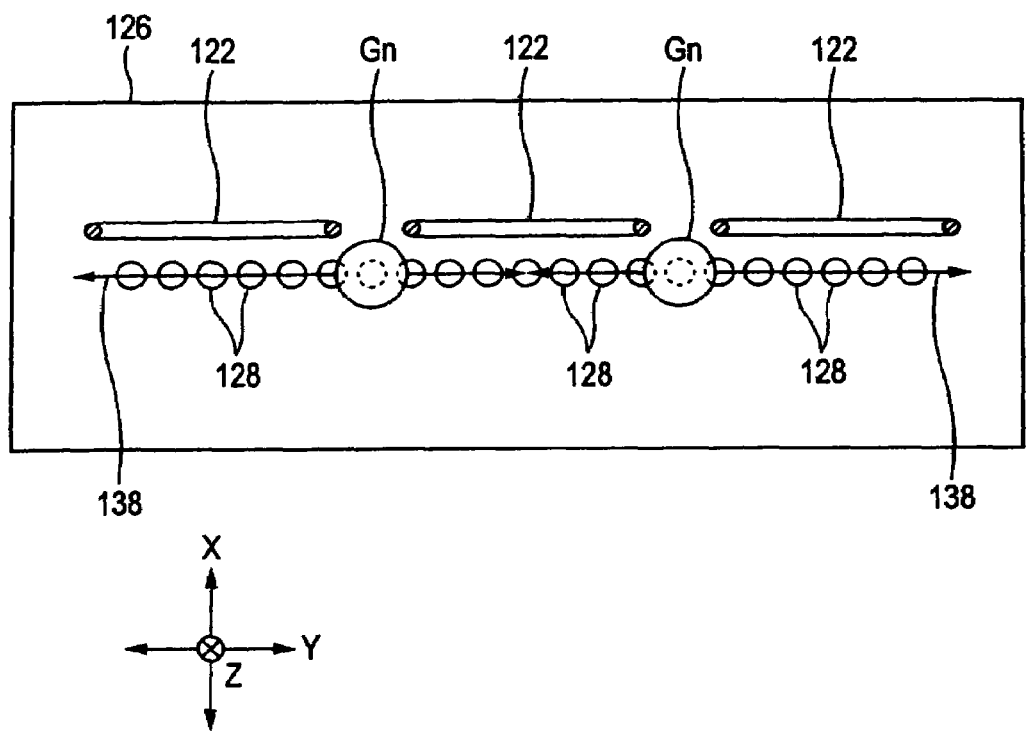
FIG. 6 is a schematic plan view showing another example of arrangement of filaments.

As in the examples shown in FIGS. 4 and 5, the filaments 122 may have a U-like shape, or, as in an example shown in FIG. 6, a linear shape which extends along the Y direction. The filaments may have another shape.

The U-like filaments 122 may have a shape which, as shown in FIG. 4, is bent back in the YZ plane, or which, as shown in FIG. 5, is bent back in the XZ plane.

As shown in FIG. 4, each of the filaments 122 receives the filament current If from a voltage-variable filament power source 134, and heated to emit thermoelectrons. A DC arc power source 136 for generating an arc discharge is connected between one end of each of the filaments 122 and the plasma vessel 118. In the embodiment, the filament power source 134 can change (increase or decrease) the filament current If in response to a filament current control signal Sf supplied from the controlling device 90.

In this example, one filament power source 134 is disposed for each filament 122. However, it is not necessary to separately dispose the plural filament power sources 134. The filament power sources may be assembled into one unit, or configured as one filament power source which can cause filament currents If to independently flow through the respective filaments 122. In the example, the arc power source 136 is shared by all of the filaments 122. Alternatively, one arc power source may be disposed for each filament 122. In the case of a shared power source, it is possible to simplify the configuration.

Magnets for forming a multi-pole magnetic field (multi-cusp magnetic field) which is used for producing and maintaining the plasma 124 may be arranged in the periphery of the plasma vessel 118. An ion source having such a structure is called also a bucket ion source (or an ion source of the multi-pole magnetic field type).

The electron beam sources Gn are placed between the plural filaments 122, specifically at midpoints, respectively. In the embodiment, as shown in FIG. 7, each of the electron beam sources Gn has: a filament 140 which emits electrons (thermoelectrons); an anode 144 which extracts the electrons as an electron beam 138; an extraction electrode 142 which is placed between the two components 140, 144, and which controls the generation quantity of the electron beam without changing the energy of the electron beam 138; and a pair of scan electrodes 146 which scan the electron beam 138 to be extracted to the outside, in the Y direction.

According to the configuration, each of the electron beam sources Gn generates the electron beam 138, and emits the electron beam into the plasma vessel 118 of the ion source 100, so that the gas 120 is ionized by the electron beam 138 to produce the plasma 124. Moreover, the electron beam 138 can be one-dimensionally scanned in the Y direction in the ion source 100 (specifically, in the plasma vessel 118). An example of the scan locus is shown in FIGS. 5 and 6. Briefly speaking, the electron beam sources Gn are used for correcting the density distribution of the plasma 124 produced by the filaments 122. The embodiment has two electron beam sources Gn. However, the number of the electron beam sources is not restricted to two. The number may be one, or a plural number other than two. Namely, the number is an arbitrary number of one or more.

Figure 7:
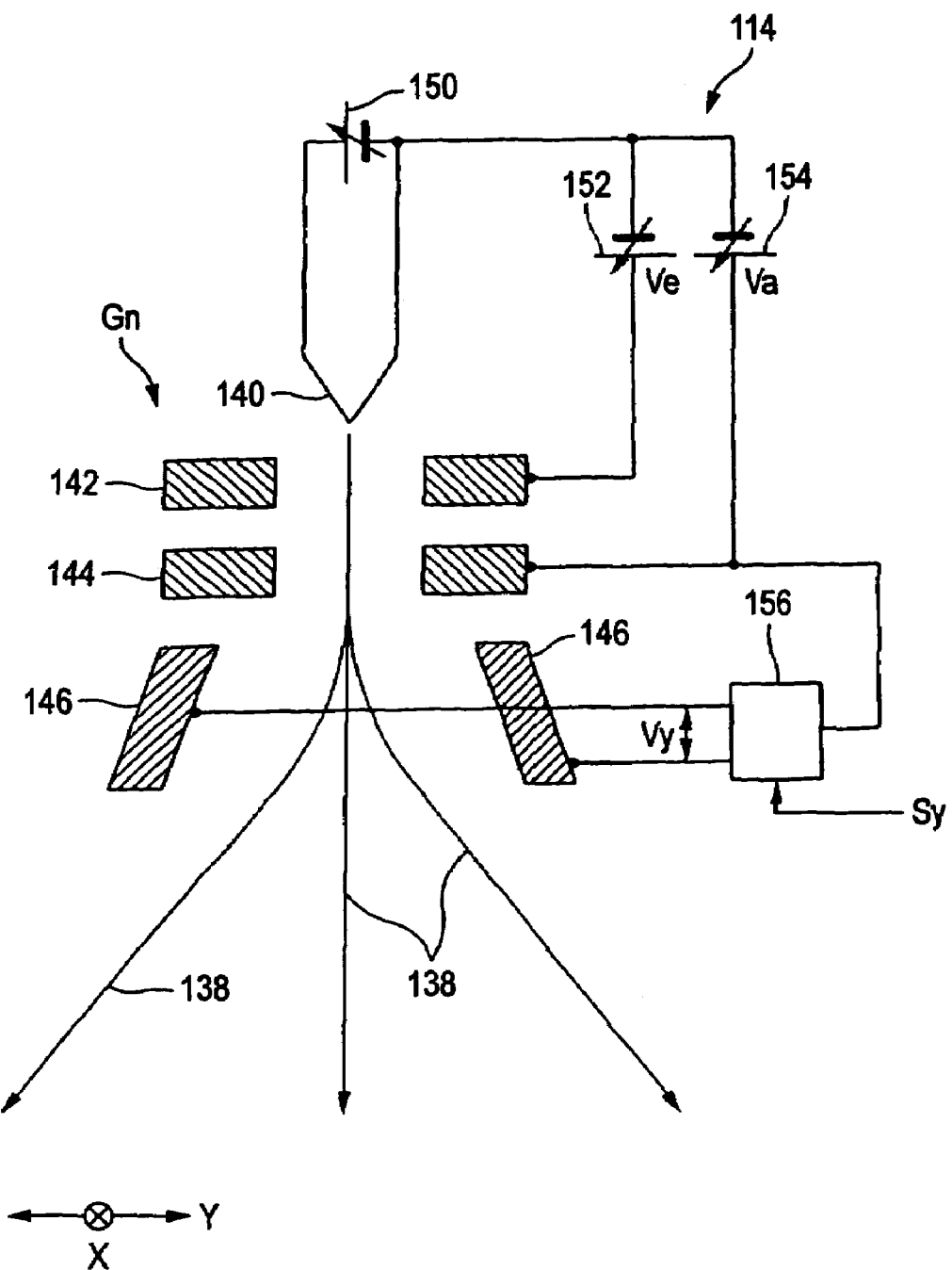
FIG. 7 is a view showing an example of the configuration of an electron beam source and electron-beam power source shown in FIG. 1.

In the example shown in FIG. 7, each of the electron-beam power sources 114 has: a filament power source 150 which heats the filament 140; an extraction power source 152 which applies a DC extraction voltage Ve for controlling the quantity of the electron beam 138, between the filament 140 and the extraction electrode 142; an energy control power source 154 which applies a DC anode voltage Va between the filament 140 and the anode 144; and an amplifier 156 which applies a scan voltage Vy for Y-direction scanning between the pair of scan electrodes 146. In the embodiment, the filament power source 150 is a DC power source. Alternatively, the filament power source may be an AC power source.

For example, the controlling device 90 has a function of supplying a scan signal Sy which is an original of the scan voltage Vy, and the amplifier 156 amplifies (voltage-amplifies) the scan signal Sy supplied from the controlling device 90 to produce (output) the scan voltage Vy. In the example, the scan voltage Vy is swung in the ± directions with reference to the potential of the anode 144. According to the configuration, the electron-beam power sources 114 can supply the extraction voltage Ve for controlling the quantity of the electron beam 138, the scan voltage Vy for Y-direction scanning, and the like, to the corresponding electron beam sources Gn.

Briefly speaking, the energy of the electron beam 138 extracted from each electron beam source Gn is determined on the level of the anode voltage Va, and becomes Va [eV]. The energy of the electron beam 138 is set to a level at which the gas 120 can be ionized by electron impact in the plasma vessel 118. When the gas 120 is a gas of the above-described kind, for example, the energy may be set to about 500 eV to 3 keV, specifically about 1 keV.

Figure 9:
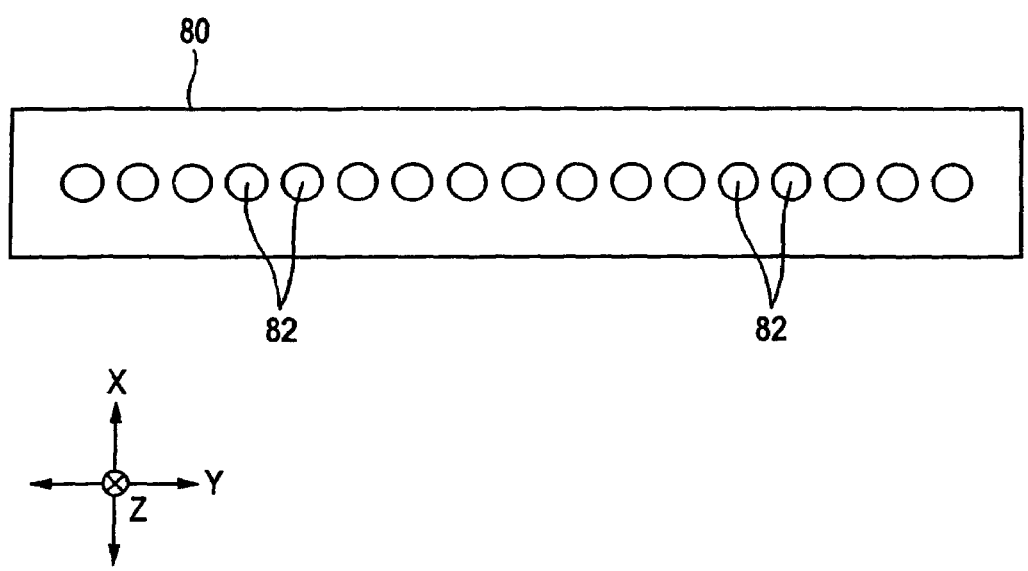
FIG. 9 is a schematic front view showing an example of the ion beam monitor shown in FIG. 1.

The ion beam monitor 80 measures the Y-direction ion beam current density distribution of the ion beam 50, at plural monitor points arranged in the Y direction. As in an example shown in FIG. 9, for example, the ion beam monitor 80 has plural (many) beam current measuring devices (for example, Faraday cups) 82 which are arranged in the Y direction. The arrangement length of the plural beam current measuring devices 82 may be slightly larger than the dimension $W_Y$ in the Y direction of the ion beam 50. According to the configuration, the whole of the ion beam 50 in the Y direction can be measured. The beam current measuring devices 82 correspond to the monitor points, respectively. FIG. 9 is a schematic view. The number, shape, arrangement, and the like of the beam current measuring devices 82 are not restricted to those shown in FIG. 9.

For example, each beam current measuring device 82 may be formed into a rectangular shape which extends in the X direction, instead of the circular shape as in the example shown in FIG. 9. In this case, each beam current measuring device 82 may be configured so that the X-direction dimension is larger than the X-direction dimension $W_X$ of the ion beam 50 which is incident on the device, thereby enabling the device to receive the whole ion beam 50 in the X direction. According to the configuration, it is possible to eliminate an influence due to the X-direction ion beam current density distribution of the ion beam 50. In other words, in the X direction, an average ion beam current density can be measured. As described above, the substrate 60 is moved along the X direction (not restricted to movement parallel to the X direction). When the beam current measuring devices 82 are configured as described above, therefore, it is possible to measure the ion beam current density distribution of the ion beam 50 in a state which is more similar to actual ion implantation on the substrate 60.

The ion beam monitor 80 may be configured so that one beam current measuring device 82 is moved in the Y direction by a moving mechanism.

In the specification, the monitor points are not mathematical points which do not have an area, but small measurement places in which the Y-direction dimension is sufficiently smaller than the Y-direction dimension $W_Y$ of the ion beam 50, and which have a predetermined area.

The area of each monitor point is previously known. Therefore, the measurement of the beam current of the ion beam 50 at each monitor point is substantially equivalent to that of the beam current density at the monitor point. This is caused because the beam current density at the monitor point can be obtained by dividing the beam current obtained at the monitor point by the area.

Figure 8:
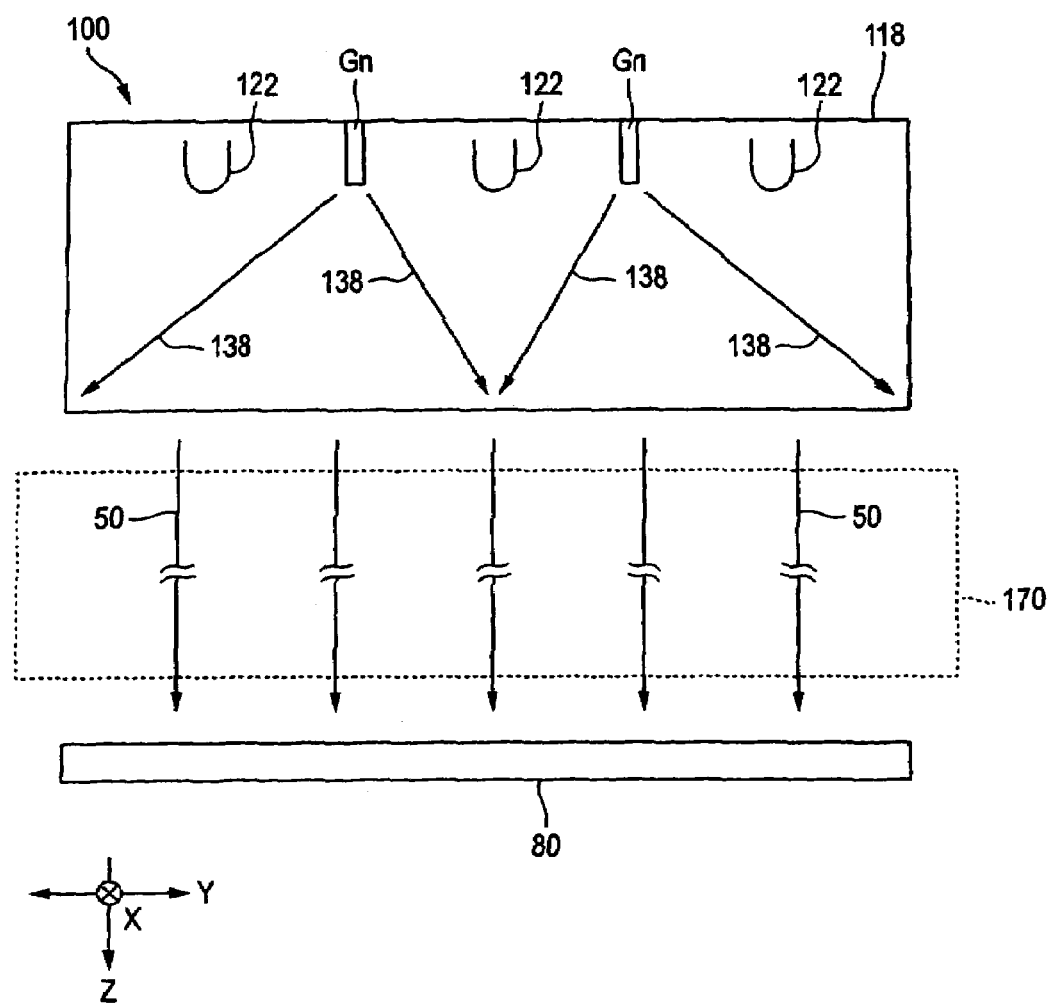
FIG. 8 is a view showing a simplified version of a system from the ion source shown in FIG. 1 to an ion beam monitor.

FIG. 8 shows a simplified version of the system shown in FIG. 1 from the ion source 100 to the ion beam monitor 80. The reference numeral 170 generally denotes the ion beam transport system. The Y direction of the ion source 100 can be set to be substantially parallel to that of the ion beam monitor 80. However, the ion beam transport system 170 is not always linear (see FIG. 1), and the X direction of the ion source 100 and that of the ion beam monitor 80 are not always parallel to each other as shown in FIG. 8. This does not cause a problem.

In the embodiment, the controlling device 90 is configured by a computer having a CPU, a storage device, an input AD converter, an output DA converter, etc. The controlling device 90 has a function of performing one of controls (A) and (B) below, and does not simultaneously perform both controls (A) and (B).

(A) Scanning Speed Control of Electron Beam

In this case, the controlling device 90 has a function of homogenizing the Y-direction ion beam current density distribution measured by the ion beam monitor 80, by, while controlling the electron-beam power sources 114 on the basis of the measurement data $D_1$ of the ion beam monitor 80 to maintain the quantity of the electron beam 138 generated from the electron beam sources Gn to a substantially constant value, performing both of (a) a relative increase of the scanning speed of the electron beam 138 in a position in the ion source corresponding to a monitor point where the ion beam current density measured by the ion beam monitor 80 is relatively large, and (b) a relative decrease of the scanning speed of the electron beam 138 in a position in the ion source corresponding to a monitor point where the measured ion beam current density is relatively small.

(B) Control of Quantity of Electron Beam

In this case, the controlling device 90 has a function of homogenizing the Y-direction ion beam current density distribution measured by the ion beam monitor 80, by, while controlling the electron-beam power sources 114 on the basis of the measurement data $D_1$ of the ion beam monitor 80 to maintain the Y-direction scanning speed of the electron beam 138 generated from the electron beam sources Gn to a substantially constant value, performing both of (a) a relative decrease of the generation quantity of the electron beam 138 in a position in the ion source corresponding to a monitor point where the ion beam current density measured by the ion beam monitor 80 is relatively large, and (b) a relative increase of the generation quantity of the electron beam 138 in a position in the ion source corresponding to a monitor point where the measured ion beam current density is relatively small.

In the case of any of (A) and (B) above, the controlling device 90 may perform at least one of above controls (a) and (b). However, the controlling device preferably performs both of the controls because the control of homogenizing the ion beam current density distribution is faster. The term of "function" may be paraphrased as "means". The same shall apply to the other functions which will be described later.

Specific examples of the controls (A) and (B) will be described below.

(A) Scanning Speed Control of Electron Beam

Figure 10:
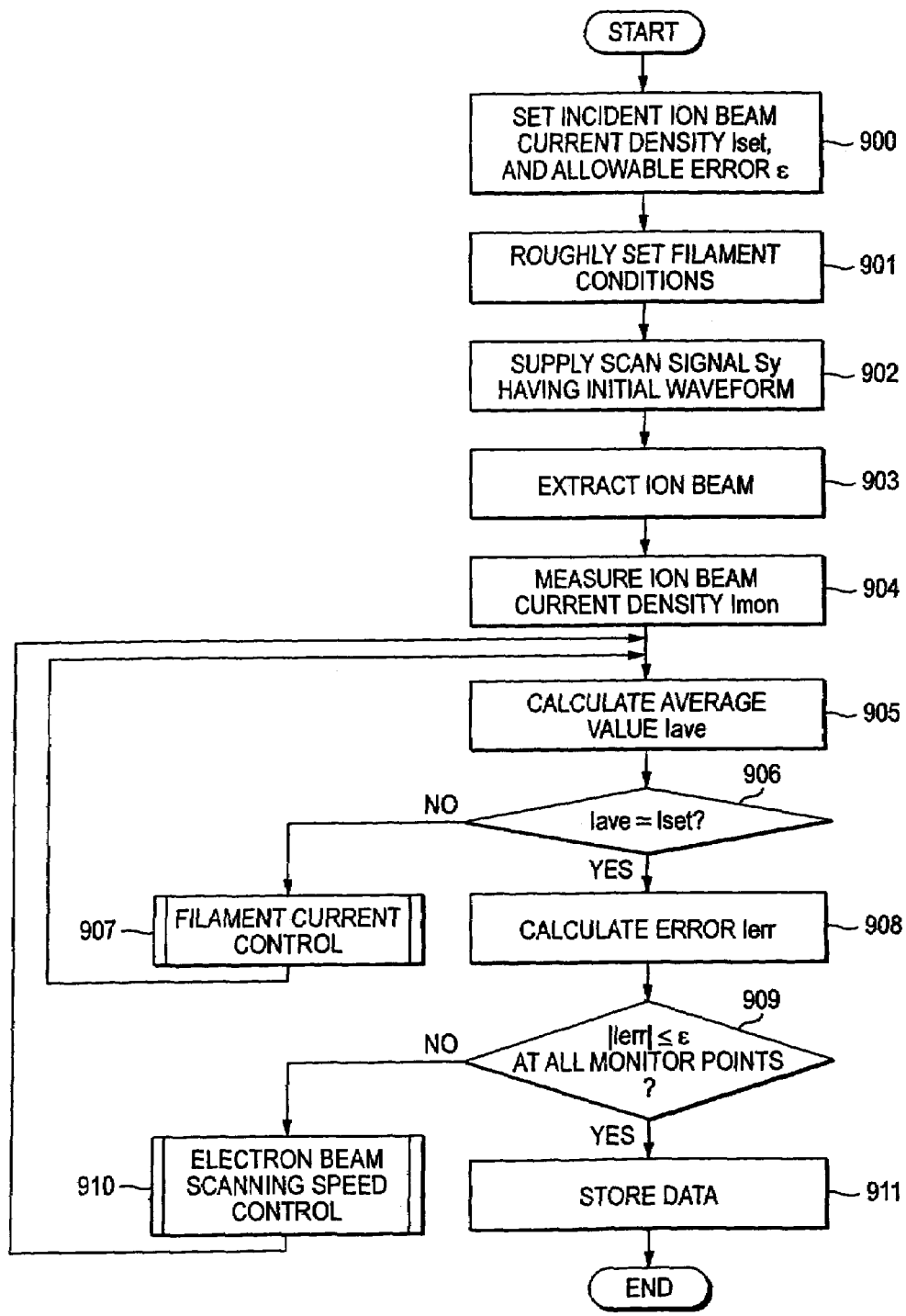
FIG. 10 is a flowchart showing a specific example of contents of a control of homogenizing the Y-direction ion beam current density distribution by using the controlling device shown in FIG. 1.
Figure 11:
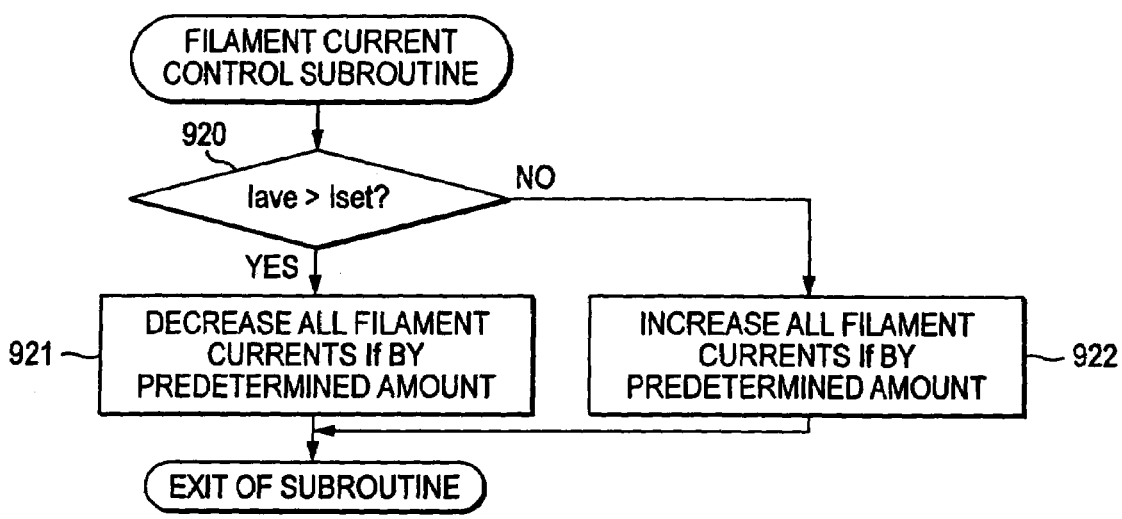
FIG. 11 is a flowchart showing an example of a filament current control subroutine shown in FIG. 10.
Figure 12:
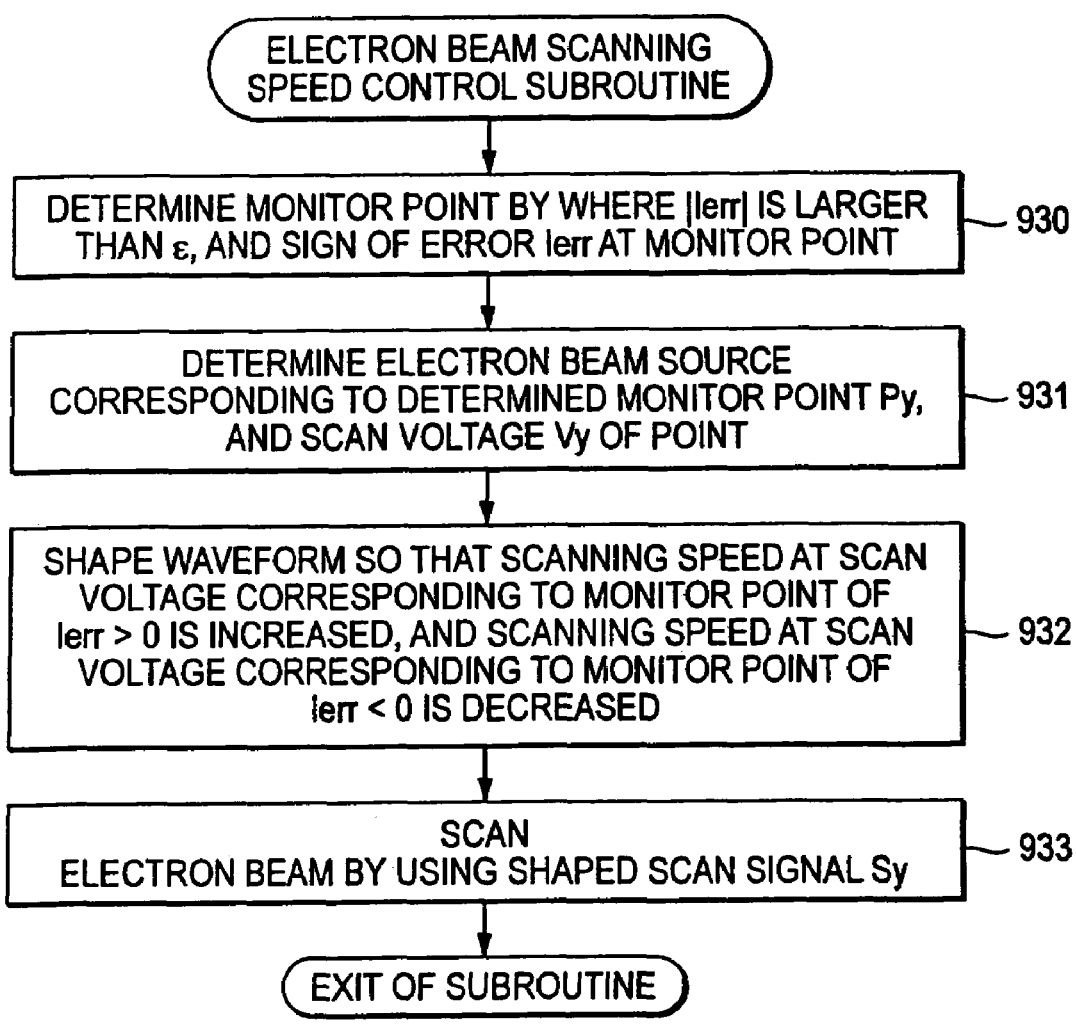
FIG. 12 is a flowchart showing an example of an electron beam scanning speed control subroutine shown in FIG. 10.

In this case, as the electron-beam power sources 114, the power source shown in FIG. 7 is used. In this example, the extraction voltage Ve output from the extraction power source 152 is set constant, and the quantity of the electron beam generated from the electron beam source Gn is set constant. Preferably, also the anode voltage Va output from the energy control power source 154 is set constant, and the energy of the electron beam 138 is set constant. In the embodiment, the values are set constant. FIGS. 10 to 12 show flowcharts of the control which is performed by using the controlling device 90 in this case.

Prior to the control, correspondence relationships among a monitor point Py on the ion beam monitor 80, the electron beam source Gn which shares the increase/decrease of the ion beam current density at the monitor point Py, and the scan voltage Vy supplied to the electron beam source Gn are previously checked, and stored in the controlling device 90. In the case where only one the electron beam source Gn is used, the electron beam source Gn is uniquely determined, and hence it is not necessary to check and store the electron beam source Gn. Furthermore, the electron beam source Gn is not required to be included in the following correspondence relationships.

The correspondence relationships show, when attention is focused on an arbitrary monitor point Py on the ion beam monitor 80, which electron beam source Gn increases/decreases the ion beam current density at the monitor point Py, and the value of the scan voltage Vy supplied to the electron beam source Gn, and can be expressed by following Exp. 1. The suffixes i, j, and k indicate a specific position, and are integers. For example, the correspondence relationships can be determined by checking an electron beam source Gn, a scan voltage Vy, and a monitor point Py where the ion beam current density is increased or decreased at the voltage. The correspondence relationships are uniquely determined by the configuration of ion implanter. When once determined, therefore, they are not changed unless the configuration of ion implanter is modified. Data indicating the correspondence relationships may be stored into the controlling device 90 (specifically, the storage device).

$$Py_i \leftarrow \rightarrow (Gn_j, Vy_k) \qquad \text{[Exp. 1]}$$

The subsequent procedure will be described with reference to FIG. 10, etc. A desired ion beam current density Iset of the ion beam 50 to be impinged on the substrate 60, and an allowable error $\epsilon$ of the density are set in the controlling device 90 (step 900). The ion beam current density Iset which has been set is referred to as the preset ion beam current density. The allowable error $\epsilon$ indicates a degree at which the actual ion beam current density, specifically an ion beam current density Imon measured by the ion beam monitor 80 is allowed to be deviated from the preset ion beam current density Iset.

Next, the filament conditions are roughly set (step 901). This means that, in production of the plasma 124, the ion beam 50 is extracted from the ion source 100 without using the electron beam sources Gn and with using only the filament 122, and the ion beam current density Imon measured by the ion beam monitor 80 is coarsely set in a manual manner. Specifically, the filament power sources 134 are adjusted and the filament currents If to be flown through the filaments 122 of the ion source 100 are roughly set. At this time, an adjustment of the arc current supplied from the arc power source 136 may be additionally performed. Usually, also this rough setting is required to be performed only one time unless the configuration of the ion source 100 or the ion implanter is changed.

When the rough setting of the filament conditions is conducted more finely, the subsequent controls (for example, controls after step 905) can be completed more rapidly. This is applicable also to the case of an example of FIG. 16.

Figure 13:
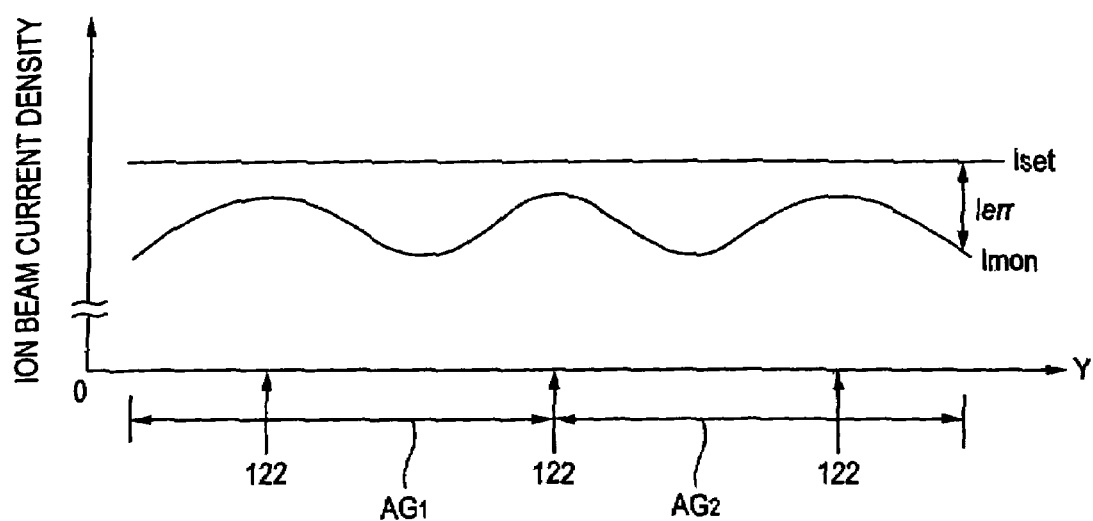
FIG. 13 is a schematic view showing an example of an ion beam current density distribution after rough setting of filament conditions shown in FIG. 10 is performed.
Figure 14A:
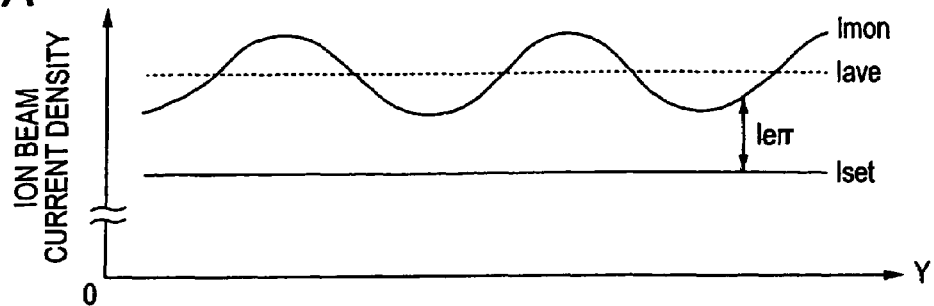
FIGS. 14A to 14D are schematic views showing a process of homogenizing the Y-direction ion beam current density distribution by performing the filament current control and electron beam scanning speed control shown in FIG. 10.

For example, it is preferable to perform the rough setting so that, at all monitor points Py, the measured ion beam current density Imon is similar to the preset ion beam current density Iset, and its distribution is homogenized to some extent. FIGS. 13 and 14A show schematic examples in which such setting is performed. FIG. 13 shows an example in which the measured ion beam current density Imon is set to be slightly smaller than the preset ion beam current density Iset, and FIG. 14A shows an example in which the former is set to be slightly larger than the latter. Any of the settings may be employed.

Roughly speaking, as shown FIG. 13, the peak positions of the measured ion beam current density Imon approximately correspond to the positions of the filaments 1222. In the figure, $AG_1$ indicates a region affected by one electron beam source Gn, and $AG_2$ indicates a region affected by the other electron beam source Gn. However, this figure is simply a schematic figure.

Next, the controlling device 90 supplies the scan signal Sy having an initial waveform to the electron-beam power sources 114 (specifically, their amplifiers 156), to output the scan voltage Vy having the same waveform (step 902). For example, the initial waveform is a triangular waveform. The frequency is, for example, 10 kHz. The frequency is not restricted to this.

The electron beam sources Gn generate the electron beam 138 which is scanned in the Y direction by the initial waveform. By using this and the filaments 122, the plasma 124 is produced in the ion source 100, and the ion beam 50 is extracted (step 903). The ion beam monitor 80 receives the ion beam 50, and measures the ion beam current density Imon (step 904). Examples of this are shown in FIGS. 13 and 14A. Hereinafter, the example of FIG. 14A will be described.

Furthermore, the controlling device 90 performs the following processes such as calculation. On the basis of the measurement data $D_1$ supplied from the ion beam monitor 80, an average value Iave of the ion beam current density Imon in the Y-direction distribution measured by the ion beam monitor 80 is calculated (step 905). This is a certain value.

Next, the average value Iave is compared with the preset ion beam current density Iset, and it is determined whether the both values are substantially equal to each other or not (step 905). If they are substantially equal to each other, the process proceeds step 908, and, if not, the process proceeds step 907. The term of "substantially equal" means that the values are equal to each other, or are within a predetermined small error range. The term may be paraphrased as "approximately equal".

Step 907 is a filament current control subroutine. FIG. 11 shows the contents of the subroutine. In the subroutine, first, it is determined whether the average value Iave is larger than the preset ion beam current density Iset or not (step 920). If larger, the process proceeds step 921, and, if not, the process proceeds step 922.

In step 921, the filament power sources 134 are controlled by the filament current control signal Sf supplied from the controlling device 90, and the filament currents If to be flown through all the filaments 122 of the ion source 100 are uniformly decreased by a predetermined amount (in other words, equally or by the same amount, the same shall apply hereinafter). In step 922, contrary to the above, the filament currents If to be flown through all the filaments 122 are uniformly increased by a predetermined amount. For example, the predetermined amount is about 1% to 2% of the filament currents If at the timing when the rough setting of the filament conditions is ended (step 901). When the predetermined amount is large, the control is rapidly performed, but the possibility that the control is not converged is high. By contrast, when the predetermined amount is small, the control is slow, but the possibility is eliminated. Therefore, the amount may be determined with considering the both cases.

However, the control of steps 900 to 911 including the filament current control subroutine (step 907), and an electron beam scanning speed control subroutine (step 910) which will be described later are not performed in real time in the ion beam implanting process on the substrate 60, but performed at an appropriate timing before the process of the substrate 60, at interruption, or the like. The control speed hardly becomes an issue. Therefore, a control in which importance is given not on speed, but on stability and certainty may be performed. For example, the control may require a time in the unit of minute. This is applicable also to a control shown FIGS. 16 and 17.

Figure 14B:
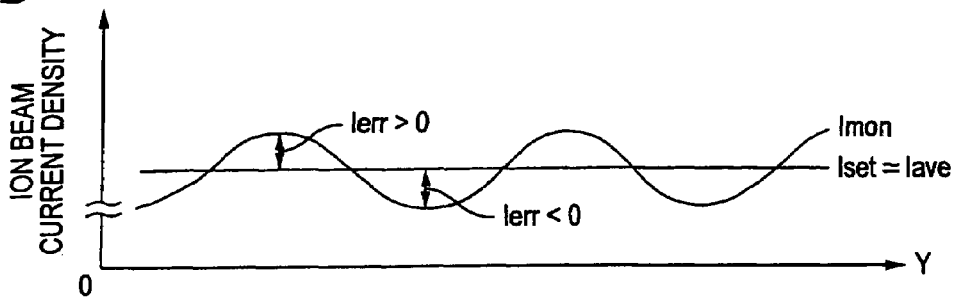

After the filament current control subroutine in step 907, the process returns to step 905, and the above-described control is repeated until the determination in step 906 is YES. This causes the average value Iave to be substantially equal to the preset ion beam current density Iset. FIG. 14B shows a schematic example of this state. Then, the process proceeds to step 908.

In step 908, the error Ierr in the Y-direction distribution which is a difference between the measured ion beam current density Imon in the Y-direction distribution and the preset ion beam current density Iset is calculated in accordance with, for example, the following expression.

$$Ierr = Imon - Iset \quad [\text{Exp. 2}]$$

Next, it is determined whether, at the all monitor points Py on which the ion beam 50 impinges, the size (absolute value) |Ierr| of the error is equal to or smaller than the allowable error ϵ or not (step 909). If even one point where the size is not equal to or smaller than the allowable error exists, the process proceeds to step 910. If not, the process proceeds to step 911.

It is preferred that, as in the embodiment, the determination is performed on the all monitor points Py on which the ion beam 50 impinges. However, the determination on several unimportant monitor points Py may be omitted. It is not required to perform the determination on monitor points Py on which the ion beam 50 does not impinge. Namely, the determination may be performed on substantially all monitor points Py on which the ion beam 50 impinges.

Step 910 is the electron beam scanning speed control subroutine. FIG. 12 shows the contents of the subroutine. In the subroutine, first, a monitor point Py where the size |Ierr| of the error is larger than the allowable error ϵ is determined (in other word, identified, the same shall apply hereinafter), and the sign of the error Ierr at the monitor point Py where the error is large is determined (step 930). As seen from Exp. 2 above, in the example, the case where the measured ion beam current density Imon is larger than the preset ion beam current density Iset is positive, and, the case where the former is smaller than the latter is negative. Also FIG. 14B is referred. The number of monitor points Py which are determined as described above is usually large in an initial stage of the controls, and becomes smaller as the controls of steps 905 to 908 further advance.

Next, the electron beam sources Gn corresponding to the determined monitor points Py, and the scan voltages Vy of the points are determined (step 931). This can be performed by using the above-described correspondence relationships (see Exp. 1 and its description). In the case where only one the electron beam source Gn is used, however, the electron beam source Gn is uniquely determined, and hence it is not necessary to determine the electron beam source Gn.

Next, the waveform of the scan signal Sy is shaped so that the scanning speed of the electron beam 138 at a timing when the error Ierr is the scan voltages Vy corresponding to positive monitor points Py is increased in proportion to the size |Ierr| of the error, and the scanning speed of the electron beam 138 at a timing when the error Ierr is the scan voltages Vy corresponding to negative monitor points Py is decreased in proportion to the size |Ierr| of the error (step 932). As a result, the waveform of the scan signal Sy is changed from the initial triangular wave to a slightly distorted waveform. Briefly speaking, a waveform in which the inclination in a position where the scanning speed is increased or decreased is increased or decreased from the initial waveform or a triangular wave is obtained.

In order to perform more finely the control, it is preferable to set the scanning speed between two points of different scanning speeds, to a scanning speed which is obtained by interpolating the scanning speeds of the two points.

When the scanning speed of the electron beam 138 is increased, the production of the plasma 124 due to the electron beam 138 in the position where the speed is increased is decreased (thinned), and the beam current density of the ion beam 50 extracted therefrom is decreased. When the scanning speed of the electron beam 138 is increased, the production of the plasma 124 due to the electron beam 138 in the position where the speed is decreased is increased (thickened), and the beam current density of the ion beam 50 extracted therefrom is increased.

The increase of the scanning speed of the electron beam 138 means that the time-variation rate dSy/dt of the scan signal Sy and therefore the time-variation rate dVy/dt of the scan voltage Vy are increased, and the decrease of the scanning speed means that the time-variation rate dSy/dt and therefore dVy/dt are decreased.

The proportional constant in the case where the scanning speed of the electron beam 138 is increased or decreased in proportion to the size |Ierr| of the error can be adequately determined. When the proportional constant is increased, the control is rapidly performed, but the possibility that the control is not converged is high. By contrast, when the proportional constant is decreased, the control is slow, but the possibility is eliminated. Therefore, the proportional constant may be determined with considering the both cases.

Figure 14C:
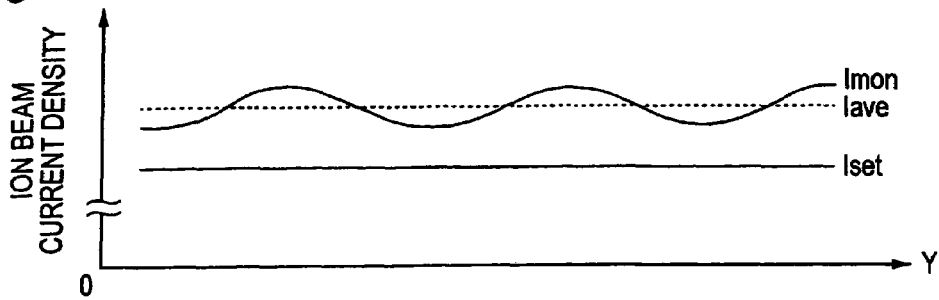

Then, by using the scan signal Sy which has been waveform-shaped as described above, the electron beam 138 generated from the electron beam sources Gn is scanned (step 933). Namely, the electron beam 138 is scanned by using the scan voltage Vy which is obtained by amplifying the waveform-shaped scan signal Sy in the amplifier 156. As a result, the error Ierr is decreased, and also the number of the monitor points Py where the error is larger than the allowable error ϵ is decreased. However, there may arise the case where, in accordance with the waveform shaping, the average value Iave of the measured ion beam current density Imon is changed. FIG. 14C shows a schematic example of this state.

Figure 14D:
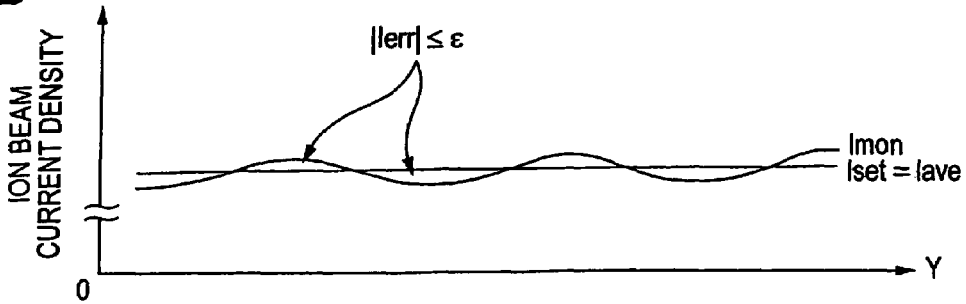

After the electron beam scanning speed control subroutine of step 910, therefore, the process returns to step 905. The above-described control is repeated until the determination in step 909 is YES. As a result, in all (or substantially all) monitor points Py on which the ion beam 50 impinges, the size |Ierr| of the error is equal to or smaller than the allowable error ϵ, and the average value Iave is substantially equal to the preset ion beam current density Iset (see step 906). FIG. 14D shows a schematic example of this state.

If the determination in step 909 is YES, data of the waveform-shaped scan signal Sy, those of the filament current If, and, as required, other data are stored into the controlling device 90 (specifically, the storage device) (step 911). As a result, the control of homogenizing the Y-direction ion beam current density distribution by using the controlling device 90 is ended.

After the homogenizing control is ended, as required, the ion beam 50 is extracted from the ion source 100 by using the stored data, and the ion implantation is performed on the substrate 60.

As described above, according to the ion implanter, the homogenization of the ion beam current density distribution in the Y direction in the implanting position on the substrate 60 can be improved. As a result, the homogenization of the ion implantation on the substrate 60 can be enhanced.

Moreover, the plasma production using the filaments 122, and the homogenization of the ion beam current density distribution due to the control of the plasma density distribution control using the electron-beam power sources Gn are combinedly used. Therefore, ion implantation can be easily performed with illuminating the substrate 60 with an ion beam 50 having a large current and high homogenization. This is applicable also to a next embodiment.

(B) Control of Quantity of Electron Beam

An example of this case will be described mainly with reference to FIGS. 15 to 17. In these figures, the portions which are identical or corresponding to those of the control of (A) above are denoted by the same reference numerals. In the following description, emphasis is placed on differences from the control of (A) above.

Figure 15:
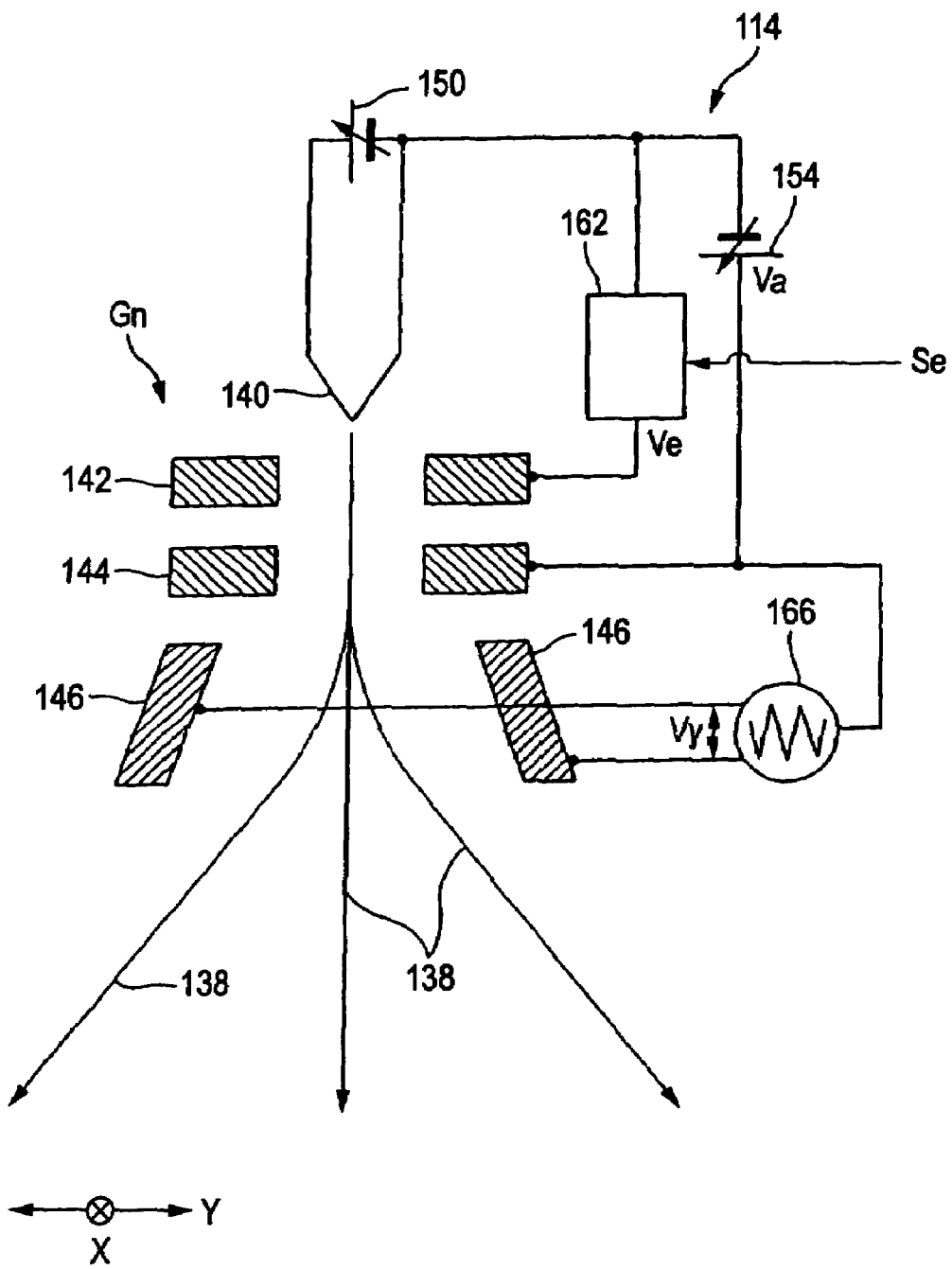
FIG. 15 is a view showing another example of the configuration of the electron beam source and electron-beam power source shown in FIG. 1.

In this case, as the electron-beam power sources 114, the power source shown in FIG. 15 is used. The electron-beam power source 114 has, in place of the DC extraction power source 152, an amplifier 162 which applies the extraction voltage Ve for controlling the generation quantity of the electron beam 138 between the filament 140 and the extraction electrode 142. In the case of the example, the controlling device 90 has a function of supplying an extraction signal Se which is an original of the extraction voltage Ve. The amplifier 162 amplifies (voltage-amplifies) the extraction signal Se supplied from the controlling device 90 to produce (output) the extraction voltage Ve. In place of the amplifier 156, the electron-beam power source has a scan power source 166 which simply outputs the triangular scan voltage Vy.

In this example, namely, the waveform and size of the scan voltage Vy are set constant, and the scan speed of the electron beam 138 generated from the electron beam source Gn is set constant. Preferably, also the anode voltage Va output from the energy control power source 154 is set constant, and the energy of the electron beam 138 is set constant. In the embodiment, therefore, the values are set constant. The frequency of the scan voltage Vy is, for example, 10 kHz. The frequency is not restricted to this.

Figure 16:
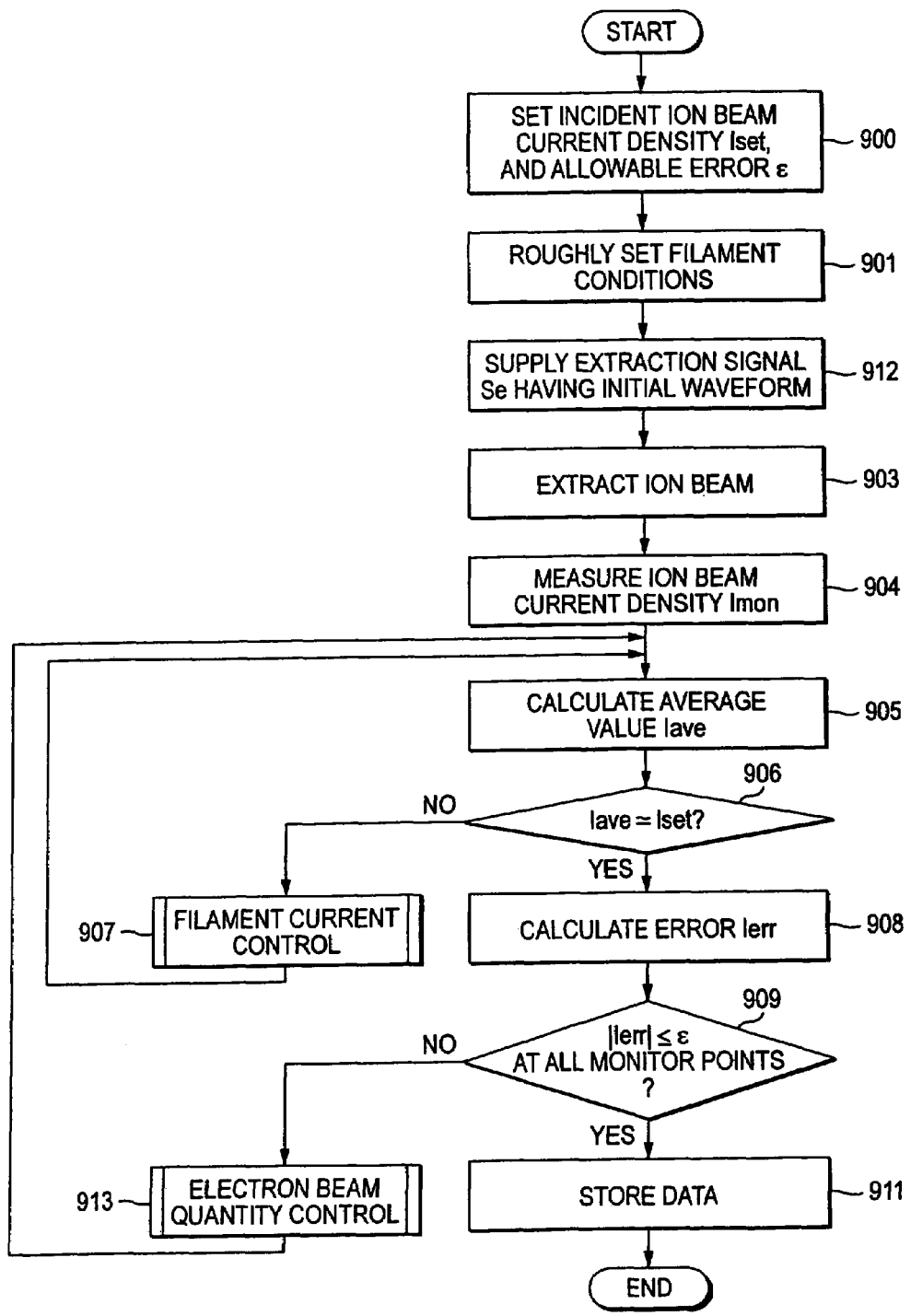
FIG. 16 is a flowchart showing another specific example of contents of the control of homogenizing the Y-direction ion beam current density distribution by using the controlling device shown in FIG. 1.
Figure 17:
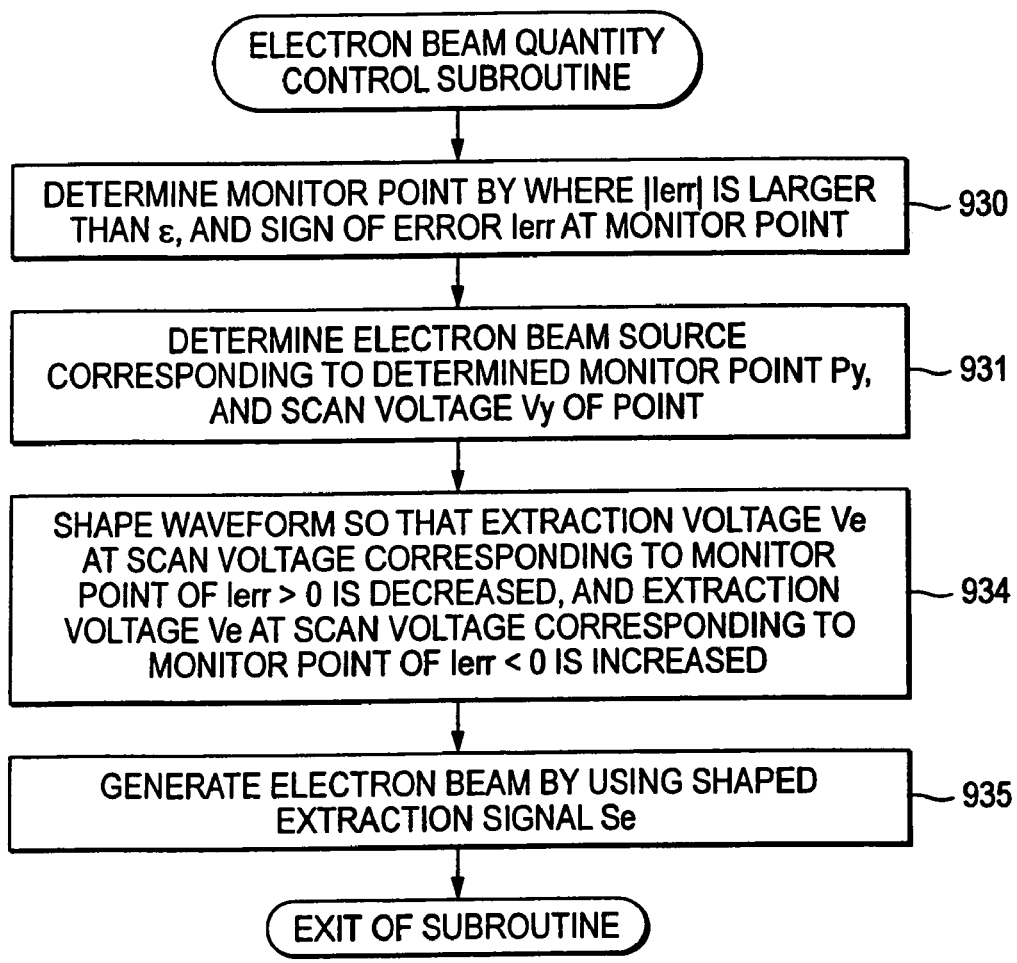
FIG. 17 is a flowchart showing an example of an electron beam quantity control subroutine shown in FIG. 16.

FIGS. 16 and 17 show flowcharts of the control which is performed by using the controlling device 90 in this case. In FIG. 16, step 902 shown in FIG. 10 is replaced with step 912, and step 910 is replaced with step 913. The contents of the filament current control subroutine (step 907) are identical with those shown in FIG. 11, and hence the figure is referred.

In step 912, the controlling device 90 supplies the scan signal Sy having an initial waveform to the electron-beam power sources 114 (specifically, their amplifiers 162), to output the extraction voltage Ve having the same waveform. For example, the initial waveform is a DC voltage having a constant voltage.

Step 913 is an electron beam quantity control subroutine. FIG. 17 shows the contents of the subroutine. Steps 930 and 931 are identical with those shown in FIG. 12, and therefore duplicated description will be omitted.

In step 934 subsequent to step 931, the waveform of the extraction signal Se is shaped so that the extraction voltage Ve at a timing when the error Ierr is the scan voltages Vy corresponding to positive monitor points Py is decreased in proportion to the size |Ierr| of the error, and the extraction voltage Ve at a timing when the error Ierr is the scan voltages Vy corresponding to negative monitor points Py is increased in proportion to the size |Ierr| of the error. As a result, the waveform of the extraction signal Se is changed from the initial constant value to a slightly distorted waveform. Briefly speaking, the voltage value at position in which the electron beam quantity is increased or decreased from the initial constant value wave is obtained.

When the extraction signal Se and therefore the extraction voltage Ve are increased, the electron beam quantity in the position where the signals are increased is increased, the production of the plasma 124 due to the electron beam 138 in the position is increased (thickened), and the beam current density of the ion beam 50 extracted therefrom is increased. When the extraction signal Se and therefore the extraction voltage Ve are decreased, the electron beam quantity in the position where the signals are decreased is decreased, the production of the plasma 124 due to the electron beam 138 in the position is decreased (thinned), and the beam current density of the ion beam 50 extracted therefrom is decreased.

The proportional constant in the case where the extraction voltage Ve is increased or decreased in proportion to the size |Ierr| of the error can be adequately determined. When the proportional constant is increased, the control is rapidly performed, but the possibility that the control is not converged is high. By contrast, when the proportional constant is decreased, the control is slow, but the possibility is eliminated. Therefore, the proportional constant may be determined with considering the both cases.

Then, by using the extraction signal Se which has been waveform-shaped as described above, the electron beam 138 is generated from the electron beam sources Gn (step 935). As a result, the error Ierr is decreased, and also the number of the monitor points where the error is larger than the allowable error ϵ is decreased. In this case, there may arise the case where, in accordance with the waveform shaping, the average value Iave of the measured ion beam current density Imon is changed. A schematic example of this state is identical with that shown in FIG. 14C.

After the electron beam quantity control subroutine of step 913, therefore, the process returns to step 905. The above-described control is repeated until the determination in step 909 is YES. As a result, in all (or substantially all) monitor points Py on which the ion beam 50 impinges, the size |Ierr| of the error is equal to or smaller than the allowable error ε, and the average value Iave is substantially equal to the preset ion beam current density Iset (see step 906). A schematic example of this state is identical with that shown in FIG. 14D.

If the determination in step 909 is YES, data of the waveform-shaped extraction signal Se, those of the filament current If, and, as required, other data are stored into the controlling device 90 (specifically, the storage device) (step 911). As a result, the control of homogenizing the Y-direction ion beam current density distribution by using the controlling device 90 is ended.

Also according to the embodiment, the homogenization of the ion beam current density distribution in the Y direction in the implanting position on the substrate 60 can be improved. As a result, the homogenization of the ion implantation on the substrate 60 can be enhanced.

Figure 18:
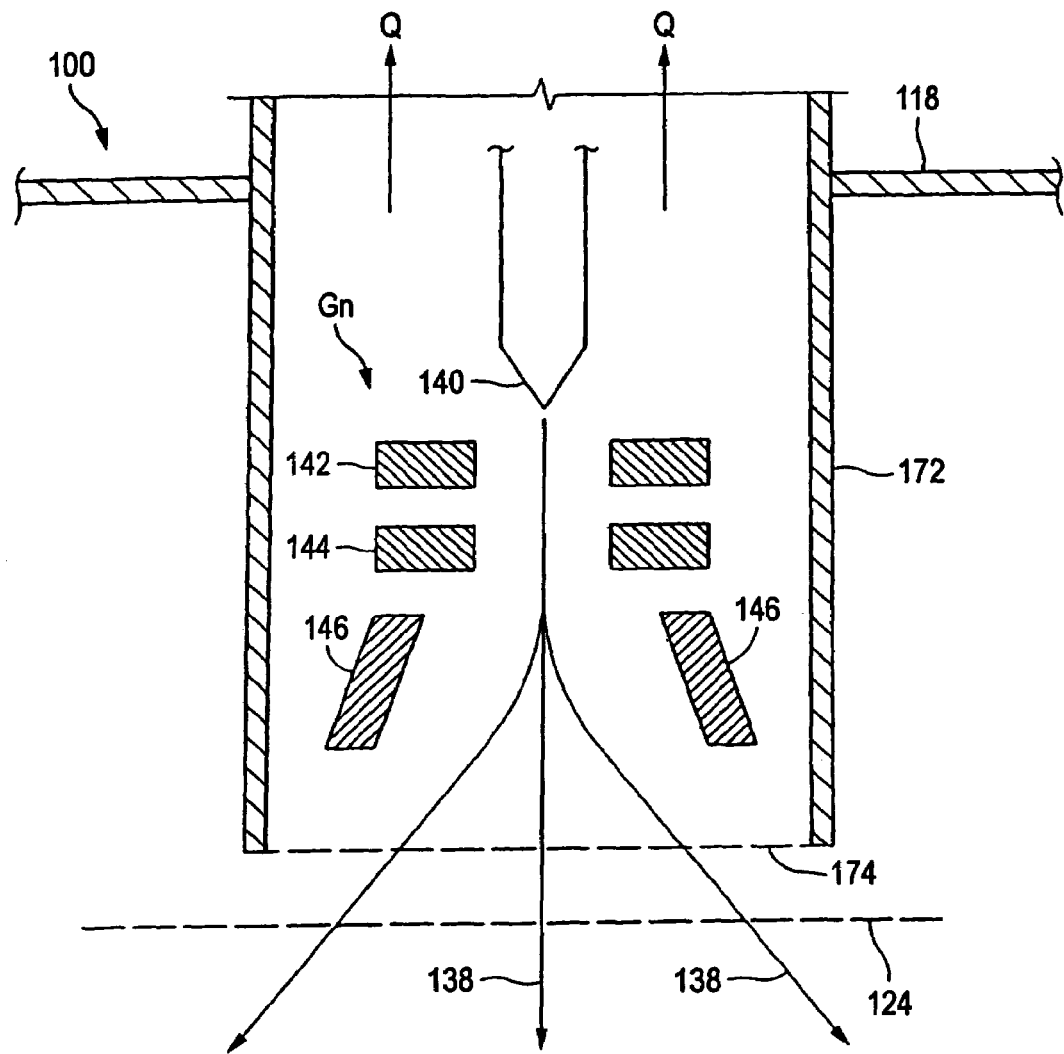
FIG. 18 is a schematic section view showing another example of a manner of placing an electron beam source with respect to a plasma vessel of an ion source.

As in an example shown in FIG. 18, alternatively, the electron beam sources Gn may be housed in a cylinder 172 which is evacuated separately from the interior of the plasma vessel 118, and the electron beam sources Gn may be subjected to differential evacuation as indicated by the arrows Q. According to the configuration, the degree of vacuum of the electron beam sources Gn can be improved, and hence the performance of the electron beam sources Gn can be prevented from being lowered by the gas 120 (see FIG. 4) introduced into the plasma vessel 118.

As in the example shown in FIG. 18, a mesh electrode 174 may be disposed in the vicinity of the front face of the cylinder 172. According to the configuration, the plasma 124 can be shielded by the mesh electrode 174. Therefore, it is possible to prevent the plasma 124 from entering the electron beam sources Gn to lower the performance of the electron beam sources Gn.

Irrespective of the disposition of the cylinder 172 or the mesh electrode 174, the electron beam sources Gn may be placed in the vicinity of but outside the plasma vessel 118, and the electron beam 138 is emitted from the sources into the plasma vessel 118.

As described above, the numbers of the filaments 122, the electron beam sources Gn, and the like are not restricted to those of the embodiments described above, and may be adequately selected in accordance with the required Y-direction dimension $W_Y$ of the ion beam 50, etc. The manners of arranging the filaments 122 and the electron beam sources Gn are not restricted to those of the embodiments described above, and may be adequately determined in accordance with the required Y-direction dimension $W_Y$ of the ion beam 50, etc.

(3) About Analyzing Electromagnet

The analyzing electromagnet 200 will be described. Prior to the description, for comparison, a conventional analyzing electromagnet will be described.

(3-1) Conventional Analyzing Electromagnet

For example, Patent Reference 3 discloses an example of an analyzing electromagnet which is directed to momentum analysis of a ribbon-like ion beam.

Patent Reference 3: JP-A-2004-152557 (Paragraphs 0006 and 0022, FIGS. 1 and 21)

The conventional analyzing electromagnet disclosed in Patent Reference 3 will be described with reference to FIG. 43. In the figure, in order to facilitate the understanding of the shapes of coils 12, 18, a yoke 36 is indicated by two-dot chain lines. The traveling direction of an ion beam 2 is set as the Z direction, and two directions which are substantially orthogonal to each other in a plane that is substantially orthogonal to the Z direction are set as the X and Y directions, respectively. Then, the ribbon-like ion beam 2 which extends in the Y direction incidents on an inlet 24 of the analyzing electromagnet 40, and is emitted from an outlet 26.

Figure 21:
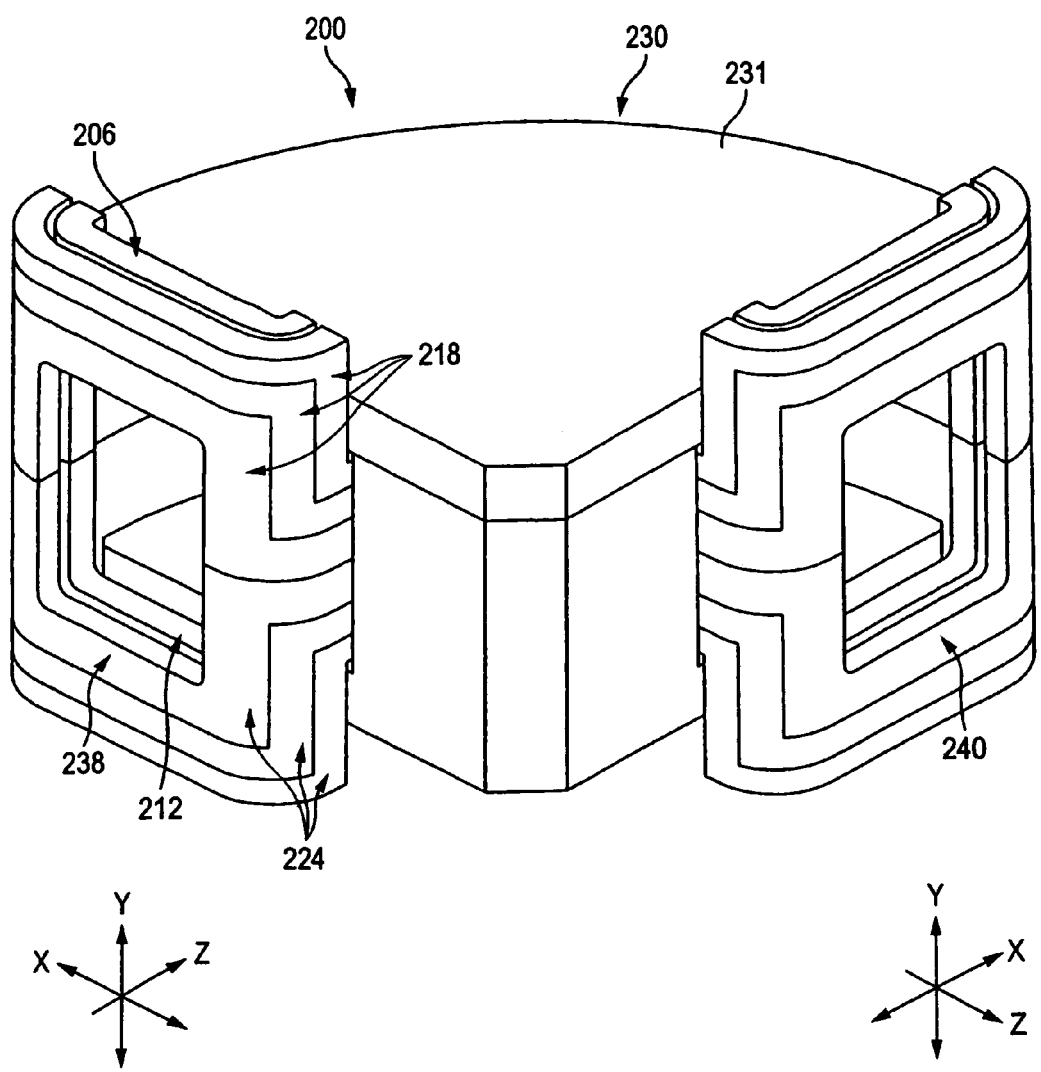
FIG. 21 is a perspective view showing the analyzing electromagnet shown in FIG. 19, with omitting a vacuum vessel.

The analyzing electromagnet 40 has a configuration in which the upper and lower or two coils 12, 18 such as shown in FIG. 1 of Patent Reference 3 are combined with the yoke 36 corresponding to a yoke shown in FIG. 21 of the reference.

The coil 12 is a saddle-shaped coil (in Patent Reference 3, referred to as a banana-shaped coil), and has: one set of body portions (in Patent Reference 3, referred to as coil main portions) 14 that are opposed to each other across a path (beam path) of the ion beam 2; and one set of connecting portions (in Patent Reference 3, referred to as end raised portions) 16 that are obliquely raised so as to avoid the beam path, and connect end portions of the body portions 14 in the Z direction with each other. The connecting portions 16 are obliquely raised in the inlet 24 and the outlet 26 in order that the ion beam 2 is prevented from hitting the portions and a beam passing region is ensured.

Also the coil 18 is a saddle-shaped coil having a similar structure as the coil 12 (however, having a shape which is plane symmetrical to the coil 12), and has one set of body portions 20 and one set of connecting portions 22.

Each of the coils 12, 18 is a multi-turn coil in which a conductor where the periphery is coated by an insulator (coated conductor) is wound many times, and produced by a method in which a coil having a fan-like plan-view shape is bent in the vicinities of the both ends to form the connecting portions 16, 22. As the conductor, usually, a hollow conductor through which a cooling medium (for example, cooling water) can flow is used. In the specification, "insulation" means electrical insulation.

The yoke 36 collectively surrounds the outer sides of the body portions 14, 20 of the coils 12, 18.

The analyzing electromagnet 40 has the following problems.

(A) In the inlet 24 and the outlet 26, the projection distances $L_1$ by which the connecting portions 16, 22 are projected from the yoke 36 in the directions of beam incidence and emission are large. This is caused mainly by the following reasons.

Figure 43:
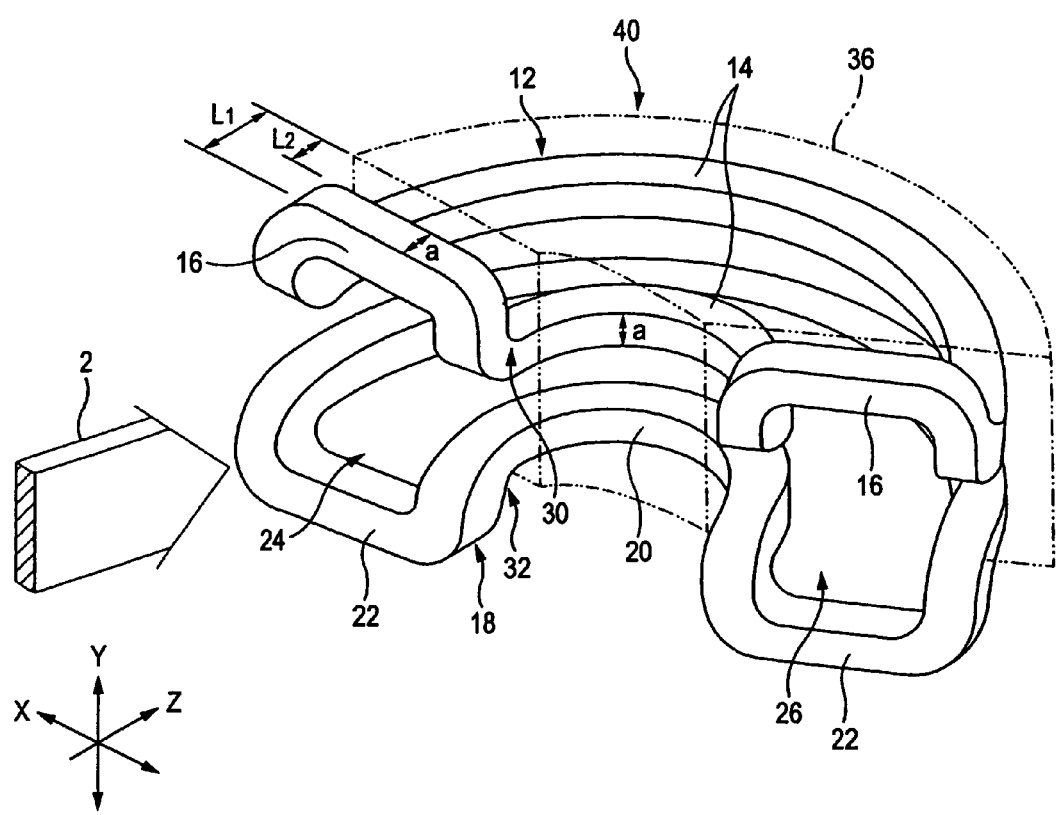
FIG. 43 is a perspective view showing an example of a conventional analyzing electromagnet in which a yoke is indicated by two-dot chain lines in order to facilitate the understanding of the shapes of coils.

(a) In order to allow the ribbon-like ion beam 2 which is elongated in the Y direction to deflect as uniformly as possible, the body portions 14, 20 of the coils 12, 18 must be set so as to be vertically elongated by increasing the dimension a in the Y direction (more vertically elongated than the example shown in FIG. 43). As described above, in the coils 12, 18, a bending process is applied to fan-shaped coils to form the connecting portions 16, 22. Therefore, the dimension a is reflected substantially directly in the projection distance $L_1$. As the dimension a is more increased, consequently, also the projection distance $L_1$ is more increased.

(b) In the coils 12, 18, the connecting portions 16, 22 are formed by applying a bending process to fan-shaped coils as described above. Because of restrictions on the bending process, relatively large bent portions 30, 32 are inevitably formed in the vicinities of borders between the body portions 14, 20 and the connecting portions 16, 22. The existence of the bent portions 30, 32 causes the distance $L_2$ between end portions of the yoke 36 and end portions of the connecting portions 16, 22 to be increased. Because the distance $L_2$ is included in the projection distance $L_1$, the projection distance $L_1$ is increased. Because of restrictions on the bending process, as the dimension a is more increased, the radii curvature of the bent portions 30, 32 must be more increased, therefore the distance $L_2$ and the projection distance $L_1$ are further prolonged.

The projection distance $L_1$ can be indicated by the following expression.

$$L_1 = a + L_2. \quad \text{[Exp. 3]}$$

(c) The connecting portions 16, 22 are obliquely raised. Therefore, this also causes the increasing of the projection distance $L_1$.

As described above, when the projection distances $L_1$ of the connecting portions 16, 22 from the yoke 36 are large, the analyzing electromagnet 40 is accordingly enlarged, and also the area required for installing the analyzing electromagnet 40 is increased. Therefore, also an ion implanter is enlarged, and also the area required for installing the ion implanter is increased. Furthermore, the weight of the analyzing electromagnet 40 is increased. Moreover, the possibility that the magnetic field generated by the connecting portions 16, 22 which are outside the yoke 36 (this magnetic field is also called a fringe field) disturbs the form (the shape and the attitude, the same shall apply hereinafter) of the ion beam 2 is increased.

(B) The power consumption of the coils 12, 18 is large. This is caused mainly by the following reasons.

(a) The connecting portions 16, 22 do not generate a magnetic field for deflecting the ion beam 2. As described above, the projection distances $L_1$ of the connecting portions 16, 22 are large. Therefore, the lengths of the connecting portions 16, 22 are correspondingly increased, and the power consumption is wastefully large in the connecting portions 16, 22. This causes the power consumption of the coils 12, 18 to be increased.

(b) As described above, the coils 12, 18 are multi-turn coils of a coated conductor. Therefore, it is difficult to increase the ratio of the conductor area (i.e., the space factor of the conductor) in the section of the coil 12, 18. Accordingly, the power loss is correspondingly large, and the power consumption is increased. In the case where the coated conductor is a hollow conductor, the space factor of the conductor is more reduced, so that the power loss is further enlarged. Therefore, the power consumption is further increased.

As described above, when the power consumption of the coils 12, 18 is large, the power consumption of the analyzing electromagnet 40 is large, and therefore also that of the ion implanter is large.

The above-discussed problems of the conventional analyzing electromagnet 40 can be solved by the analyzing electromagnet 200 which will be described later. Hereinafter, the whole configuration of the analyzing electromagnet 200, details of the structures of coils, methods of producing the coils, features, controlling method, and other examples of the analyzing electromagnet 200, and the like will be sequentially described.

(3-2) Whole Configuration of Analyzing Electromagnet 200

Figure 19:
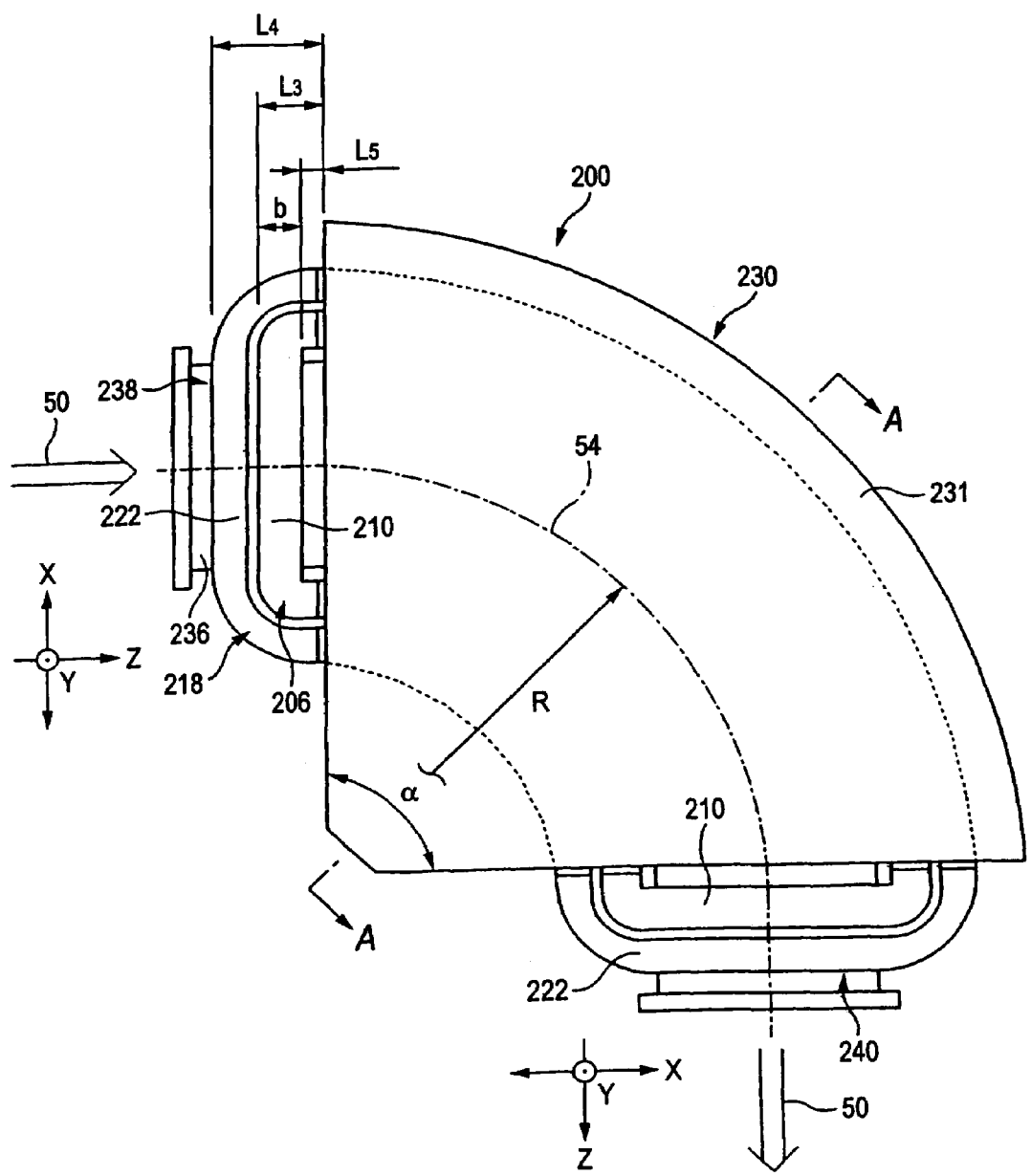
FIG. 19 is a plan view showing an example of an analyzing electromagnet shown in FIG. 1.
Figure 20:
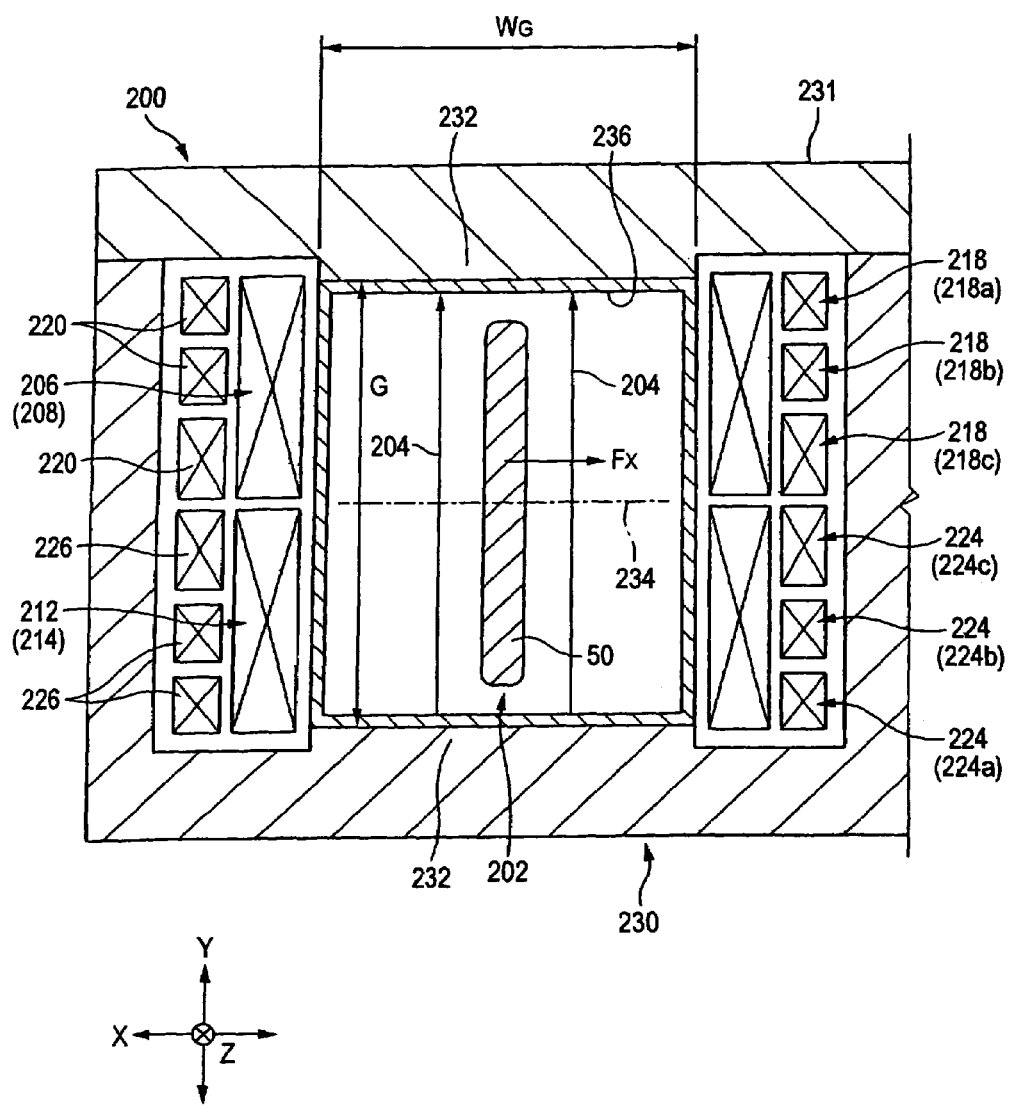
FIG. 20 is a section view taken along the line A-A of FIG. 19.

An example of the analyzing electromagnet 200 is shown in FIGS. 19 to 21, etc. FIG. 21 shows the analyzing electromagnet with omitting the vacuum vessel 236. The analyzing electromagnet 200 is configured so that the ribbon-like ion beam 50 impinges on the electromagnet, a magnetic field along the Y direction is generated in a beam path 202 through which the ion beam 50 passes, and the ion beam 50 is bent in the X direction to perform momentum analysis. The magnetic field is diagrammatically shown by magnetic force lines 204 in FIG. 20 and the like. When the ion beam 50 impinges on the analyzing electromagnet 200, the ion beam 50 in traveling is subjected by the magnetic field to the Lorentz force $F_X$ which is rightward directed as viewed in the traveling direction Z, thereby rightward deflected. As a result, the momentum analysis is performed. The center orbit 54 of the ion beam 50 is indicated by the one-dot chain line in FIG. 19, and its radius of curvature is shown by R. The angle (deflection angle) at which the ion beam 50 is deflected by the analyzing electromagnet 200 is indicated by $\alpha$.

For example, the radius of curvature R is 300 to 1,500 mm, and the deflection angle $\alpha$ is 60 to 90 deg. FIG. 19 exemplarily shows the case where the deflection angle $\alpha$ is 90 deg.

Figure 22:
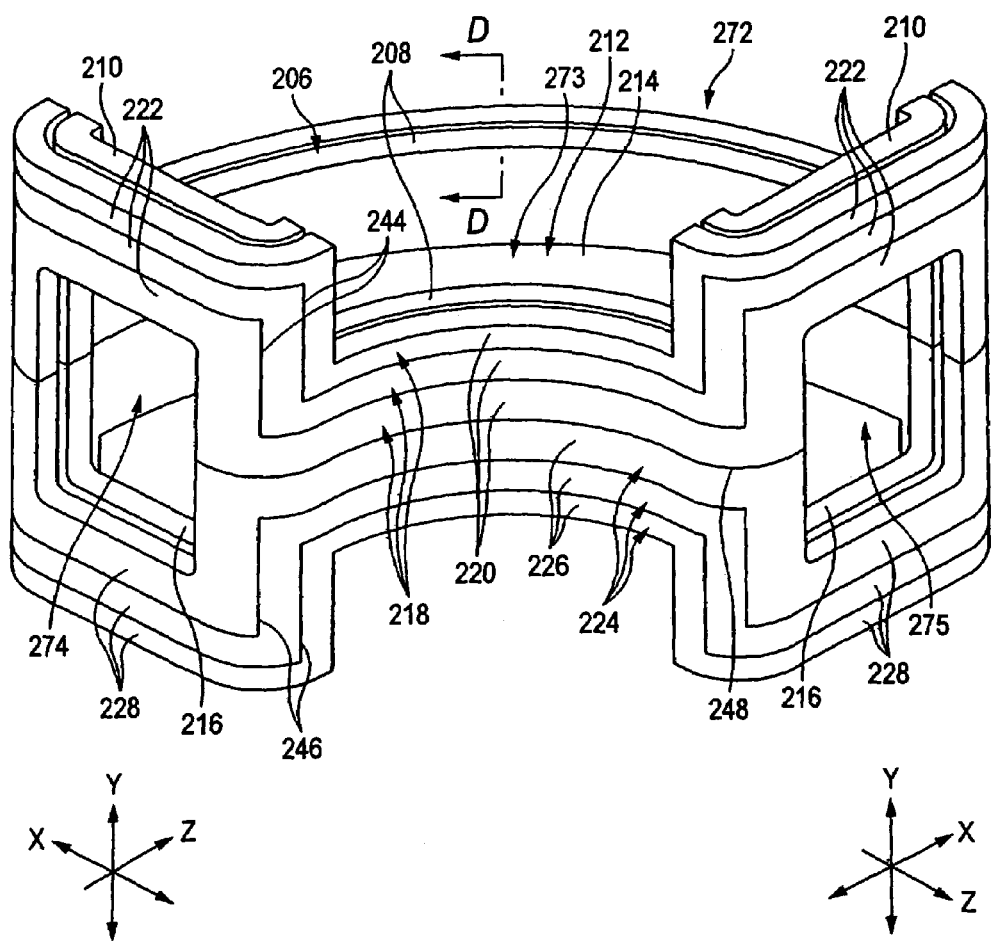
FIG. 22 is a perspective view showing the analyzing electromagnet shown in FIG. 19.

Also referring to FIG. 22, the analyzing electromagnet 200 comprises a first inner coil 206, a second inner coil 212, one or more (in the embodiment, three) first outer coils 218, one or more (in the embodiment, three) second outer coils 224, a yoke 230, and one set of magnetic poles 232. The beam path 202 is surrounded by the vacuum vessel 236 made a nonmagnetic material, and maintained to a vacuum atmosphere. The vacuum vessel 236 is also called an analyzer tube.

The first and second inner coils 206, 212 are extracted and shown in FIG. 23. The coils are understood more easily with reference to the figure.

In this example, the coils 206, 212, 218, 224 have a shape which is substantially plane-symmetrical in the Y direction about a symmetry plane 234 (see FIG. 20 and the like) that passes the center in the Y direction of the beam path 202, and that is parallel to the XZ plane. A coil 320 (see FIGS. 37 and 39 and the like), first coil 326, and second coil 328 (see FIG. 40) which will be described later are configured in a similar manner. When such plane symmetry configuration is employed, a magnetic field with high symmetry in the Y direction can be easily generated in the beam path 202. This contributes to the suppression of the disturbance of the form of the ion beam 50 at emission from the analyzing electromagnet 200.

Figure 24:
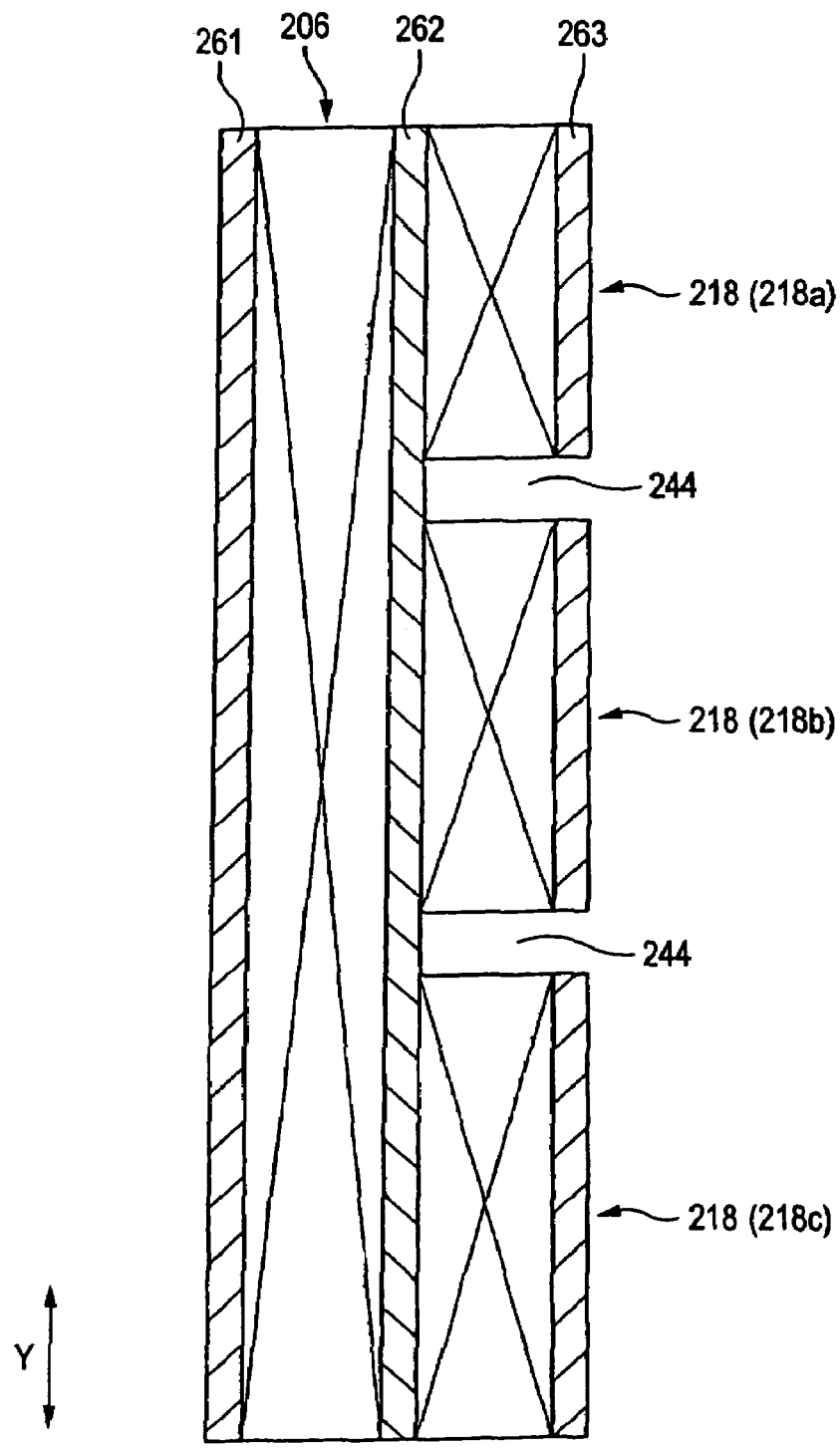
FIG. 24 is a schematic view enlargedly showing sections of the first inner and outer coils taken along the line D-D of FIG. 22.
Figure 28:
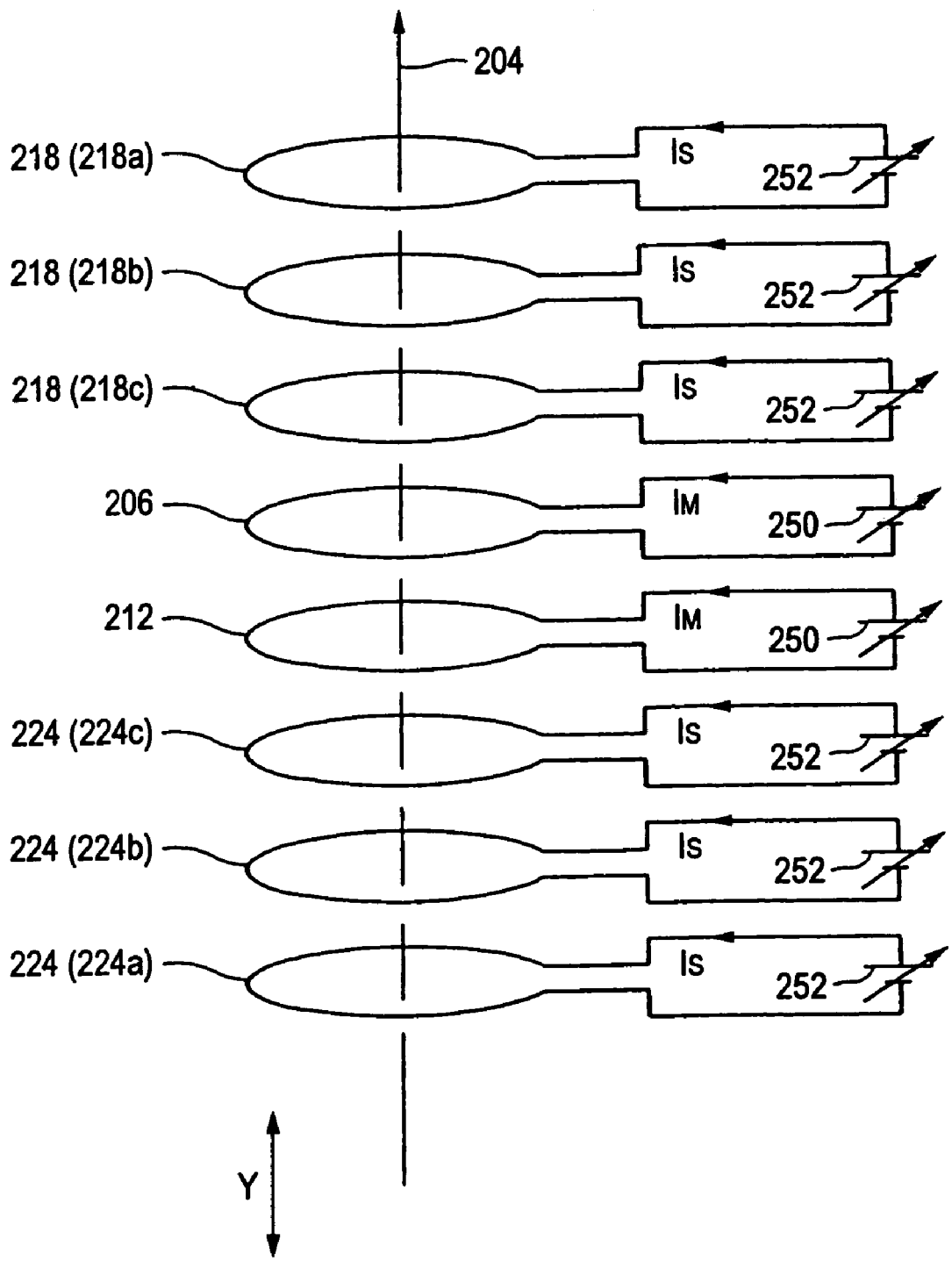
FIG. 28 is a view showing an example of a power source configuration for coils of the analyzing electromagnet shown in FIG. 19.

Hereinafter, when the plural first outer coils 218 and plural second outer coils 224 are to be distinguished from one another, as shown in FIGS. 20, 24, 28, and the like, the first outer coils 218 are denoted as first outer coils 218a, 218b, 218c with starting from the upper side in the Y direction, and the second outer coils 224 are denoted as second outer coils 224s, 224b, 224c with starting from the lower side in the Y direction because the second outer coils are plane-symmetrical with respect to the first outer coils 218 as described above.

The coil 206 is underlined in the drawings, it indicates that such a numeral indicates the whole of the component such as the coil.

Figure 27:
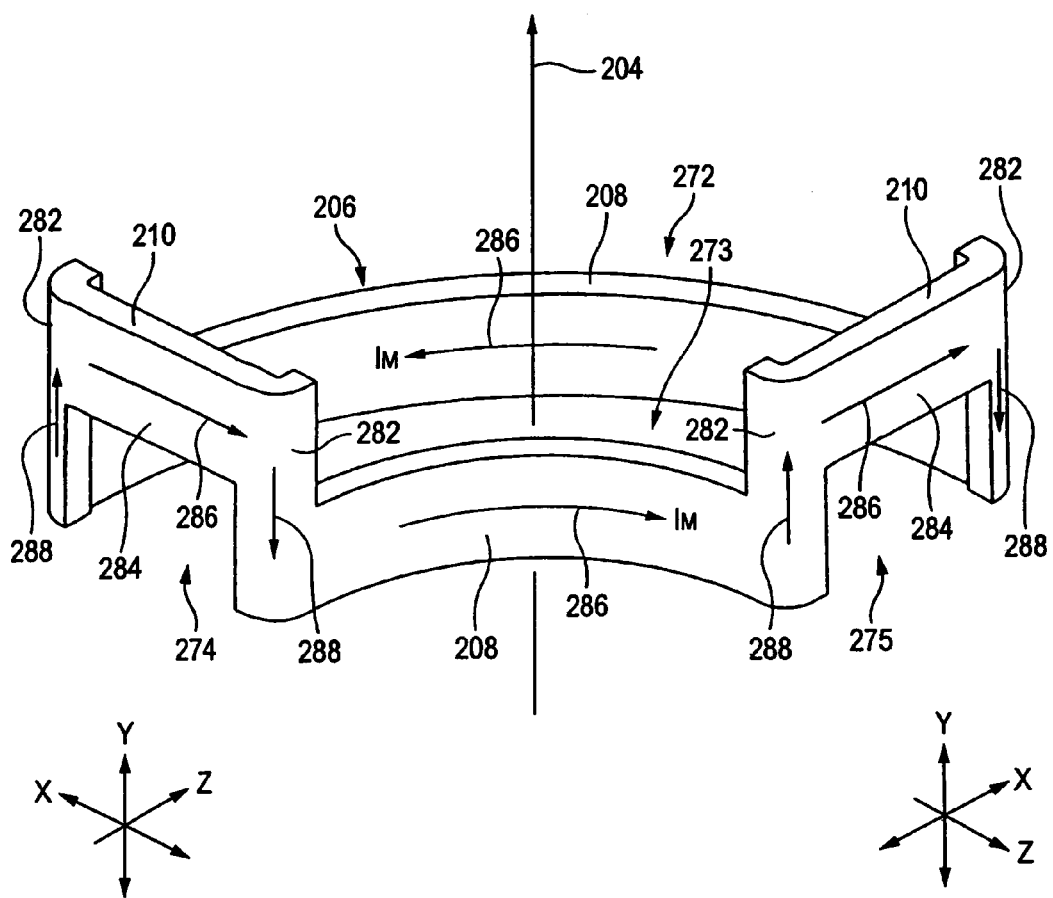
FIG. 27 is a perspective view showing a first inner coil shown in FIG. 23.

Referring mainly to FIGS. 23 and 27, the first inner coil 206 is a saddle-shaped coil having: one set of body portions 208 that are opposed to each other in the X direction across the beam path 202, and that cover about a half or more (in other words, substantially a half or more) of one side (in the embodiment, the upper side) of the ion beam 50 in the Y direction; and one set of connecting portions 210 that connect end portions of the body portions 208 in the Z direction (in other words, the end portion on the side of an inlet 238 of the analyzing electromagnet 200, and that on the side of an outlet 240, this is applicable also to the other coils) with each other, while avoiding the beam path 202. The first inner coil cooperates with the second inner coil 212 to generate a main magnetic field which bends the ion beam 50 in the X direction. The main magnetic field is a magnetic field by which the ion beam 50 is mainly bent at a substantially predetermined radius of curvature R.

The first inner coil 206 is called a saddle-shaped coil because, when viewed as a whole, the coil has a saddle-like shape. The same shall apply to the other coils 212, 218, 224, and the coils 326, 328 which will be described later.

In order to prevent the ion beam 50 from impinging on the connecting portions 210, and to reduce influences exerted on the ion beam 50 by magnetic fields generated by the portions, the connecting portions are separated from the beam path 202 toward the upper side in the Y direction. For the same purpose as the above, connecting portions of the other coils are separated from the beam path 202 toward the upper or lower side in the Y direction.

Referring mainly to FIG. 23, the second inner coil 212 is a saddle-shaped coil having: one set of body portions 214 that are opposed to each other in the X direction across the beam path 202, and that cover about a half or more (in other words, substantially a half or more) of the other side (in the embodiment, the lower side) of the ion beam 50 in the Y direction; and one set of connecting portions 216 that connect end portions of the body portions 214 in the Z direction with each other, while avoiding the beam path 202. The second inner coil is disposed overlappingly with the first inner coil 206 in the Y direction, and cooperates with the first inner coil 206 to generate a main magnetic field which bends the ion beam 50 in the X direction. Namely, the second inner coil 212 generates magnetic force lines 204 which are identical in direction with those of the first inner coil 206.

The second inner coil 212 has similar dimensions and structure as the first inner coil 206. Usually, also the number of turns of the conductor (specifically, the conductor sheet 268, see FIG. 25 and the like) is equal to that of the first inner coil 206. As described above, however, the second inner coil has a plane-symmetrical shape about the symmetry plane 234 with respect to the first inner coil 206. The connecting portions 216 are disposed on the opposite side (i.e., the lower side) in the Y direction with respect to the connecting portions 210 across the beam path 202.

Although indicated by a line in FIG. 23, a slight (for example, about 20 mm) gap 242 is formed between the first inner coil 206 and the second inner coil 212. In the gap, cooling plates 312 (see FIG. 34) which are two in total, and which will be described later can be disposed, or one cooling plate is on the side of the first inner coil 206, and one cooling plate is on the side of the second inner coil 212.

Referring mainly to FIG. 22, each of the first outer coils 218 is a saddle-shaped coil having: one set of body portions 220 that are outside the first inner coil 206, and that are opposed to each other in the X direction across the beam path 202; and one set of connecting portions 222 that connect end portions of the body portions 220 in the Z direction with each other, while avoiding the beam path 202. The first outer coils generate a sub-magnetic field which assists or corrects the main magnetic field. The first outer coils 218 are disposed overlappingly with each other in the Y direction.

Specifically, lateral portions (portions corresponding to a lateral portion 284 shown in FIG. 27) of the body portions 220 and connecting portions 222 of each first outer coil 218 are disposed overlappingly with each other in the Y direction. Although, strictly speaking, it is difficult to say that vertical portions (portions corresponding to a vertical portion 282 shown in FIG. 27) of the connecting portions 222 are overlappingly disposed as described above, it can be said that, when viewed as a whole, the first outer coils 218 are disposed overlappingly with each other in the Y direction. The second outer coils 224 are configured in a similar manner.

The first outer coils 218 have a substantially similar structure as the first inner coil 206. However, the dimension in the Y direction is smaller than that of the first inner coil 206, and also the number of turns of the conductor is usually smaller than that of the first inner coil 206. The first outer coils 218 have the same number of turns of the conductor (specifically, the conductor sheet 269, see FIG. 25 and the like). In the embodiment, the first outer coils 218 have different Y-direction dimensions. Alternatively, they have the same Y-direction dimension. The second outer coils 224 are configured in a similar manner.

For example, the Y-direction dimensions of the body portions and connecting portions in the first and second inner coils 206, 212, are about 230 mm, those in the first and second outer coils 218a, 224a are about 50 mm, those in the first and second outer coils 218b, 224b are about 60 mm, and those in the first and second outer coils 218c, 224c are about 100 mm.

Although indicated by lines in FIG. 22, slight gaps 244, 246, 248 are formed respectively between the first outer coils 218, between the second outer coils 224, and between the lowest first outer coil 218 (218c) and the uppermost second outer coil 224 (224c) (see also FIG. 24). In the gaps, the cooling plates 312 (see FIG. 34) which will be described later can be disposed. For example, the dimensions of the gaps 244, 246 are about 10 mm, and the dimension of the gap 248 corresponds to that of the gap 242 or is about 20 mm. The gaps 244, 246 are disposed in the whole periphery along the respective outer coils 218, 224.

The first outer coils 218 may generate a magnetic field of the same direction as or opposite to that generated by the first and second inner coils 206, 212. Alternatively, the direction of the magnetic field may be inverted by a control. The second outer coils 224 are configured in a similar manner. A part of the magnetic force lines (magnetic field) generated by the body portions 220 of the first outer coils 218 spreads toward the beam path 202 (in other words, leaks), so that the main magnetic field is affected. Therefore, the first outer coils 218 can generate the sub-magnetic field which assists or corrects the main magnetic field. In this case, each of the first outer coils 218 exerts an effect of assisting or correcting the magnetic field in a region in the vicinity of the inner side of the coil. The second outer coils 224 are configured in a similar manner.

Referring mainly to FIG. 22, each of the second outer coils 224 is a saddle-shaped coil having: one set of body portions 226 that are outside the second inner coil 212, and that are opposed to each other in the X direction across the beam path 202; and one set of connecting portions 228 that connect end portions of the body portions 226 in the Z direction with each other, while avoiding the beam path 202. The second outer coils generate a sub-magnetic field which assists or corrects the main magnetic field. The second outer coils 224 are disposed overlappingly with each other in the Y direction, and with the first outer coils 218 in the Y direction.

The second outer coils 214 have a substantially similar structure as the second inner coil 212. However, the dimension in the Y direction is smaller than that of the second inner coil 212, and also the number of turns of the conductor is usually smaller than that of the second inner coil 212. The numbers of turns of the conductor (specifically, the conductor sheet) and Y-direction dimensions of the second outer coils 224 are as described above.

An example of the number of turns of each conductor will be described. The numbers of turns of the first and second inner coils 206, 212 are about 110 turns, and those of the first and second outer coils 218, 224 are about 85 turns.

A substantially whole of each of the body portions 208, 214, 220, 226 of the coils is positioned in the yoke 230, and hence it can be said that the portion is a portion which generates a desired magnetic field (the main magnetic field or the sub-magnetic field) in the beam path 202. A body portion 322 of the coil 320 which will be described later is configured in a similar manner.

It can be said that the connecting portions 210, 216, 222, 228 of the coils are portions which electrically connect the end portions of the respective one set of body portions in the Z direction with each other, and which cooperate with the body portions to form a loop-like conduction path. Connecting portions 324, 325 of the coil 320 which will be described later are configured in a similar manner.

FIG. 20 is a longitudinal section view taken along the line A-A of FIG. 19, and therefore shows the body portions 208, 214, 220, 226 of the coils 206, 212, 218, 224. Also FIGS. 39 to 41 which will be described later show the body portions of the coils.

The yoke 230 is made of a ferromagnetic material, and collectively surrounds the outer sides of the body portions 208, 214, 220, 226 of the coils 206, 212, 218, 224. The thus configured yoke 230 also exerts an effect that a leakage magnetic field to the outside can be reduced. The yoke 230 has a so-called fan-like plan-view shape as shown in FIG. 19. The section shape (a section along the XY plane) of the yoke 230 is a rectangular frame-like shape. The thus configured yoke 230 is also called a window-frame type yoke.

In the embodiment, an upper yoke 231 constituting the yoke 230 is detachable. The manner of using the upper yoke 231 will be described later.

The one set of magnetic poles 232 are made of a ferromagnetic material, and inward protruded by, for example, about 15 mm from the yoke 230 so as to be opposed to each other in the Y direction across the beam path 202. The plan-view shape of each magnetic pole 232 is an arcuate shape which extends along the center orbit 54 of the ion beam 50 shown in FIG. 19. This shape is also called a fan-like shape. The gap length G between the magnetic poles 232 is somewhat (for example, by 100 to 150 mm) larger than the dimension $W_Y$ in the Y direction of the ion beam 50. The magnetic poles 232 are not essential. When the magnetic poles are disposed, however, the magnetic force lines 204 can be easily concentrated in the gap between the magnetic poles 232, and therefore it is facilitated to generate a magnetic field having a high magnetic flux density in the beam path 202.

For example, the gap length G between the magnetic poles 232 has a size which is equal to or larger than ½ of the radius of curvature R. When the radius of curvature R is 800 mm, specifically, the gap length G is, for example, 500 mm. Usually, the gap length G is larger than the width $W_G$ of the magnetic poles 232. Namely, $G \geq W_G$. According to such dimensional relationships, the magnetic poles 232 and the yoke 230 can be prevented from being unnecessarily enlarged.

Figure 25:
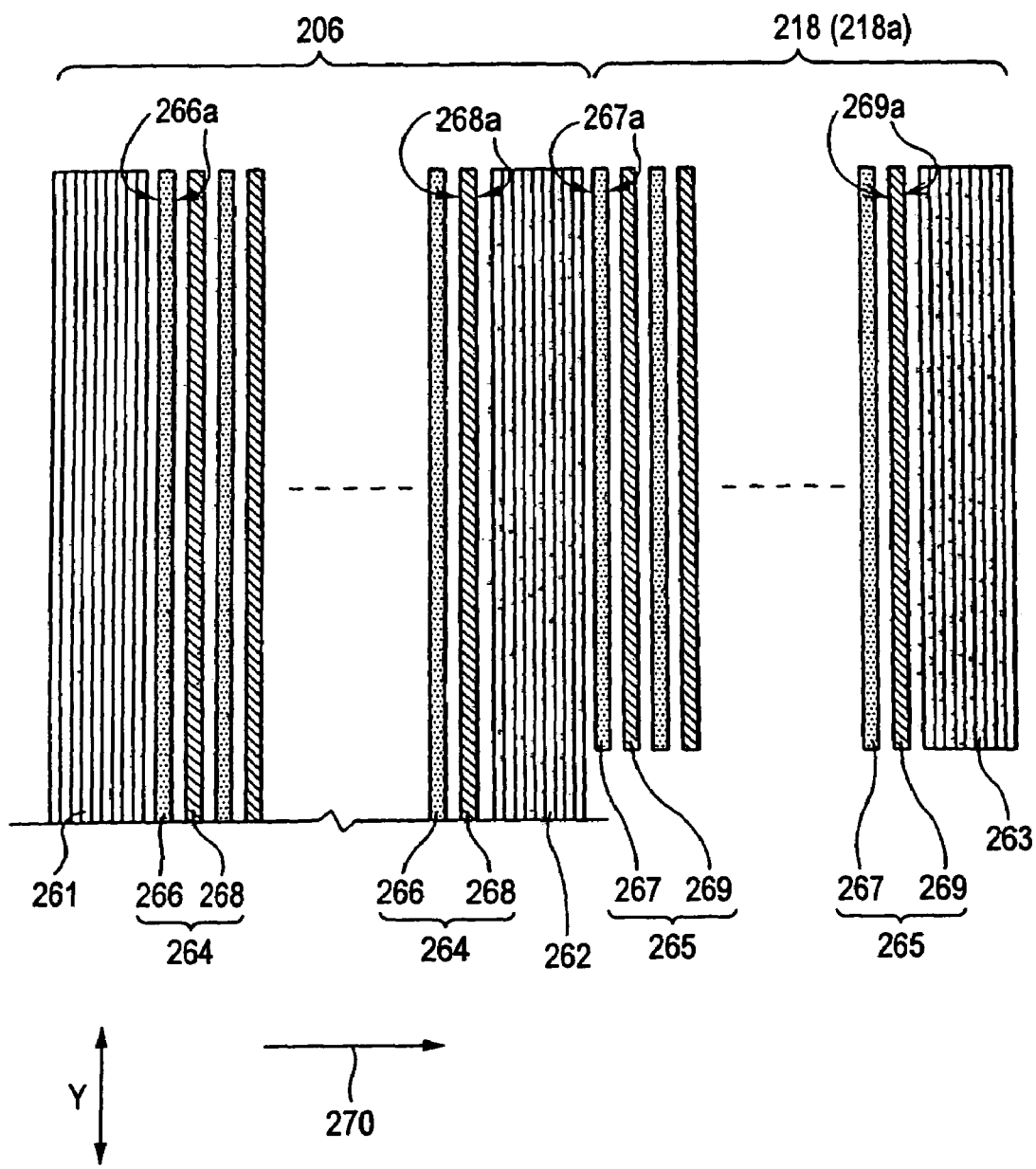
FIG. 25 is a section view explodedly showing the first inner coil and the uppermost first outer coil shown in FIG. 24.

In FIGS. 20 to 22, gaps seem to exist between the first inner and outer coils 206, 218, and between the second inner and outer coils 212, 224. In the embodiment, a stacked insulator 262 shown in FIGS. 24 and 25 is interposed in the gaps.

(3-3) Structures of Coils, and the Like

Next, structures of the coils, and the like will be described in detail. FIG. 24 is a schematic view enlargedly showing sections of the first inner and outer coils taken along the line D-D of FIG. 22, and FIG. 25 is a section view explodedly showing the first inner coil and the uppermost first outer coil shown in FIG. 24.

The first inner and outer coils 206, 218 have a structure where notched portions 272 to 275 (see FIG. 22) are disposed in a fan-shaped cylindrical stacked coil 290 (see FIG. 29) while leaving the body portions 208, 220 and the connecting portions 210, 222. In the fan-shaped cylindrical stacked coil, a lamination (a set 264) of an insulation sheet 266 in which the principal face 266a extends along the Y direction, and a conductor sheet 268 in which the principal face 268a extends along the Y direction is stacked with being wound at several turns on the outer peripheral face of a first stacked insulator 261 (stacked in the direction of the arrow 270 intersecting with the Y direction, the same shall apply hereinafter), the second stacked insulator 262 is formed on the outer peripheral face of the lamination, a lamination (a set 265) of the insulation sheet 267 in which the principal face 267a extends along the Y direction, and the conductor sheet 269 in which the principal face 269a extends along the Y direction is stacked with being wound at several turns on the outer peripheral face of the insulator, and a third stacked insulator 263 is formed on the outside of the lamination.

In order to facilitate the understanding of the notched portions 272 to 275, the notched portions 272 to 275 of the first inner coil 206 are shown in FIG. 27. Similar notched portions 272 to 275 are disposed also in the first outer coils 218.

The yoke 230 is fitted into the two notched portions 272, 273 which are positioned in outer and inner directions of the radius of curvature R. Namely, they have a shape corresponding to the shape of the yoke 230. Notched portions 276 to 279 of the coil 320 which will be described later are configured in a similar manner. The two notched portions 274, 275 on the side of the traveling direction Z of the ion beam 50 form upper halves of the inlet 238 and the outlet 240, respectively.

The second stacked insulator 262 may be deemed to constitute the first inner coil 206 (FIG. 25 illustrates this case), or may be deemed to constitute the first outer coil 218, or may be deemed to be shared by the coils 206, 218.

Figure 29:
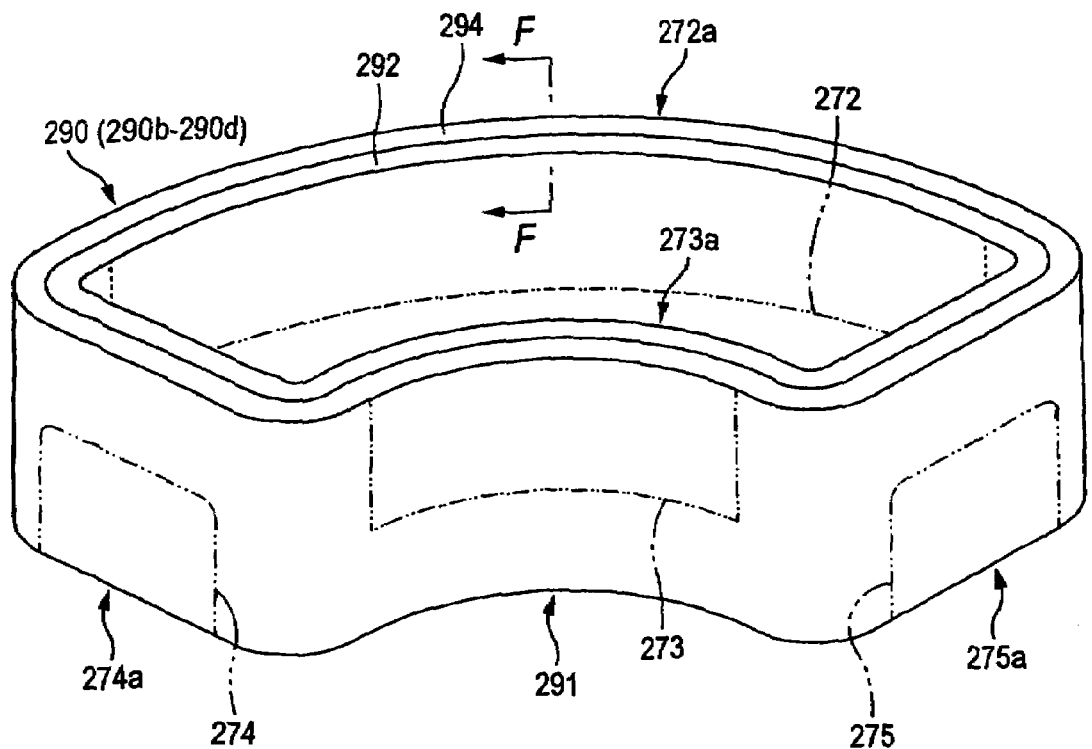
FIG. 29 is a perspective view showing an example of a stacked coil which is an original of the first and second inner coils shown in FIG. 22.
Figure 30:
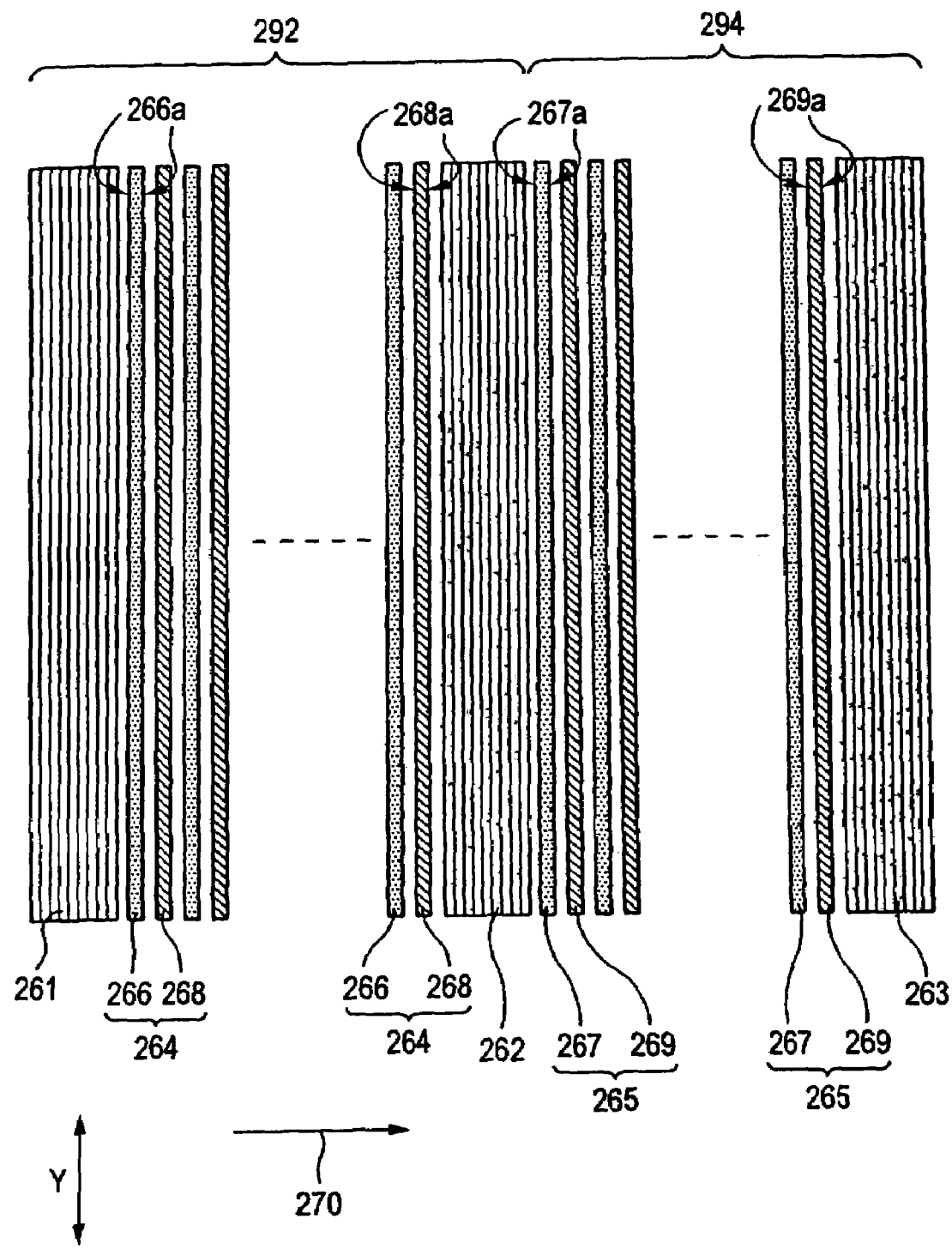
FIG. 30 is a view explodedly showing a section of the inner and outer coils, along the line F-F of FIG. 29.
Figure 31:
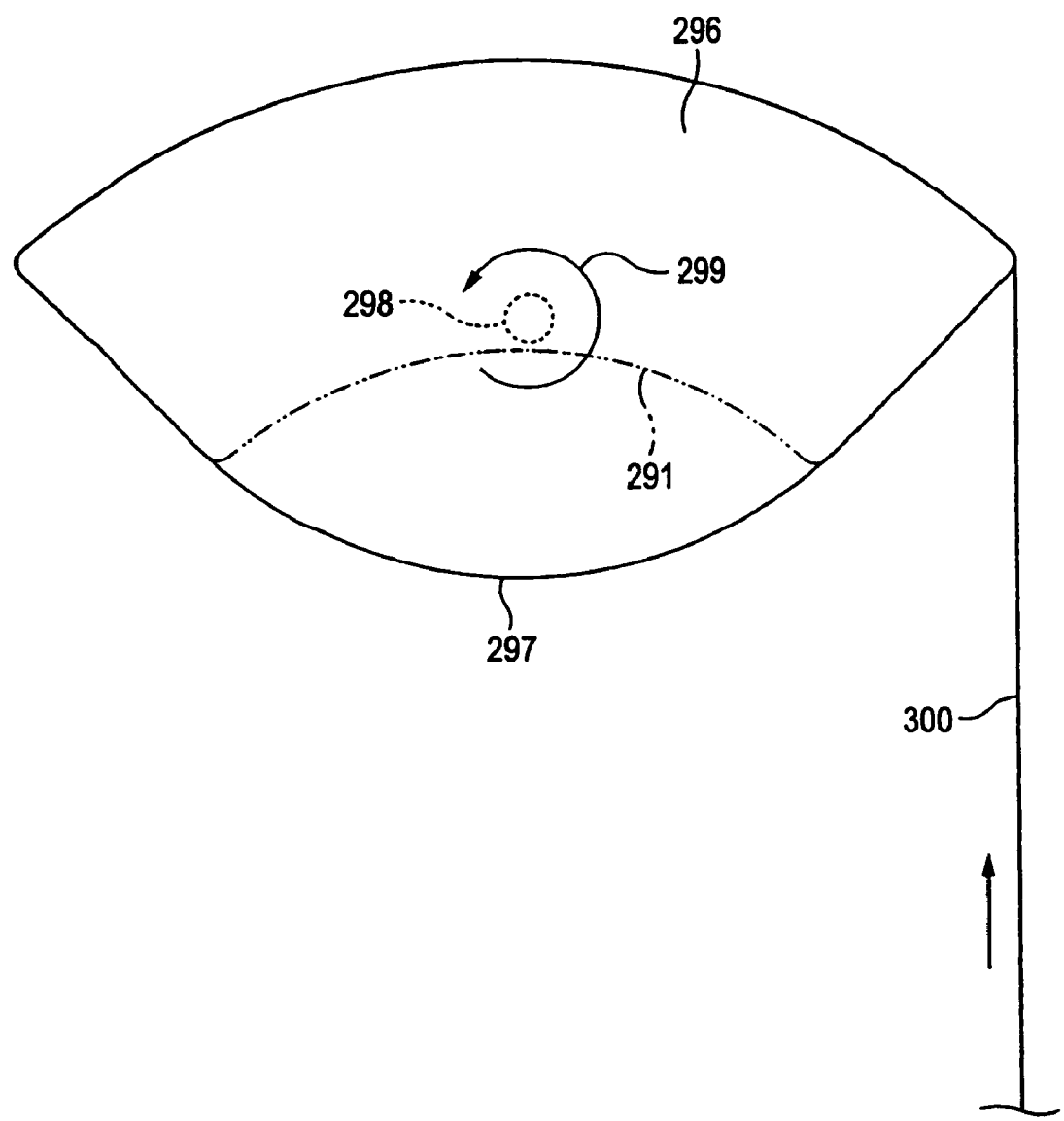
FIG. 31 is plan view showing an example of a manner of winding a prepreg sheet by using a mandrel.

FIG. 30 shows the section structure of the stacked coil 290 shown in FIG. 29. As shown in FIG. 30, the stacked coil is configured by inner and outer coils 292, 294 having the same section structure as that of FIG. 25. Also in this case, the second stacked insulator 262 may be deemed to constitute the inner coil 292 (FIG. 30 illustrates this case), or may be deemed to constitute the outer coil 294, or may be deemed to be shared by the coils 292, 294.

In the stacked coil 290, portions 272a to 275a respectively corresponding to the notched portions 272 to 275 are notched and removed by a cutting process or the like to form the notched portions 272 to 275. Then, the inner coil 292 is configured as the first inner coil 206, and the outer coil 294 is configured as the first outer coil 218.

Furthermore, the embodiment has a structure where, in order to divide the first outer coil 218 into three portions (three steps), the gaps 244 are disposed in the outer coil 294 of the stacked coil 290 by a cutting process or the like.

Each of the stacked insulators 261, 262, 263 of the stacked coil 290 is formed by, for example, winding in multiple turns a prepreg sheet. A prepreg sheet 300 in FIG. 16 is the prepreg sheet. A prepreg sheet is a sheet in which a support member having insulative and heat resistant properties is impregnated with an insulative resin to be processed into a semi-hardened state.

The support member is configured by, for example, glass fibers or carbon fibers. The resin is configured by, for example, an epoxy resin or a polyimide resin. The stacked insulators 261 to 263 which are formed with using such a prepreg sheet may be called fiber-reinforced plastic (FRP). The thickness of the stacked insulators 261 to 263 may be adequately selected in accordance with the strength required as a structural member.

Each of the insulation sheets 266, 267 is a sheet configured by, for example, Nomex (registered trademark), Lumilar (registered trademark), or Kapton (registered trademark), or another insulation sheet. The thickness of the insulation sheets 266, 267 may be adequately selected in accordance with the required insulation strength and the like. For example, the thickness is about 75 μm, or may be smaller than this value.

Each of the conductor sheets 268, 269 is configured by, for example, a copper sheet or an aluminum sheet. The thickness may be adequately selected in accordance with the current to be passed. For example, in the case of a copper sheet, the thickness is about 0.4 mm, and, in the case of an aluminum sheet, the thickness is about 0.5 mm. Their width in a direction corresponding to the Y direction may be adequately selected in accordance with the required Y-direction dimension of the coil, and is, for example, 230 mm (for example, the width before a process which will be described later is about 234 mm). Also the widths of the stacked insulators 261 to 263 and the insulation sheets 266, 267 may be set in accordance with this value.

The insulation sheet 266 and the conductor sheet 268 may be overlapped in the manner opposite to that of FIG. 25 as described below. The conductor sheet 268 may be disposed inside (the left side of FIG. 25, i.e., on the side of the stacked insulator 261) of the first inner coil 206, and the insulation sheet 266 may be disposed overlappingly with the outside. As required, insulation sheets 266 may be disposed overlappingly with the both sides of the conductor sheet 268, respectively. The insulation sheet 267 and conductor sheet 269 of the first outer coils 218 are configured in a similar manner.

Figure 26:
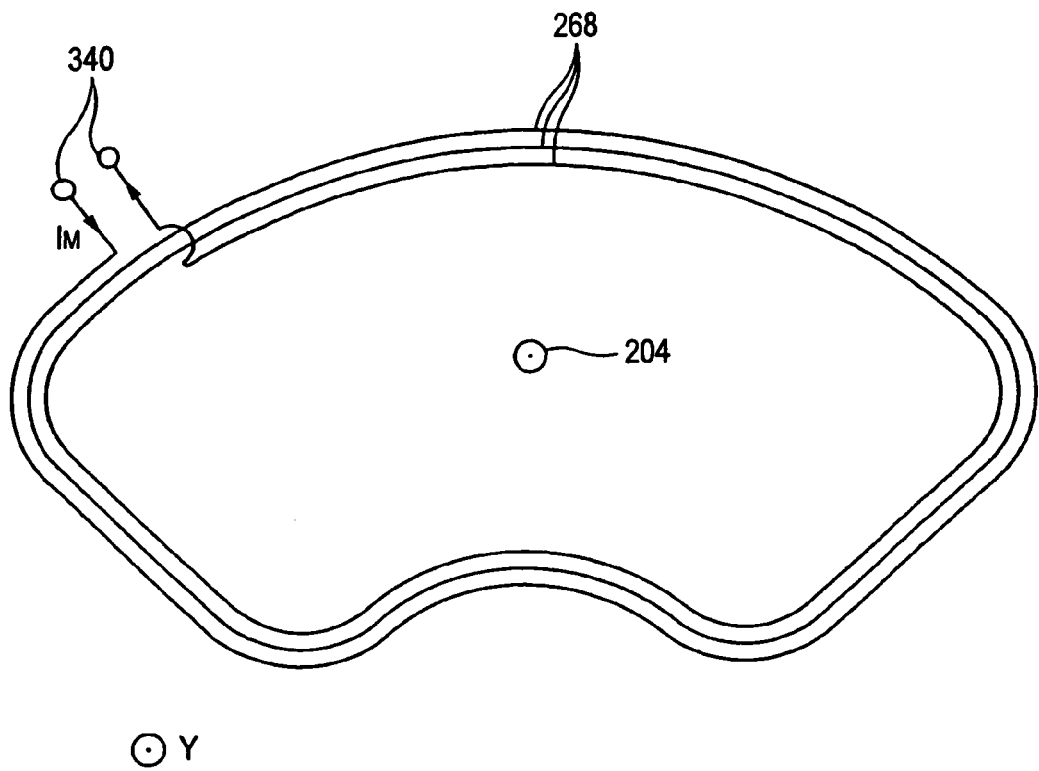
FIG. 26 is a schematic plan view showing a manner of winding a conductor sheet shown in FIG. 25.

As seen in a plan view, the conductor sheet 268 of the first inner coil 206 has a structure where it is wound in multiple turns in a fan-like shape as shown in FIG. 26, and terminals 340 are connected to the ends of the sheet. However, the number of turns is not restricted to the illustrated one. When a current $I_M$ flows trough the conductor sheet 268, the magnetic force lines 204 which form the main magnetic field can be generated. The same current $I_M$ and magnetic force lines 204 are shown also in FIG. 27.

As seen in a plan view, also the conductor sheet 269 of the first outer coil 218 has a similar structure as that of FIG. 26.

The second inner and outer coils 212, 224 are structured in a similar manner as the first inner and outer coils 206, 218. As described above, however, the coils have a plane-symmetrical shape about the symmetry plane 234 with respect to the first inner and outer coils 206, 218.

Figure 38:
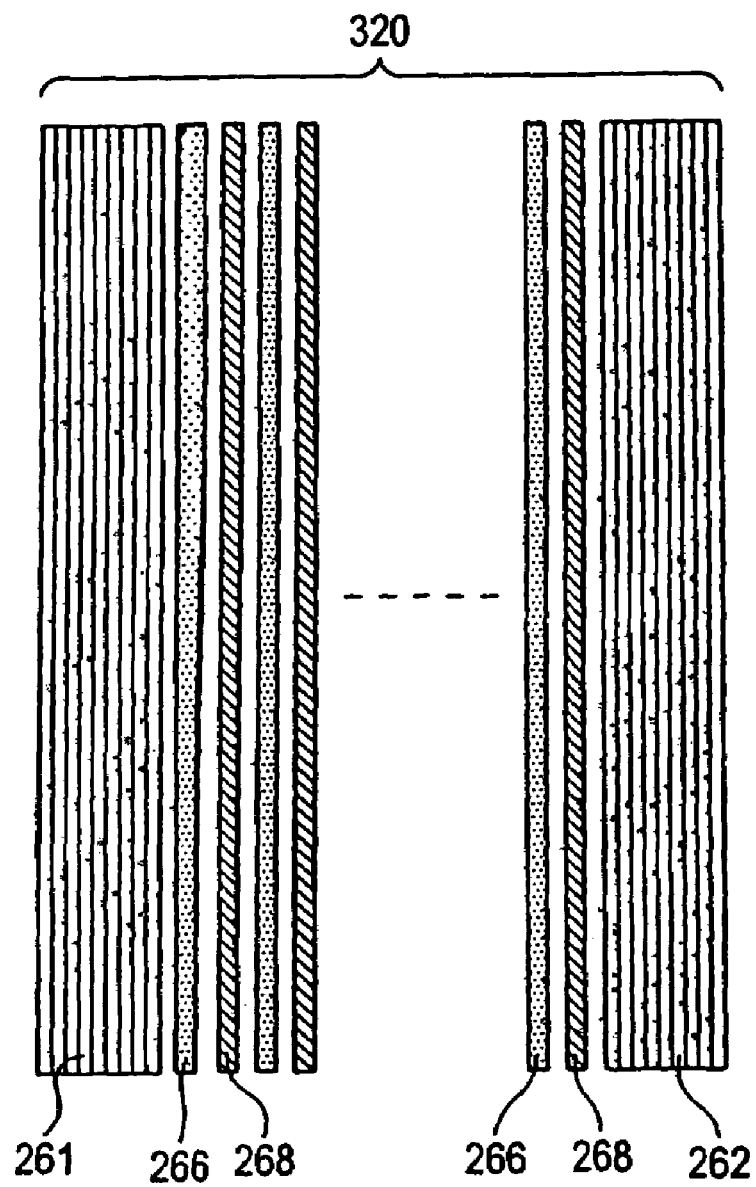
FIG. 38 is a view explodedly showing a section of the coil, along the line J-J of FIG. 37.

As required, a member for performing reinforcement of the coils, and the like may be further disposed on the outer periphery of the outer stacked insulator 263 (in the case of coils shown in FIG. 38, the stacked insulator 262).

A structure example of the connecting portions of the coils will be described in more detail with reference to FIG. 27 with taking the first inner coil 206 as an example.

Each of the connecting portions 210 of the first inner coil 206 has: two vertical portions 282 which are substantially perpendicularly connected to end portions of the body portions 208 in the Z direction, and which extend in substantially parallel to the Y direction; and a lateral portion 284 which is substantially perpendicularly connected to the vertical portions 282, and which extends in substantially parallel to the XZ plane. Namely, the vertical portions 282 are connected to each other by the lateral portion 284. Therefore, the first inner coil 206 has: lateral conduction paths 286 which are substantially perpendicular to the Y direction; and vertical conduction paths 288 which are substantially parallel to the Y direction. Namely, most of the conduction path of the first inner coil 206 is configured by a combination of the conduction paths 286 and 288 excluding edge portions. The current densities in all places of the conduction paths 286 and 288 are set to be identical to one another.

The connecting portions 216, 222, 228 of the other coils 212, 218, 224 are configured in a similar manner as the connecting portions 210. Therefore, each of the other coils 212, 218, 224 has lateral conduction paths which are substantially perpendicular to the Y direction, and vertical conduction paths which are substantially parallel to the Y direction. Namely, most of the conduction path of the coil is configured by a combination of the lateral conduction paths and the vertical conduction paths excluding edge portions. The current densities in all places of the lateral and vertical conduction paths are set to be identical to one another. The coil 320 which will be described later is configured in a similar manner.

The connecting portions of the coils are preferably structured as described above. According to the structure, the projection distances of the connecting portions from the analyzing electromagnet 200 in the directions of beam incidence and emission can be surely shortened. The projection distances will be described later in detail.

A configuration example of power sources for the coils is shown in FIG. 28. In the example, DC main power sources 250 are connected to the first and second inner coils 206, 212, respectively. The main power sources 250 can supply the currents $I_m$ which are substantially identical in level to each other, to the first and second inner coils 206, 212, respectively. The two main power sources 250 are not required to be separately disposed, and may be configured as a single combined main power source.

In this example, furthermore, DC sub-power sources 252 are connected to the first outer coils 218 (218a to 218c) and the second outer coils 224 (224a to 224c), respectively. The sub-power sources 252 can supply currents $I_S$ to the first and second outer coils 218, 224, respectively, and the currents $I_S$ flowing through the first and second outer coils 218, 224 can be independently controlled. The plural sub-power sources 252 are not required to be separately disposed, and may be configured as a single combined sub-power source which can independently control the currents Is respectively flowing through the first and second outer coils 218, 224.

(3-4) Methods of Producing Coils, Etc.

Next, examples of methods of producing the coils will be described with taking the first inner and outer coils 206, 218 as examples.

First, the fan-shaped cylindrical stacked coil 290 shown in FIG. 29 is produced. This production is performed in the following manner.

As shown in FIG. 16, first, a mandrel 296 having an arcuate portion 297 which is outward projected in a manner opposite to an arcuate portion 291 of the stacked coil 290 shown in FIG. 29 is rotated about an axis 298 in a constant direction as indicated by the arrow 299, whereby the prepreg sheet 300 such as described above is wound in multiple turns. As a result, the stacked insulator 261 shown in FIGS. 30 and 32 is formed.

Figure 32:
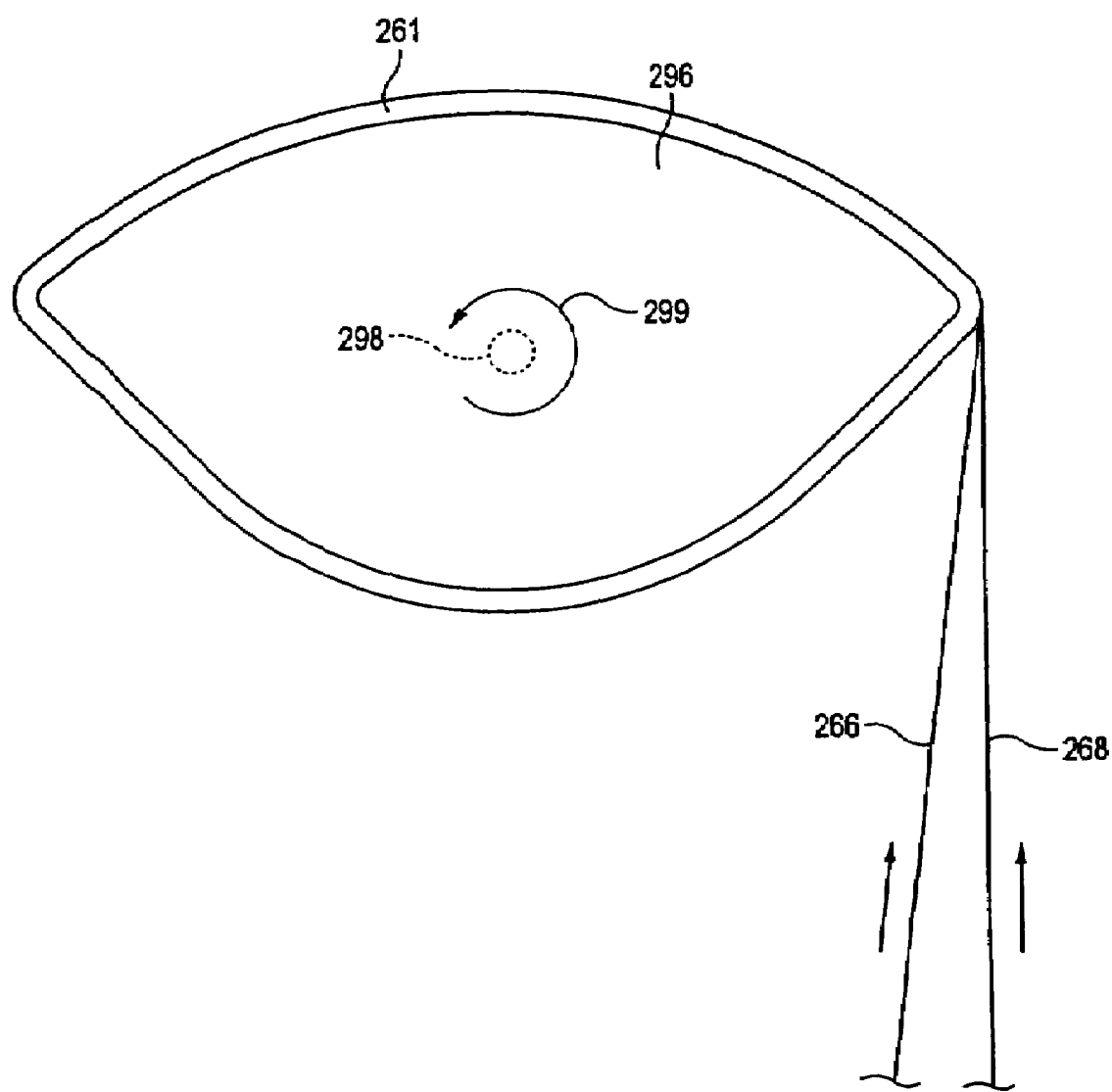
FIG. 32 is a plan view showing an example of a manner of winding an insulation sheet and a conductor sheet with using a mandrel.

Next, as shown in FIG. 32, the mandrel 296 is rotated in the same manner as described above to wind and laminate the insulation sheet 266 and the conductor sheet 268 while they overlap with each other, in multiple turns on the outer peripheral face of the stacked insulator 261. As a result of the above, a lamination of the insulation sheet 266 and the conductor sheet 268 shown in FIG. 30 is formed.

Next, in a similar manner as the case of FIG. 16, the prepreg sheet 300 is wound in multiple turns on the outer peripheral face of the lamination of the insulation sheet 266 and the conductor sheet 268, whereby the stacked insulator 262 shown in FIG. 30 is formed.

Next, in a similar manner as the case of FIG. 32, the insulation sheet 267 and the conductor sheet 269 are wound while they overlap with each other, in multiple turns on the outer peripheral face of the stacked insulator 262, whereby a lamination of the insulation sheet 267 and the conductor sheet 269 shown in FIG. 30 is formed.

Next, in a similar manner as the case of FIG. 16, the prepreg sheet 300 is wound in multiple turns on the outer peripheral face of the lamination of the insulation sheet 267 and the conductor sheet 269, whereby the stacked insulator 263 shown in FIG. 30 is formed.

After the above steps, the mandrel 296 is removed, and then a stacked coil 290a which is configured by the inner coil 292 and the outer coil 294, but in which an arcuate portion 291a is projected in a manner opposite to the arcuate portion 291, or to the outside is obtained.

When lead plates are disposed in winding start and end portions of the conductor sheet 268, the conductor sheet 268 can be connected to the terminals 340 (see FIG. 26) with using the lead plates. The conductor sheet 269 is configured in a similar manner.

Before the winding process, preferably, abrasive grains (shots) such as metal grains are blown (i.e., a shot-blast process is applied) to the principal faces 268a, 269a of the front and rear sides of the conductor sheets 268, 269 to roughen the surfaces. According to the configuration, the surface areas can be increased, and the close contact with respect to the insulation sheets 266, 267 and the like can be enhanced. Even when the shot-blast process is applied at least on one principal face of each of the conductor sheets 268, 269, the effects can be attained. However, it is preferable to apply the process on the both principal faces. This is applicable also to the insulation sheets 266, 267.

Similarly, it is preferable to apply a shot-blast process to the principal faces 266a, 267a of the front and rear sides of the insulation sheets 266, 267, to roughen the surfaces. According to the configuration, the surface areas can be increased, and the close contact with respect to the conductor sheets 268, 269 and the like can be further enhanced.

Figure 33:
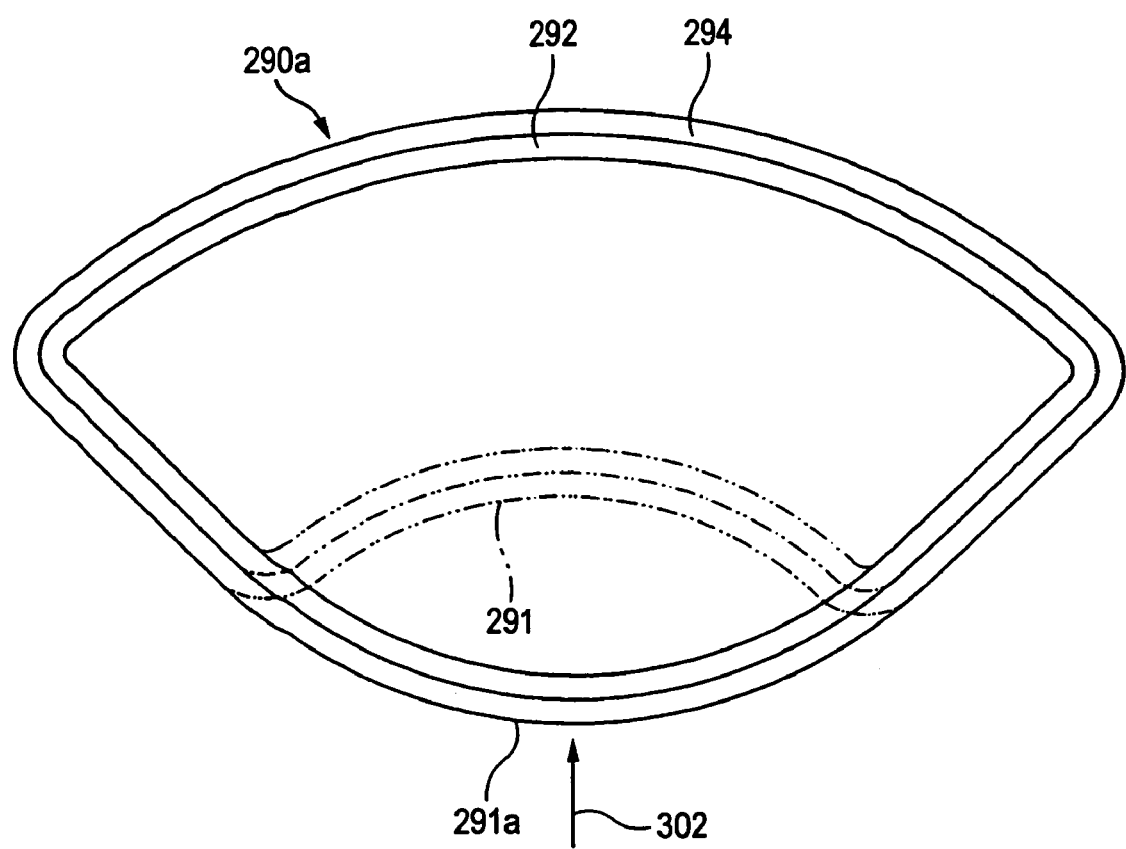
FIG. 33 is a plan view showing an example of a stacked coil which has been wound with using a mandrel.

Next, a heat-shrinkable tape (not shown) is wound around the outer periphery of the stacked coil 290a, and then the arcuate portion 291a is pressed as indicated by the arrow 302 in FIG. 33 to perform a molding process of forming the arcuate portion 291. The resulting article is heat cured. As a result, a stacked coil 290b from which the stacked coil 290 shown in FIG. 26 will be formed is obtained. The winding of the heat-shrinkable tape improves the strength of the structure. In place of the heat-shrinkable tape, a prepreg tape which is configured in a similar manner as the above-mentioned prepreg sheet may be wound.

Next, the stacked coil 290b is vacuum-impregnated with a resin, and then heat cured under a pressurized condition. Briefly speaking, this means that a resin molding process is performed. As a result, the stacked coil 290 shown in FIG. 29 is obtained. The resin molding process can increase the adhesion strengths between the layers of the stacked coil 290 to enhance the strength of the coil and also the electrical insulation property.

Next, the both end faces in the axial direction (in other words, the height direction) of the stacked coil 290 are subjected to a cutting process to be formed as flat faces. Thereafter, the portions 272a to 275a corresponding to the notched portions are subjected to a cutting process to form the notched portions 272 to 275.

In the case where the outer coil 294 is configured as the plural first outer coils 218, a grooving process is applied portions of the outer coil 294 which correspond to the gaps 244, thereby forming the gaps 244.

Next, a stacked coil 290c on which the cutting and grooving processes have been applied is immersed in an etching solution which etches the materials (as described above, copper or aluminum) of the conductor sheets 268, 269, thereby performing an etching process. As a result, burrs and the like of the conductor sheets 268, 269 which are produced on the processed faces during the cutting and grooving processes are removed away to prevent a short circuit (layer short) between layers in the conductor sheets 268, 269 from occurring, and end faces of the conductor sheets 268, 269 are further roundly recessed than those of the insulation sheets 266, 267 to increase the creepage distance of the layer insulation in the conductor sheets 268, 269, whereby the insulation performance can be improved.

A heat-shrinkable tape is wound around the whole of a stacked coil 290d on which the above-described etching process has been applied, and then heat cured. As a result, it is possible to obtain a fan-shaped cylindrical stacked coil in which the first inner and outer coils 206, 218 shown in FIGS. 19 to 25 and the like are integrated with each other. The winding of the heat-shrinkable tape improves the strength of the structure. In the case where the coils have a forced cooling structure which will be described below, the cooling plates 312 may be attached in the following manner before the heat-shrinkable tape is wound. In place of the heat-shrinkable tape, a prepreg tape which is configured in a similar manner as the above-mentioned prepreg sheet may be wound.

Figure 34:
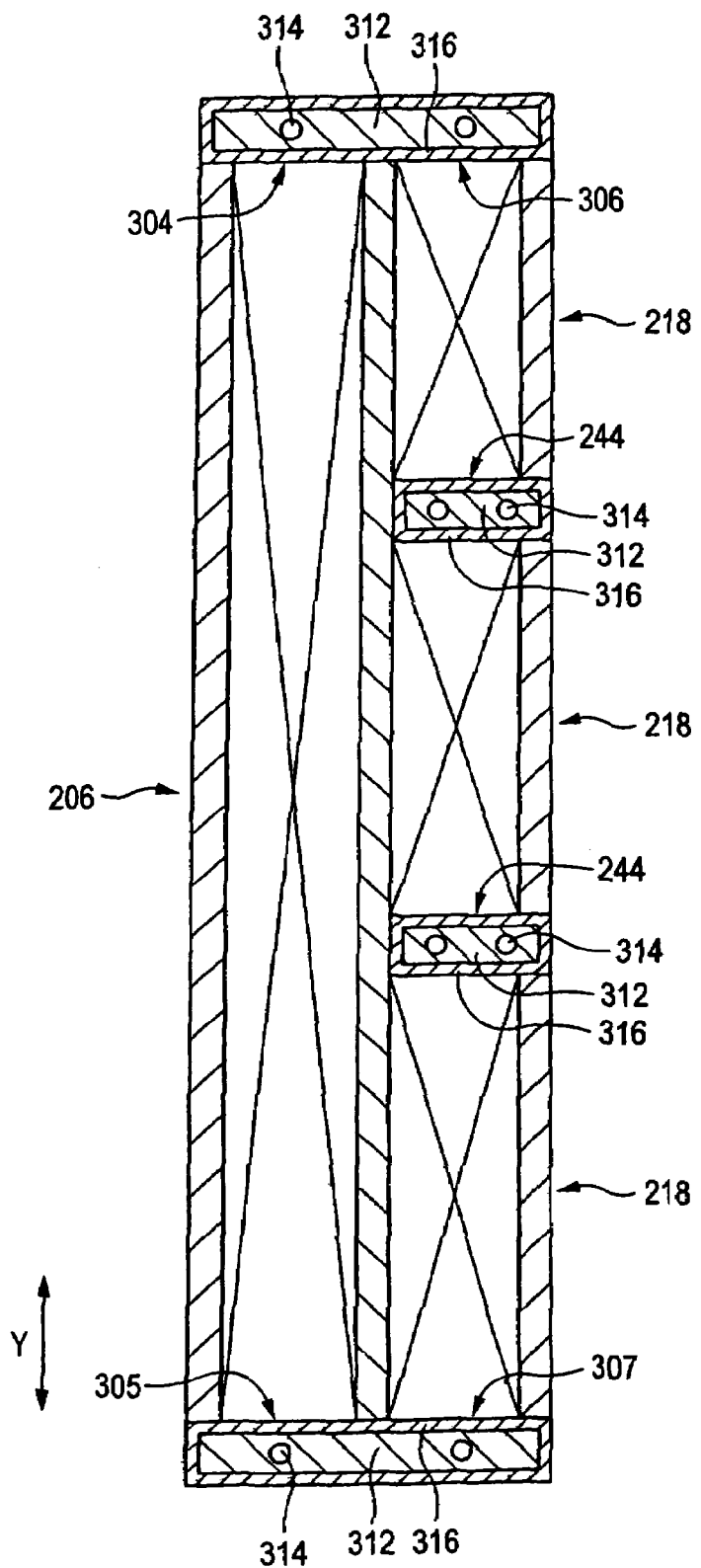
FIG. 34 is a section view showing an example of attachment of cooling plates to the first and second inner coils.

As shown in FIG. 34, the cooling plates 312 having a coolant passage 314 are pressingly contacted and attached via insulators 316 to upper and lower end faces 306, 307 and gaps 244 of the first inner and outer coils 206, 218, respectively. Preferably, the cooling plates 312 are disposed not only in the upper and lower end faces in the Y direction of the body portions 208, 220 of the coils 206, 218, but also in the upper and lower end faces in the Y direction of the connecting portions 210, 222. Namely, preferably, the plates are disposed in a region as wide as possible. For example, cooling water flows through the coolant passages 314. In the example, the insulators 316 are wound around the cooling plates 312. However, it is not required to wind the insulators.

The coils 206, 218 can be forcedly cooled through their end faces by the cooling plates 312. Such a cooling structure is also called an end cooling system.

In the above-described case, preferably, a heat diffusion compound (for example, silicone grease) having a high thermal conductivity is interposed (for example, applied) between the cooling plates 312 and the insulators 316, and between the insulators 316 and the end faces of the coils 206, 218. According to the configuration, an air space can be eliminated as far as possible, and the thermal conductivity performance and hence the cooling performance can be improved.

Each of the gaps 244 may be configured as a wedge-like shape in which the width is narrower as more advancing toward the inner side (the left side of FIG. 34) of the coil 218. Also the cooling plate 312 to be attached to the gap may be configured as a similar wedge-like shape, so that the cooling plate 312 is pressingly inserted into the gap. According to the configuration, the gap which is formed between the end face of the coil 218 and the cooling plate 312 can be made small so that the close contact can be improved. Therefore, the cooling performance can be further improved.

In the case where the cooling plates 312 are disposed as described above, the heat-shrinkable tape or prepreg tape may be wound around the whole coil in the state shown in FIG. 34, and then heat cured. This can perform also fixation and close contact of the cooling plates 312.

Finally, as required, also in both cases where the cooling plates 312 are disposed, and where the cooling plates are not disposed, the whole coil including the first inner and outer coils 206, 218 may be molded by a resin. According to the configuration, the moisture resistance, insulation property, mechanical strength, and the like of the coils can be further improved. In this case, preferably, 5 to 30 wt. % of a filler (filling agent) may be mixed with the resin. According to the configuration, the crack resistance of the resin, and the like can be improved.

In a similar manner as described above, also the second inner and outer coils 212, 224 can be produced as a coil in which the coils 212, 224 are integrated. Coils which will be described later, i.e., the coil 320 shown in FIGS. 37 to 39, the first and second coils 326, 328 shown in FIG. 40, and the inner coil 330 and first and second outer coils 218, 224 shown in FIG. 41 are produced in a similar manner as described above. The inner and outer coils can be produced integrally with each other.

With using the coils 206, 218, 212, 224, the analyzing electromagnet 200 shown in FIGS. 19 and 20, and the like may be assembled in, for example, the following procedure. Namely, while the upper yoke 231 of the yoke 230 is kept to be removed away, a member in which the second inner coil 212 is integrated with the second outer coil 224 is inserted from the upper side into the yoke 230, the vacuum vessel 236 is then inserted from the upper side, and a member in which the first inner coil 206 is integrated with the first outer coil 218 is then inserted from the upper side. Finally, the upper yoke 231 is attached.

(3-5) Features of Analyzing Electromagnet 200, and the Like

In the analyzing electromagnet 200, the first inner and outer coils 206, 218 have the configuration where the notched portions 272 to 275 are disposed in the fan-shaped cylindrical stacked coil 290 while leaving the body portions 208, 220 and the connecting portions 210, 222, and hence the connecting portions 210, 222 are in a state where the portions are extended in the Y direction from the end portions of the body portions 208, 220 in substantially parallel. Even in the case where the dimension in the Y direction of the body portions 208, 220 is increased, therefore, the case is coped with by correspondingly increasing the dimension in the Y direction of the connecting portions 210, 222. As a result, the projection distances of the connecting portions 210, 222 in the directions of beam incidence and emission are not increased.

The above will be described with taking the first inner coil 206 as an example with reference to FIG. 23. In the case where the dimension a in the Y direction of the body portions 208 is increased, the case is coped with by correspondingly increasing the dimension c in the Y direction of the connecting portions 210. Specifically, the dimensions a and c are substantially equal to each other. Even when the dimension a is increased, therefore, the projection distance $L_3$ (see FIG. 19) of the connecting portions 210 in the directions of incidence and emission of the ion beam 50 is not increased. The projection distance $L_3$ is determined by the distance $L_5$ between the end face of the yoke 230 and that of the connecting portion 210, and the thickness b of the connecting portion 210. Namely, the projection distance $L_3$ can be indicated by the following expression. As seen also from the description of the structure of the first inner coil 206, also the body portions 208 have the thickness of b.

$$L_3 = b + L_5 \qquad [\text{Exp. 4}]$$

Unlike above-described Exp. 3 indicating the projection distance $L_1$ of the conventional analyzing electromagnet 40, above-described Exp. 4 does not include the dimension a in the Y direction. This is a feature which is largely different from the conventional analyzing electromagnet 40.

Moreover, also the distance $L_5$ can be made smaller than the distance $L_2$ of the conventional analyzing electromagnet 40. This is caused because of the following reasons. Unlike the conventional coil 12, the connecting portions 210 are formed not by obliquely raising the connecting portions 16 by a bending process, but by, as described above, disposing the notched portions 272 to 275 in the fan-shaped cylindrical stacked coil 290, and the connecting portions 210 extend in substantially parallel in the Y direction. Moreover, edge portions 254 between the body portions 208 and the connecting portions 210 can be made in a state where they are less rounded or substantially perpendicular, by a cutting process, or the like.

Because of the above-described reasons, the projection distance $L_3$ of the connecting portions 210 from the yoke 230 in the directions of beam incidence and emission can be reduced.

The second inner and outer coils 212, 224 are configured in a similar manner.

When the dimension a in the Y direction is set to an identical value or 250 mm, the projection distance $L_1$ of the conventional analyzing electromagnet 40 is about 300 mm, and in contrast the projection distance $L_3$ of the analyzing electromagnet 200 is about 110 mm.

Because of the same reasons as described above, even in the case where the inner coils 206, 212 and the outer coils 218, 224 are doubly disposed as in the analyzing electromagnet 200, projection distances $L_4$ of the outer coils 218 from the yoke 230 in the directions of beam incidence and emission can be reduced. In the conventional analyzing electromagnet 40, if coils are doubly disposed in inner and outer sides, the projection distances of the connecting portions are increased very much.

Because of the above reasons, the analyzing electromagnet 200 can be miniaturized, and therefore the area required for installing the analyzing electromagnet 200 can be reduced. Also the weight of the analyzing electromagnet 200 can be reduced. Moreover, the possibility that the magnetic fields generated by the connecting portions of the coils 206, 218, 212, 224 disturb the form of the ion beam 50 is reduced.

In accordance with that the projection distances of the connecting portions of the coils 206, 218, 212, 224 can be reduced, also the lengths of the connecting portions can be shortened, and hence wasteful power consumption in the connecting portions can be reduced.

Moreover, the coils 206, 218, 212, 224 have the structure in which, as described above, the conductor sheets 268, 269 are stacked with interposing the insulation sheets 266, 267 therebetween. As compared with a multi-turn coil in which a coated conductor is wound many times, therefore, the space factor of the conductor is high, and the power loss is correspondingly low. Consequently, the power consumption can be reduced.

For example, the case where the dimension a in the Y direction of each coil is set to 250 mm will be considered. The conductor space factor of a multi-turn coil of a coated conductor in the conventional art is about 60 to 70% even in the case where the conductor is not hollow (is not a hollow conductor), and further reduced in the case of a hollow conductor. By contrast, the space factors of the conductors of the coils 206, 218, 212, 224 can be set to about 84 to 85%.

As a result, in the analyzing electromagnet 200, a magnetic field of a required strength can be generated at a power consumption which is smaller than that in the conventional analyzing electromagnet 40. At the same power consumption, a magnetic field which is stronger than that generated by the conventional analyzing electromagnet 40 can be generated. In the latter case, the radius of curvature R of the ion beam deflection can be reduced, so that the analyzing electromagnet 200 can be further miniaturized.

In the case where the dimension a in the Y direction of each coil is set to 250 mm and a magnetic field of 0.2 tesla is generated by the two coils 206, 212 (the coils 218, 224 are not used) in the same manner as the conventional analyzing electromagnet 40, the power consumption of the conventional analyzing electromagnet 40 is about 67 kW, and in contrast that of the analyzing electromagnet 200 is only about 24 kW.

The ion implanter shown FIG. 1 comprises the analyzing electromagnet 200 having the above-described features. In accordance with the miniaturization of the analyzing electromagnet 200, therefore, the whole ion implanter can be miniaturized, and hence the area required for installing the ion implanter can be reduced. Also the weight of the ion implanter can be reduced. Moreover, in accordance with the reduction of the power consumption of the analyzing electromagnet 200, the power consumption of the whole ion implanter can be reduced.

Furthermore, since the analyzing electromagnet 200 comprises the above-described first and second inner coils 206, 212, it is possible to easily cope with the ion beam 50 having a large Y-direction dimension $W_Y$ as compared with the case where one coil is used in each of upper and lower sides.

Moreover, the first and second outer coils 218, 224 can generate the sub-magnetic field which assists or corrects the main magnetic field. Because of the sub-magnetic field, the main magnetic field can be corrected, and the homogenization of the magnetic flux density distribution in the Y direction can be enhanced. The sub-magnetic field generated by the outer coils 218, 224 may be weaker than the main magnetic field, and therefore can be easily controlled.

The above-described main and sub-magnetic fields enable a magnetic field in which the homogenization of the magnetic flux density distribution in the Y direction is high, to generate in the beam path 202. As a result, the disturbance (bend, inclination, and the like, the same shall apply hereinafter) of the form of the ion beam 50 at the emission from the analyzing electromagnet 200 can be suppressed to a lower level. This effect is more remarkable in the case where the Y-direction dimension $W_Y$ of the ion beam 50 is large.

Even when one first outer coil 218 and one second outer coil 224 are used, it is possible to attain the effect of correcting the main magnetic field. However, it is preferred that, as in the example, plural first outer coils 218 and plural second outer coils 224 are disposed. In this case, the magnetic flux density distribution in the Y direction of the magnetic field generated in the beam path 202 can be corrected more finely by theses outer coils 218, 224. Therefore, it is possible to generate a magnetic field in which the homogenization in the Y direction is higher. As a result, the disturbance of the form of the ion beam 50 at the emission can be suppressed to a lower level.

(3-6) Method of Controlling Analyzing Electromagnet 200

An example of the method of controlling the analyzing electromagnet 200 will be described. The currents flowing through the first and second outer coils 218, 224 can be controlled so that the form of the ion beam 50 emitted from the analyzing electromagnet 200 approaches to that of the ion beam 50 at incidence.

Specifically, the form of the ion beam 50 emitted from the analyzing electromagnet 200 is caused to approach to a form which is parallel to a predetermined center axis (a center axis 318 shown in FIGS. 35 and 36) which is substantially parallel to the Y direction, by performing at least one of: a decrease of currents flowing through the first and second outer coils 218, 224 corresponding to portions which are excessively bent with respect to the center axis toward the inner side of the radius of curvature R in the ion beam 50 emitted from the analyzing electromagnet 200; and an increase of currents flowing through the first and second outer coils 218, 224 corresponding to portions which are deficient in bending toward the inside. This makes the ion beam 50 emitted from the analyzing electromagnet 200 have a form which is not inclined but straight, and which approaches to the form at incidence.

Figure 35:
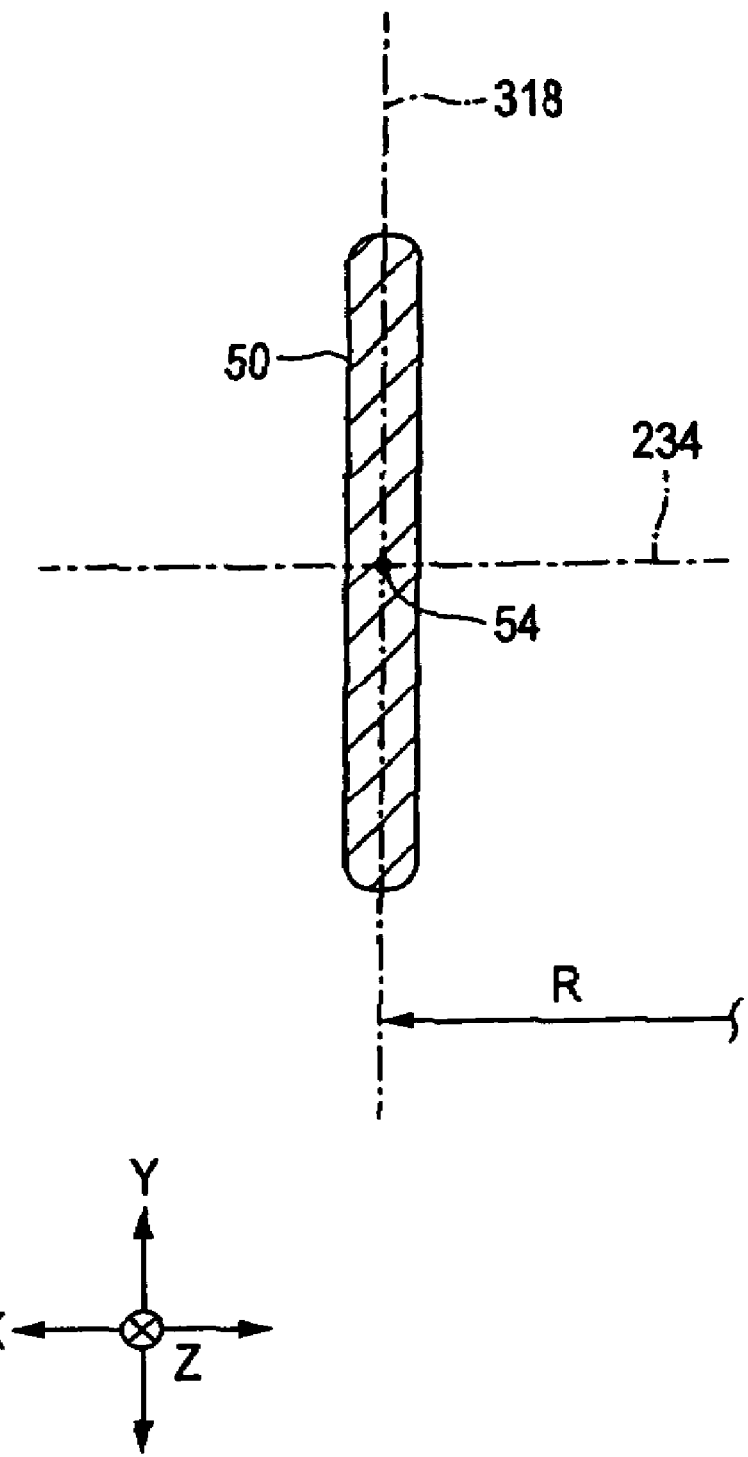
FIG. 35 is a view showing an example of an ion beam having a normal form immediately after it is emitted from the analyzing electromagnet.
Figure 36:
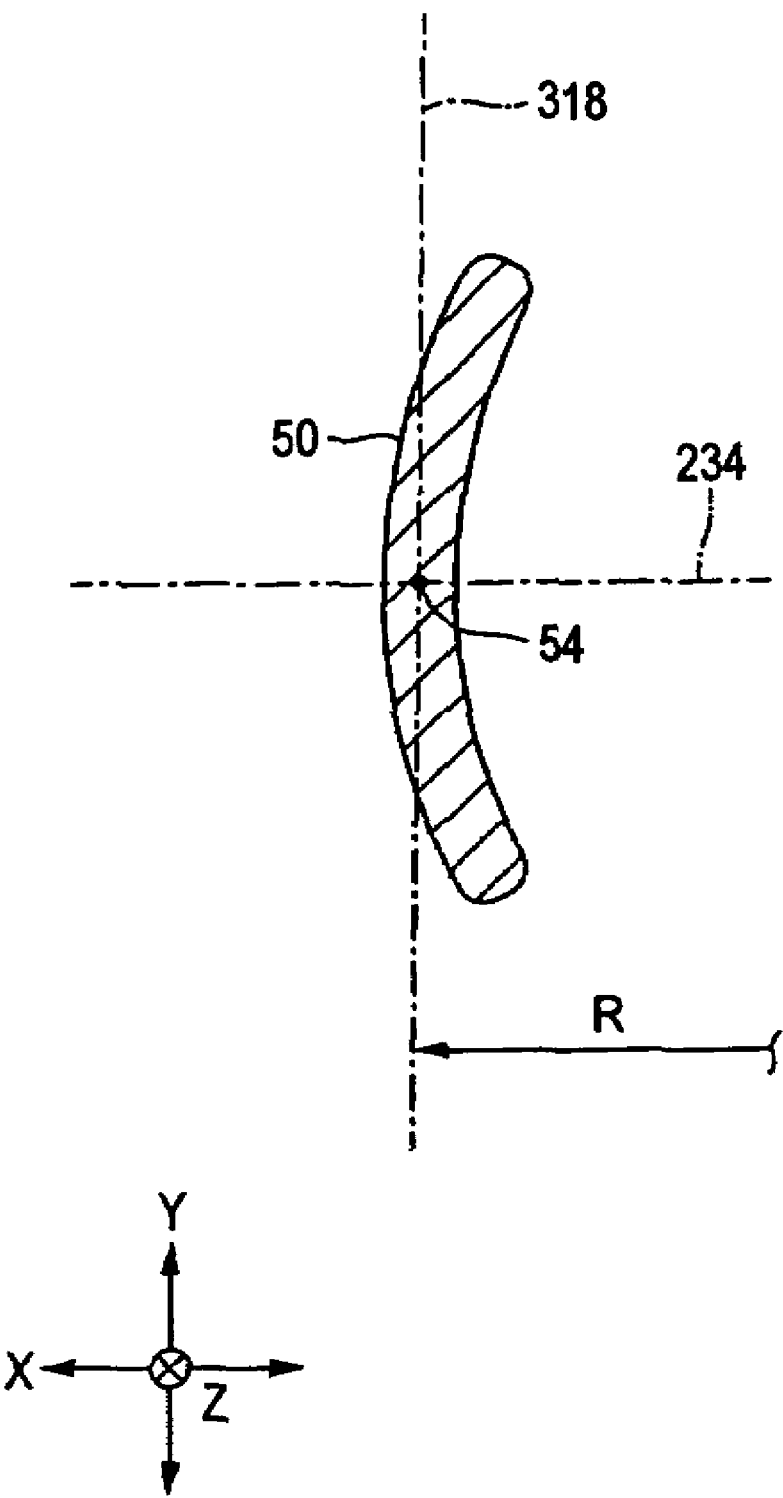
FIG. 36 is a view showing an example of an ion beam having a distorted form immediately after it is emitted from the analyzing electromagnet.

FIGS. 35 and 36 show examples of the form of the ion beam 50 emitted from the analyzing electromagnet 200, respectively. In the figures, a predetermined center axis which is substantially parallel to the X direction is indicated by 318, the symmetry plane is indicated by 234, the center orbit of the ion beam 50 is indicated by 54, and the radius of curvature is indicated by R.

In the case of the form shown in FIG. 35, the form of the ion beam 50 is not disturbed as viewed in the traveling direction Z of the ion beam 50, and hence the values of currents flowing through the first outer coils 218*a* to 218*c* and the second outer coils 224*a* to 224*c* can be maintained.

In the case of the form shown in FIG. 36, the ion beam 50 is distorted (bent) into an arcuate shape which is similar to an L-like shape as viewed in the traveling direction Z, or namely more excessively bent toward the inner side of the radius of curvature R as further advancing toward the upper side in the Y direction, and more excessively bent toward the inner side as further advancing toward the lower side. Therefore, the current flowing through the first outer coil 218*a* is largely reduced, that flowing through the first outer coil 218*b* is slightly reduced, the currents flowing through the first outer coil 218*c* and the second outer coil 224*c* are maintained to the present values, the current flowing through the second outer coil 224*b* is slightly reduced, and that flowing through the second outer coil 224*a* is largely reduced. As a result, while maintaining the position of the center orbit 54 of the ion beam 50 emitted from the analyzing electromagnet 200, the form of the ion beam can be made close to that which is parallel to the center axis 318. Namely, the form can approach to that shown in FIG. 35.

Also in the case where the form of the ion beam 50 emitted from the analyzing electromagnet 200 is disturbed to that other than that shown in FIG. 36, the correction is performed with the same idea as described above, and the form can approach to that shown in FIG. 35.

In the case where the form of the ion beam 50 emitted from the analyzing electromagnet 200 is disturbed, the following problems mainly arise. According to the control method, it is possible to prevent the problems from arising.

Usually, the analysis slit 70 shown in FIG. 1 is disposed in the downstream side of the analyzing electromagnet 200. The slit 72 of the analysis slit 70 is linear. When the form of the ion beam 50 is disturbed, therefore, a portion which is cut by the analysis slit 70 is produced, and the amount of the ion beam 50 of a desired ion species which passes through the analysis slit 70 is reduced. Because the cut portion is produced, the homogenization of the ion beam 50 is impaired. When the X-direction width of the slit 72 is increased in order to prevent such cutting from occurring, the resolution is lowered.

In addition to the above-discussed problems of the analysis slit 70, there arises a problem in that, when the ion implantation is performed on the substrate 60 with using the ion beam 50 in which the form is disturbed, the homogenization of the implantation is impaired.

(3-7) Other Examples of Analyzing Electromagnet 200

Next, other examples of the analyzing electromagnet 200 will be described. The portions which are identical or corresponding to those of the previous example shown in FIGS. 19 to 22 and the like are denoted by the same reference numerals, and duplicated description will be omitted. In the following description, emphasis is placed on differences from the previous example.

Figure 39:
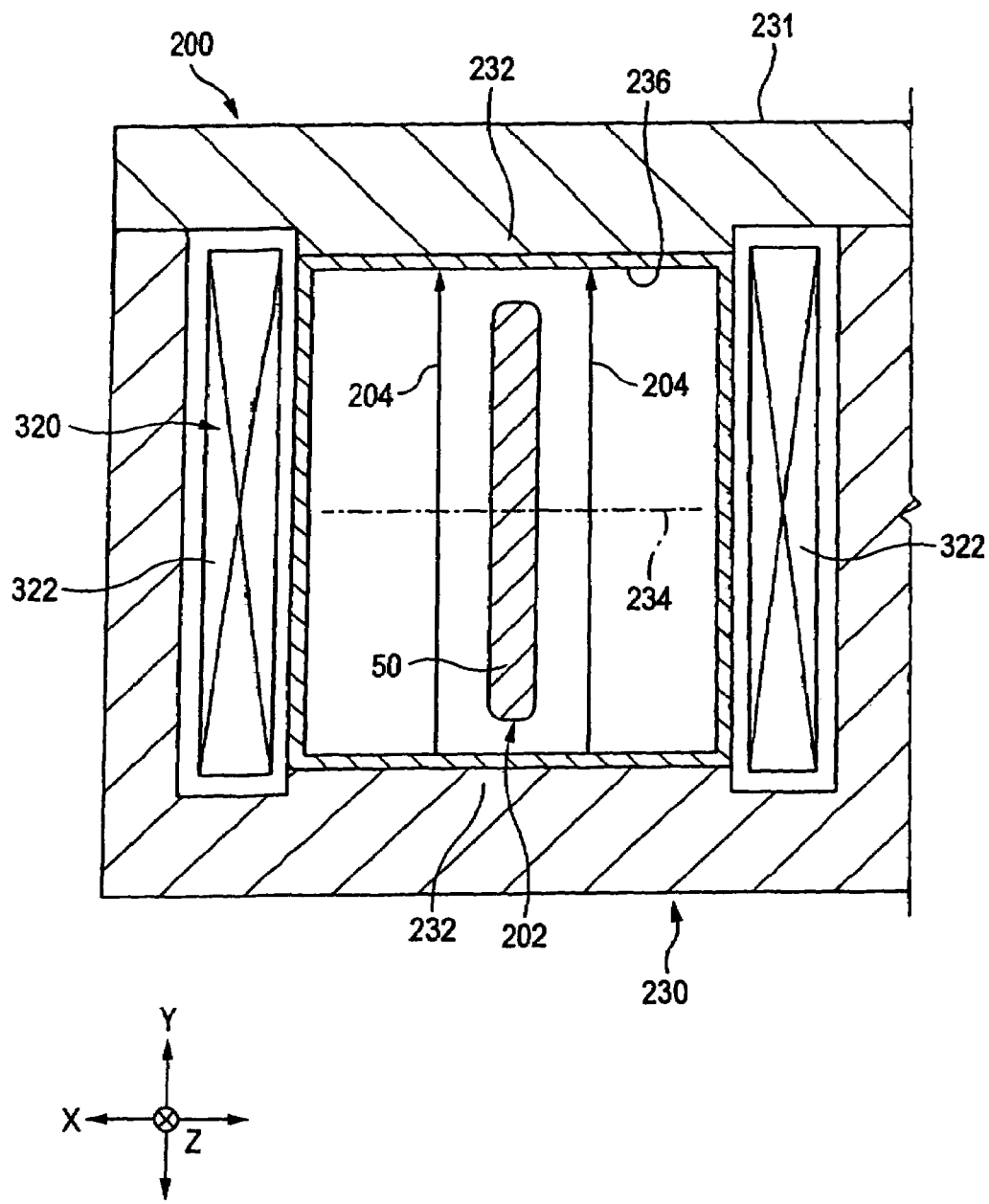
FIG. 39 is a section view showing another example of the analyzing electromagnet and corresponding to FIG. 20.

Also referring to FIG. 37, the analyzing electromagnet 200 shown in FIG. 39 comprises a coil 320 which has: one set of body portions 322 that are opposed to each other in the X direction across the beam path 202; and two sets of connecting portions 324, 325 that connect end portions of the body portions 322 in the Z direction with each other, while avoiding the beam path 202, and which generates a magnetic field that bends the ion beam 50 in the X direction. The two connecting portions 324 which are in the upper side in FIG. 37 are one set of connecting portions, and the two connecting portions 325 which are in the lower side are the other one set of connecting portions.

As seen from FIG. 38 showing the section structure of the coil 320, the coil has the same section structure as the first inner coil 206 (see FIG. 25) and the inner coil 292 (see FIG. 30) of the stacked coil 290. Namely, the coil 320 has a configuration where notched portions 276 to 281 are disposed in a fan-shaped cylindrical stacked coil having the same structure as the inner coil 292 while leaving the body portions 322 and the connecting portions 324, 325. Also the coil 320 can be produced by the same production method as described above.

The coil 320 is configured as one coil in which the above-described first and second inner coils 206, 212 (see FIG. 23) are vertically integrated with each other.

The notched portions 276, 277 are similar in shape to the above-described notched portions 272, 273. The notched portions 278, 279 have a plane-symmetrical shape about a symmetry plane (see FIG. 39) with respect to the notched portions 276, 277. Specifically, the notched portions 280, 281 are through holes, and form the inlet 238 and the outlet 240, respectively, and the ion beam 50 can pass through the notched portions. More specifically, the ion beam 50 can pass therethrough via the vacuum vessel 236.

The vacuum vessel 236 is caused to pass through the coil 320 by inserting the vacuum vessel 236 via the notched portions 280, 281 in the Z direction. In this case, when a flange or the like is disposed on the vacuum vessel 236 and causes a hindrance, the flange or the like is once detached. The analyzing electromagnet 200 may be assembled by a similar method.

The connecting portions 324 are structured in a similar manner as the connecting portions 210 of the first inner coil 206. The connecting portions 325 have a plane-symmetrical shape about the symmetry plane 234 with respect to the respective connecting portions 324.

The Y-direction dimension $a_1$ of the body portions 322 is substantially equal to a total (i.e., $2c_1$) of the Y-direction dimension $c_1$ of the connecting portions 324 and the Y-direction dimension $c_1$ of the connecting portions 325.

Also in the analyzing electromagnet 200 of the example, the coil 320 is configured as one coil in which the above-described first and second inner coils 206, 212 are integrated with each other. Because of the same reason as described above, therefore, the projection distance of the connecting portions 324, 325 of the coil 320 from the yoke 230 is reduced, thereby attaining effects such as that the analyzing electromagnet 200 can be miniaturized, and that the power consumption can be reduced.

Figure 40:
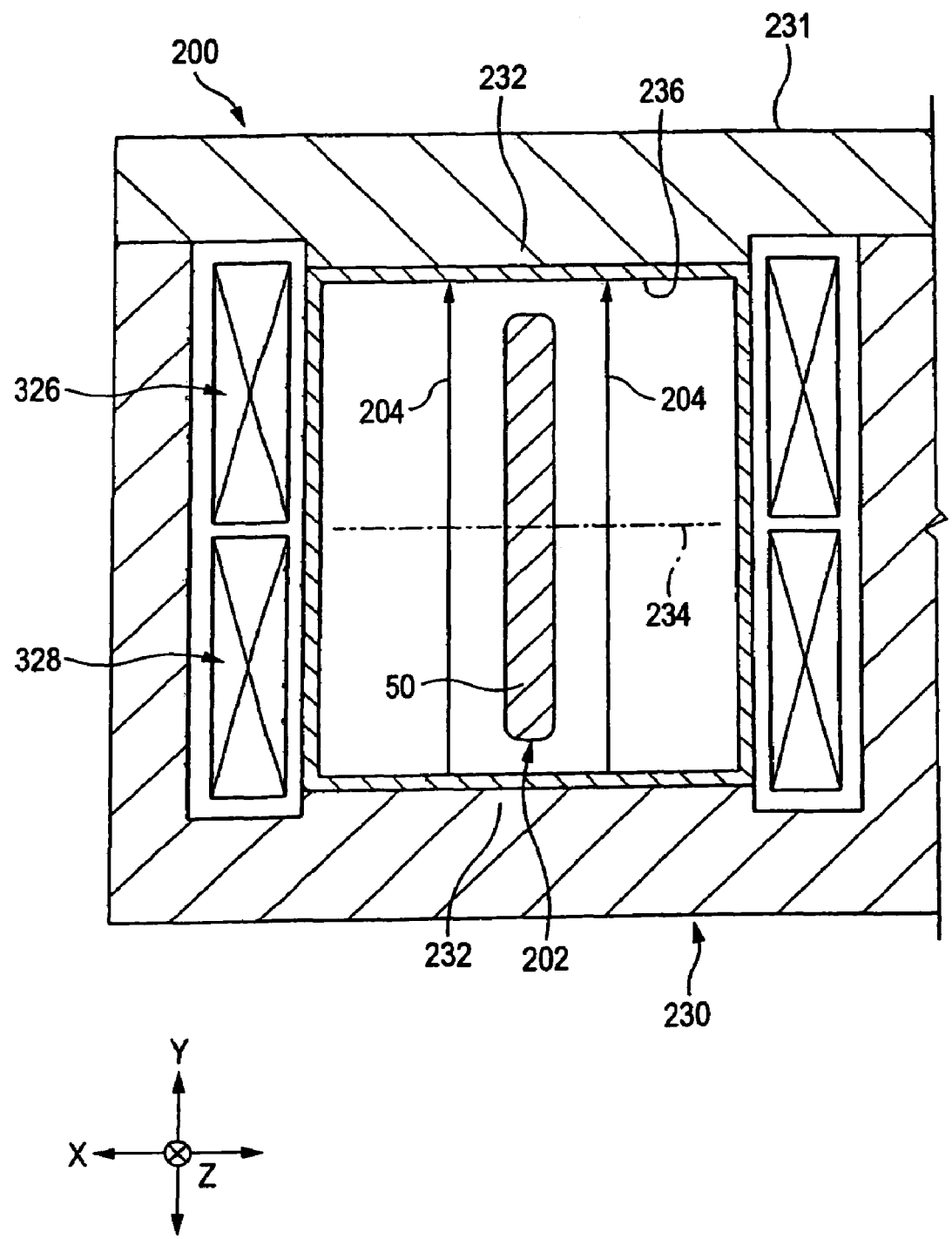
FIG. 40 is a section view showing a further example of the analyzing electromagnet and corresponding to FIG. 20.
Figure 41:
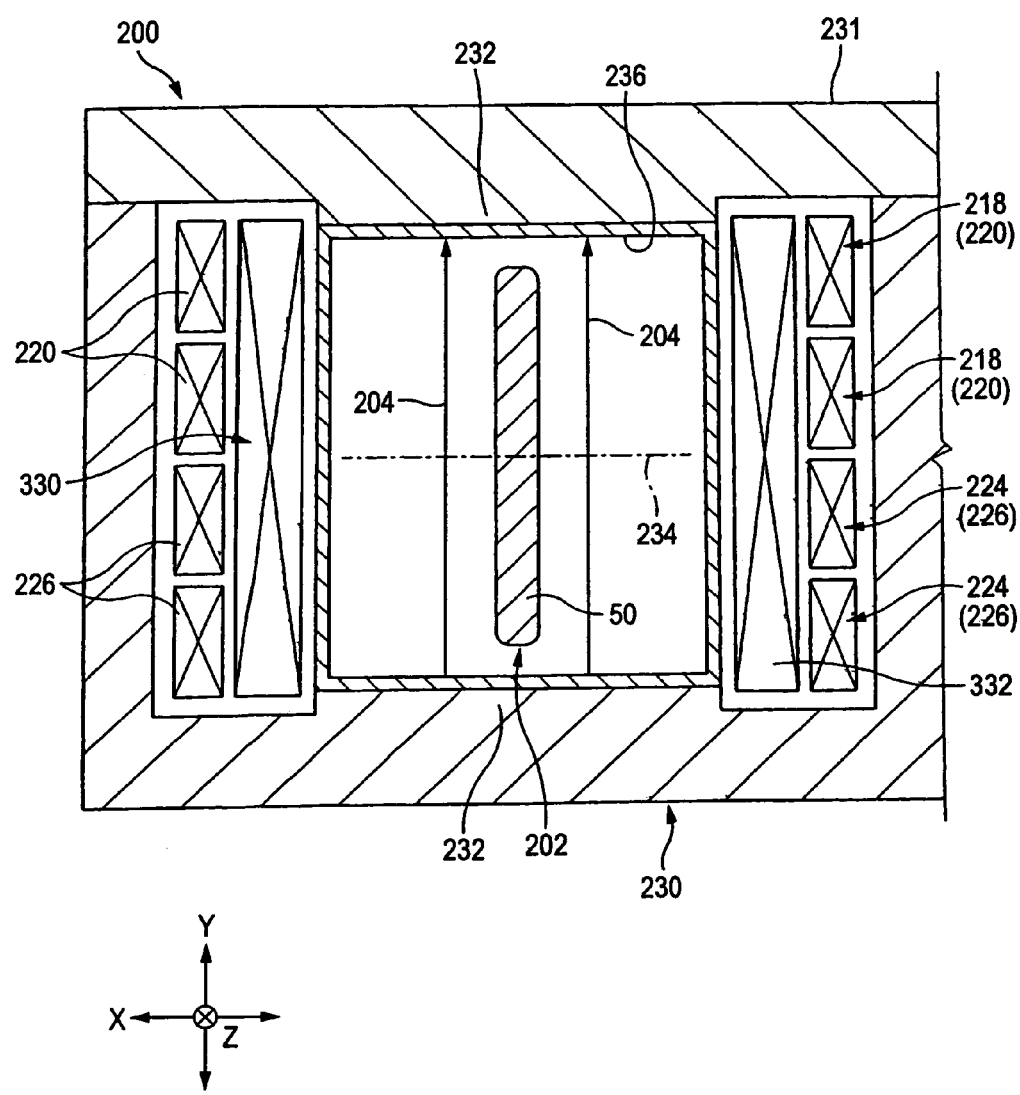
FIG. 41 is a section view showing a still further example of the analyzing electromagnet and corresponding to FIG. 20.

The analyzing electromagnet 200 shown in FIG. 40 comprises the first and second coils 326, 328 that cooperate with each other to generate a magnetic field which bends the ion beam 50 in the X direction. The coils 326, 328 are structured in a similar manner as the first and second inner coils 206, 212 (see FIG. 23), respectively. Therefore, also the first and second coils 326, 328 can be produced by the same production method as described above.

Also in the analyzing electromagnet 200 of the example, the first and second coils 326, 328 are structured in a similar manner as the first and second inner coils 206, 212. Because of the same reason as described above, therefore, the projection distance of the connecting portions of the coils from the yoke 230 is reduced, thereby attaining effects such as that the analyzing electromagnet 200 can be miniaturized, and that the power consumption can be reduced.

Since the analyzing electromagnet comprises the first and second coils 326, 328, it is possible to easily cope with the ion beam 50 having the large Y-direction dimension $W_Y$.

The analyzing electromagnet 200 shown in FIG. 26 comprises: the inner coil 330 that is structured in a similar as the coil 320, and that generates a main magnetic field which bends the ion beam 50 in the X direction; and the first and second outer coils 218, 224 that are configured as described above, that are outside the inner coil 330, and that generate a sub-magnetic field which assists or corrects the main magnetic field. Namely, in place of the first and second inner coils 206, 212 shown in FIG. 20 and the like, the analyzing electromagnet comprises the inner coil 330. Therefore, also the inner coil 330 and the first and second outer coils 218, 224 can be produced by the same production method as described above.

Feature items in the case where these coils are produced will be described. With using the stacked coil 290 (see FIG. 29) in which the axial dimension (height) is set to a desired one, notched portions which are similar to the notched portions 276 to 281 of FIG. 37 are disposed in the inner and outer coils 292, 294 by a cutting process or the like. In the outer coil 294, a gap which is similar to the gap 248 shown in FIG. 22 is disposed by a cutting process or the like, thereby forming the first and second outer coils 218, 224. In a similar manner as the case of FIG. 22, each of the first and second outer coils 218, 224 is configured by plural coils.

In the example shown in FIG. 26, the number of the first outer coils 218 is two. However, the number is not restricted to this. The number is an arbitral number of one or more. The second outer coils 224 are configured in a similar manner.

Also the analyzing electromagnet 200 of the example comprises the inner coil 330 and first and second outer coils 218, 224 which are configured as described above. Because of the same reason as described above, therefore, the projection distance of the connecting portions of the coils from the yoke 230 is reduced, thereby attaining effects such as that the analyzing electromagnet 200 can be miniaturized, and that the power consumption can be reduced.

The analyzing electromagnet comprises the first and second outer coils 218, 224 which are configured as described above, in addition to the inner coil 330. Therefore, a magnetic field in which the homogenization of the magnetic flux density distribution in the Y direction is high can be generated in the beam path 202 of the ion beam 50. As a result, the disturbance of the form of the ion beam 50 at the emission can be suppressed to a lower level. This effect is more remarkable in the case where the Y-direction dimension $W_Y$ of the object ion beam 50 is large.

Because the plural first outer coils 218 and the plural second outer coils 224 are disposed, the magnetic flux density distribution in the Y direction of the magnetic field generated in the beam path 202 can be corrected more finely by theses outer coils 218, 224. Therefore, it is possible to generate a magnetic field in which the homogenization in the Y direction is higher. As a result, the disturbance of the form of the ion beam 50 at the emission can be suppressed to a lower level.

Also in the case where the ion implanter shown in FIG. 1 comprises the analyzing electromagnet 200 of each of the examples, in accordance with the miniaturization of the analyzing electromagnet 200, the whole ion implanter can be miniaturized, and therefore the area required for installing the ion implanter can be reduced. Also the weight of the analyzing electromagnet can be reduced. Moreover, in accordance with the reduction of the power consumption of the analyzing electromagnet 200, the power consumption of the whole ion implanter can be reduced.

(4) About Accelerating/Decelerating Device 400

The accelerating/decelerating device 400 shown in FIG. 1 deflects the ion beam 50 passed through the analysis slit 70, in the X direction by means of an electrostatic field, and accelerates or decelerates the ion beam 50 by means of the electrostatic field. Preferably, the accelerating/decelerating device 400 is disposed on the downstream side as far as possible in order that an effect of suppressing energy contamination which will be described later is effectively exerted. In the example shown in FIG. 1, the device is disposed between the analysis slit 70 and the implanting position, i.e., between the analysis slit 70 and the substrate driving device 500.

When the accelerating/decelerating device 400 is provided, the accelerating/decelerating device 400 can perform not only acceleration/deceleration of the ion beam 50, but also deflection of the ion beam 50 in the X direction. Therefore, the ion beam 50 of a desired energy can be selectively derived, and energy contamination (mixture of unwanted energy ions) can be suppressed. Moreover, these can be realized by the single accelerating/decelerating device 400. As compared with the case where an energy analyzer is separately disposed, therefore, the transportation path of the ion beam 50 can be shortened. Accordingly, the transport efficiency of the ion beam 50 can be improved. In the case where the ion beam 50 has a low energy and a large current, particularly, the ion beam 50 during transportation is easily diverged by the space charge effect. Therefore, the effect of shortening the transportation distance is remarkable.

Figure 42:
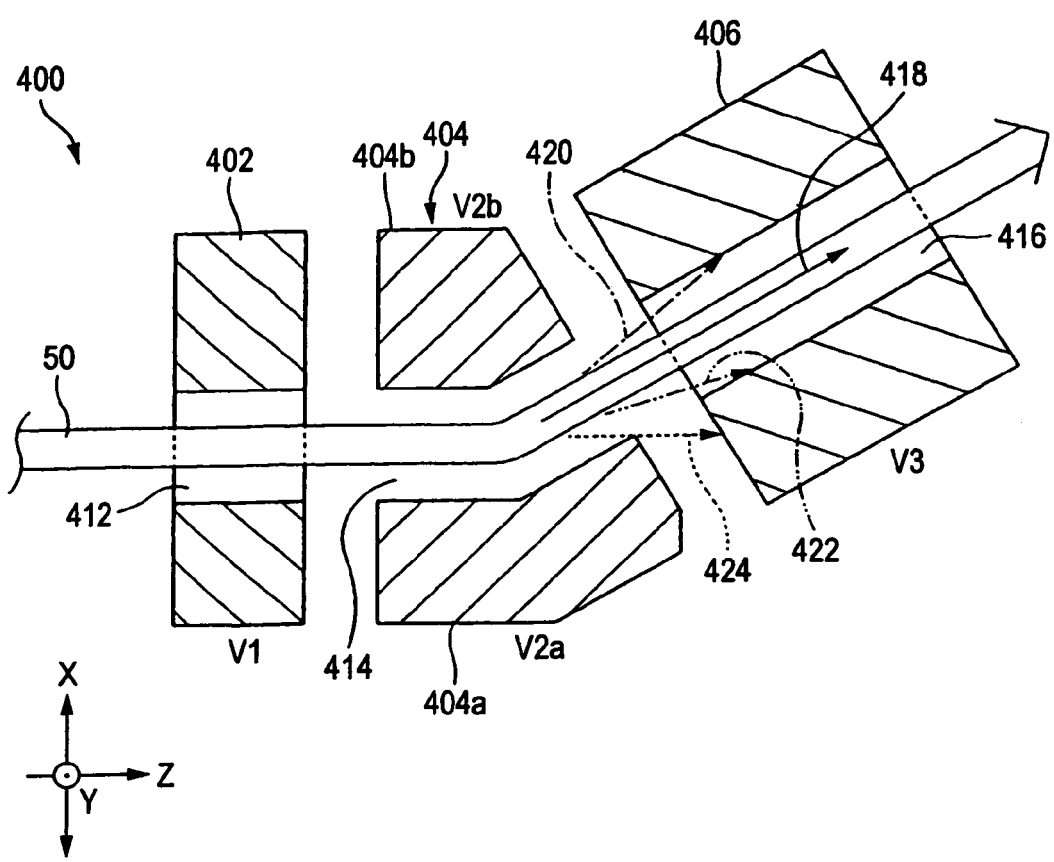
FIG. 42 is a cross section view showing an example of an accelerating/decelerating device shown in FIG. 1.

FIG. 42 shows a more specific example of the accelerating/decelerating device 400. The accelerating/decelerating device 400 has first to third electrodes 402, 404, 406 which are arranged in the sequence of the first electrode 402, the second electrode 404, and the third electrode 406 in the ion beam traveling direction with starting from the upstream side. In the example, each electrode has openings 412, 416 which extend in the Y direction, and through which the ion beam 50 flows. In the example, the electrode 402 is configured by one electrode. Alternatively, the electrode may be configured by two electrodes between which the path of the ion beam 50 is interposed in the X direction, and which are at the same potential. The same is applicable also to the electrode 406. The electrode 404 has a gap 414 which extends in the Y direction, and through which the ion beam 50 flows.

A potential V1 with respect to the ground potential is applied to the first electrode 402. Usually, the potential V1 is a positive (acceleration mode) or negative (deceleration mode) high potential.

In the case where potentials are applied to the electrodes 402, 404, 406 or electrode members 404a, 404b which will be described later, when the potentials are other than 0 V, the potentials are supplied from voltage applying means (for example, DC power sources, voltage dividing resistors for dividing a voltage from a DC power source, or the like which are not shown, the same shall apply hereinafter) corresponding to the electrodes. When the potentials are 0 V, the corresponding electrodes are grounded.

Usually, the second electrode 404 is set to a potential which is at the level between the first and third electrodes 402, 406. In the case of a well-known electrostatic accelerating tube, the second electrode 404 is configured by a single electrode. In this example, the second electrode is dividedly configured by the two electrode members 404a, 404b which are opposed to each other in the X direction across the path of the ion beam 50. Furthermore, potentials V2a, V2b (V2a # V2b) which are different from each other are applied to the electrode members 404a, 404b, respectively, so that the ion beam 50 is deflected in the X direction. Specifically, to the electrode member 404b that is on the side in which the ion beam 50 is to be deflected, the potential V2b which is lower than the potential V2a of the counter electrode 404a is applied, or V2b<V2a is set. Means for applying such potentials are as described above.

The gap 414 through which the ion beam 50 flows is disposed between the two electrode members 404a, 404b constituting the electrode 404. Preferably, the gap 414 is bent in the deflection direction of the ion beam 50 as in this example. Specifically, the gap is preferably bent along the orbit of ions 418 having a specific energy after deflection, or specifically a desired energy. According to the configuration, the ion beam 50 consisting of the ions 418 having the desired energy can be efficiently derived.

A potential V3 which is usually 0 V is applied to the third electrode 406. Namely, the third electrode is grounded.

Preferably, the third electrode 406 which is on the downstream side of the second electrode 404 is placed along the orbit of the ions 418 having the specific energy after deflection by the electrode 404, or specifically the desired energy. According to the configuration, the ions 418 having the desired energy can be efficiently derived, and ions 420, 422 having an energy other than the energy, and neutral particles 424 can be efficiently blocked by the electrode 406. Therefore, energy contamination can be suppressed more effectively.

The difference between the potentials V2a, V2b which are applied to the electrode members 404a, 404b constituting the electrode 404 is set so that the ions 418 having the desired (objective) energy pass through the center orbit of the accelerating/decelerating device 400, specifically the center orbits of the electrodes 404, 406 (more specifically, the gap 414 and the opening 416) including and subsequent to the second electrode 404 having the deflecting function.

Table 1 collectively shows examples of the electrodes and the potentials applied to the electrodes. Examples 1 and 2 are those in the acceleration mode in which the ion beam 50 is accelerated by the accelerating/decelerating device 400, and Example 3 is that in the deceleration mode in which the ion beam 50 is decelerated. In the case of Example 1, an accelerating energy of 30 keV can be realized, and, in the case of Example 2, an accelerating energy of 130 keV can be realized. In the case of Example 3, an accelerating energy of 8 keV can be realized. In any case, the potential V2b of the electrode member 404b which is one electrode constituting the second electrode 404 is set to be lower than the potential V2a of the counter electrode 404a.

TABLE 1

| | Potential V1 [kV] | Potential V2a [kV] | Potential V2b [kV] | Potential V3 [kV] |
|---|---|---|---|---|
| Example 1 | 30 | 0 | −48 | 0 |
| Example 2 | 130 | 100 | 52 | 0 |
| Example 3 | −8 | 0 | −1 | 0 |

According to the accelerating/decelerating device 400, the ion beam 50 can be deflected by the second electrode 404 which is configured by the two electrode members 404a, 404b, and to which the different potentials V2a, V2b are applied. At this time, the deflection amount depends on the energy of the ion beam 50 in the deflection, and hence the ions 418 having the desired energy can be separated from the ions 420, 422 having other energies. The ions 420 are ions having an energy which is lower than the desired energy, and their deflection amount is larger than that of the ions 418. The ions 422 are ions having an energy which is higher than the desired energy, and their deflection amount is smaller than that of the ions 418. The neutral particles 424 straight advance without being deflected, and hence can be separated. Namely, the accelerating/decelerating device 400 exerts the energy separating function, and hence the ion beam 50 consisting of the ions 418 having the desired energy can be selectively derived, and energy contamination can be suppressed. In the example, the ions 420, 422 other than the ions 418 having the desired energy, and the neutral particles 424 impinge on the electrode 406 which is on the downstream side of the second electrode 404, whereby they are blocked and removed away.

Moreover, the accelerating/decelerating device 400 exerts also the original function of accelerating or decelerating the ion beam 50, in addition to the above-described energy separating function. These functions can be realized by the single accelerating/decelerating device 400, and hence it is not necessary to separately dispose an energy separator. As compared with the case where an energy separator is separately disposed, therefore, the transportation path of the ion beam 50 can be shortened. Accordingly, the transport efficiency of the ion beam 50 can be improved.

Furthermore, the ion beam 50 can be accelerated in two stages, i.e., between the electrodes 402 and 404, and between the electrodes 404 and 406. Example 2 in Table 1 shows an example of such a case. Before the acceleration in the subsequent stage (i.e., during a period when the energy is low), the ion beam 50 can be deflected by the electrode 404. As compared with the case where deflection is performed after full acceleration, the ion beam 50 can be easily deflected. Specifically, the difference between the potentials V2a and V2b applied on the two electrode members 404a, 404b constituting the electrode 404 can be made small. Consequently, there are advantages such as that electrical insulation in the vicinity of the electrode 404 is facilitated.

Ions and neutral particles other than the ions 418 having the desired energy can be blocked and removed away by the electrode 406 which is on the downstream side of the electrode 404. Therefore, energy contamination can be suppressed more effectively. Particularly, it is empirically known that, in the deceleration mode (see Example 3 in Table 1), the neutral particles 424 are easily generated by charge conversion in deceleration of the ion beam 50 between the electrodes 402 and 404. Even when many neutral particles 424 are generated, however, they straightly travel and impinge on the electrode 406 to be blocked. Therefore, the neutral particles 424 can be effectively eliminated in the accelerating/decelerating device 400.

In the acceleration mode, usually, electrons are emitted and accelerated to a higher potential side from a place of an electrode on which ions of an energy other than a desired energy impinge, and an X-ray having a high energy corresponding to such accelerated electrons is generated from a portion of an electrode on which the accelerated electrons impinge. A well-known electrostatic accelerating tube does not have the deflecting function. Therefore, the accelerated electrons can reach a higher potential electrode (an electrode corresponding to the electrode 404) without being bent, and are accelerated by a large energy corresponding to the potential of the higher potential electrode to impinge the higher potential electrode, so that an X-ray having a high energy is generated therefrom.

By contrast, as in the accelerating/decelerating device 400, the second electrode 404 is configured by the two electrode members 404a, 404b, and different potentials are applied to the electrode members, thereby providing the electrode with the deflecting function. According to the configuration, electrons emitted from a place on which ions of an unwanted energy impinge are bent by the electrode 404 so as to be disabled to reach the electrode 402 of the higher potential. Specifically, the electrons are bent toward the electrode member 404a which has a higher potential among the two electrode members 404a, 404b constituting the electrode 404, and then impinges on the electrode member 404a. At this time, the acceleration energy of the electrons is an energy corresponding to the potential of the electrode member 404a, and lower than that in the case where the electrons impinge on the electrode 402 of the higher potential. In the case of Example 1 in Table 1, for example, the energy of impinging electrons is approximately 0 eV, and an X-ray is not substantially generated. In the case of Example 2, the energy is about 100 keV, and is lower than about 130 keV in the case where the electron impinge on the electrode 402. In any case, therefore, the energy of a generated X-ray can be made lower than that in a well-known electrostatic accelerating tube.

As required, another electrode may be further disposed on the upstream side of the electrode 402 or the downstream side of the electrode 406. For example, a high-potential electrode for accelerating or decelerating the ion beam 50 may be disposed on the upstream side of the electrode 402. A negative-potential electrode for suppressing reversed electrons may be disposed on the downstream side of the electrode 406.

What is claimed is:

1. An ion implanter in which a traveling direction of an ion beam is set as a Z direction, two directions which are substantially orthogonal to each other in a plane that is substantially orthogonal to the Z direction are set as X and Y directions, respectively, and a ribbon-like ion beam in which a dimension in the Y direction is larger than a dimension in the X direction is transported to irradiate a substrate, thereby performing ion implantation, said ion implanter comprising:

an ion source that has one or more filaments for generating an arc discharge in a plasma vessel into which a gas is introduced, and that generates the ribbon-like ion beam in which a Y-direction dimension is larger than a Y-direction dimension of the substrate;

a substrate driving device which, in an implanting position where the ion beam is caused to be incident on the substrate, moves the substrate in a direction intersecting with a principal face of the ion beam;

one or more electron beam sources which generate an electron beam, which emit the electron beam into said plasma vessel of said ion source to ionize the gas, thereby producing a plasma, and which scans the electron beam in the Y direction in said plasma vessel;

one or more electron-beam power sources which supply an extraction voltage for controlling a generation quantity of the electron beam, and a scan voltage for the scan to said electron beam sources;

an ion beam monitor which, in the implanting position or a vicinity of the position, measures a Y-direction ion beam current density distribution of the ion beam at plural monitor points in the Y direction; and a controlling device having a function of homogenizing the Y-direction ion beam current density distribution measured by said ion beam monitor, by, while controlling said electron-beam power sources on the basis of measurement data of said ion beam monitor to maintain the quantity of the electron beam generated from said electron beam sources to a substantially constant value, performing at least one of: a relative increase of a scanning speed of the electron beam in a position in said ion source corresponding to a monitor point where an ion beam current density measured by said ion beam monitor is relatively large; and a relative decrease of the scanning speed of the electron beam in a position in said ion source corresponding to a monitor point where the ion beam current density measured by said ion beam monitor is relatively small.

2. An ion implanter according to claim 1, wherein
(a) both numbers of said electron beam sources and said electron-beam power sources are one,
(b) said controlling device has functions of:
supplying a scan signal which is an original of the scan voltage to be supplied from said electron-beam power source to said electron beam source, to said electron-beam power source;
calculating an average value of ion beam current densities in a Y-direction distribution measured by said ion beam monitor;
uniformly controlling filament currents to be flown through said filaments of said ion source so that the calculate average value is substantially equal to a preset predetermined ion beam current density;
calculating an error of the Y-direction distribution which is a difference between the ion beam current density in a Y-direction distribution measured by said ion beam monitor, and the preset ion beam current density;
determining a monitor point where the calculated error is larger than a predetermined allowable error, and a sign of an error at the monitor point;
determining a scan voltage corresponding to the determined monitor point;
based on the determined sign of the error, increasing the scanning speed of the electron beam at a scan voltage corresponding to a monitor point where the measured ion beam current density is larger, in proportion to a degree of the error, and decreasing the scanning speed of the electron beam at a scan voltage corresponding to a monitor point where the measured ion beam current density is smaller, in proportion to a degree of the error, thereby shaping a waveform of the scan signal so that the error is equal to or less than the allowable error at substantially all monitor points on which the ion beam impinges; and
storing data of the shaped scan signal, and data of the filament currents, and
(c) said electron-beam power source has an amplifier which amplifies the scan signal supplied from said controlling device, to produce the scan voltage.

3. An ion implanter according to claim 1, wherein
(a) both numbers of said electron beam sources and said electron-beam power sources are plural,
(b) said controlling device has functions of:
supplying a scan signal which is an original of the scan voltage to be supplied from said electron-beam power sources to said electron beam sources, to said electron-beam power sources;
calculating an average value of ion beam current densities in a Y-direction distribution measured by said ion beam monitor;
uniformly controlling filament currents to be flown through said filaments of said ion source so that the calculate average value is substantially equal to a preset predetermined ion beam current density;
calculating an error of the Y-direction distribution which is a difference between the ion beam current density in a Y-direction distribution measured by said ion beam monitor, and the preset ion beam current density;
determining a monitor point where the calculated error is larger than a predetermined allowable error, and a sign of an error at the monitor point;
determining the electron beam source corresponding to the determined monitor point, and the scan voltage;
based on the determined sign of the error, increasing the scanning speed of the electron beam at a scan voltage corresponding to a monitor point where the measured ion beam current density is larger, in proportion to a degree of the error, and decreasing the scanning speed of the electron beam at a scan voltage corresponding to a monitor point where the measured ion beam current density is smaller, in proportion to a degree of the error, thereby shaping a waveform of the scan signal so that the error is equal to or less than the allowable error at substantially all monitor points on which the ion beam impinges; and
storing data of the shaped scan signal, and data of the filament currents, and
(c) each of said electron-beam power sources has an amplifier which amplifies the scan signal supplied from said controlling device, to produce the scan voltage.

4. An ion implanter in which a traveling direction of an ion beam is set as a Z direction, two directions which are substantially orthogonal to each other in a plane that is substantially orthogonal to the Z direction are set as X and Y directions, respectively, and a ribbon-like ion beam in which a dimension in the Y direction is larger than a dimension in the X direction is transported to irradiate a substrate, thereby performing ion implantation, said ion implanter comprising:
an ion source that has one or more filaments for generating an arc discharge in a plasma vessel into which a gas is introduced, and that generates the ribbon-like ion beam in which a Y-direction dimension is larger than a Y-direction dimension of the substrate;
a substrate driving device which, in an implanting position where the ion beam is caused to be incident on the substrate, moves the substrate in a direction intersecting with a principal face of the ion beam;

one or more electron beam sources which generate an electron beam, and emit the electron beam into said plasma vessel of said ion source to ionize the gas, thereby producing a plasma, and which scans the electron beam in the Y direction in said plasma vessel;

one or more electron-beam power sources which supply an extraction voltage for controlling a generation quantity of the electron beam, and a scan voltage for the scan to said electron beam sources;

an ion beam monitor which, in the implanting position or a vicinity of the position, measures a Y-direction ion beam current density distribution of the ion beam at plural monitor points in the Y direction; and a controlling device having a function of homogenizing the Y-direction ion beam current density distribution measured by said ion beam monitor, by, while controlling said electron-beam power sources on the basis of measurement data of said ion beam monitor to maintain a scanning speed of the electron beam generated by said electron beam source to a substantially constant value, performing at least one of: a relative decrease of the generation quantity of the electron beam in a position in said ion source corresponding to a monitor point where an ion beam current density measured by said ion beam monitor is relatively large; and a relative increase of the generation quantity of the electron beam in a position in said ion source corresponding to a monitor point where the ion beam current density measured by said ion beam monitor is relatively small.

5. An ion implanter according to claim 4, wherein
(a) both numbers of said electron beam sources and said electron-beam power sources are one,
(b) said controlling device has functions of:
supplying an extraction signal which is an original of the extraction voltage to be supplied from said electron-beam power source to said electron beam source, to said electron-beam power source;
calculating an average value of ion beam current densities in a Y-direction distribution measured by said ion beam monitor;
uniformly controlling filament currents to be flown through said filaments of said ion source so that the calculate average value is substantially equal to a preset predetermined ion beam current density;
calculating an error of the Y-direction distribution which is a difference between the ion beam current density in a Y-direction distribution measured by said ion beam monitor, and the preset ion beam current density;
determining a monitor point where the calculated error is larger than a predetermined allowable error, and a sign of an error at the monitor point;
determining a scan voltage corresponding to the determined monitor point;
based on the determined sign of the error, decreasing the extraction voltage at a scan voltage corresponding to a monitor point where the measured ion beam current density is larger, in proportion to a degree of the error, and increasing the extraction voltage at a scan voltage corresponding to a monitor point where the measured ion beam current density is smaller, in proportion to a degree of the error, thereby shaping a waveform of the extraction signal so that the error is equal to or less than the allowable error at substantially all monitor points on which the ion beam impinges; and
storing data of the shaped extraction signal, and data of the filament currents, and
(c) said electron-beam power source has an amplifier which amplifies the extraction signal supplied from said controlling device, to produce the extraction voltage.

6. An ion implanter according to claim 4, wherein
(a) both numbers of said electron beam sources and said electron-beam power sources are plural,
(b) said controlling device has functions of:
supplying an extraction signal which is an original of the extraction voltage to be supplied from said electron-beam power sources to said electron beam sources, to said electron-beam power sources;
calculating an average value of ion beam current densities in a Y-direction distribution measured by said ion beam monitor;
uniformly controlling filament currents to be flown through said filaments of said ion source so that the calculate average value is substantially equal to a preset predetermined ion beam current density;
calculating an error of the Y-direction distribution which is a difference between the ion beam current density in a Y-direction distribution measured by said ion beam monitor, and the preset ion beam current density;
determining a monitor point where the calculated error is larger than a predetermined allowable error, and a sign of an error at the monitor point;
determining the electron beam source corresponding to the determined monitor point, and the scan voltage;
based on the determined sign of the error, decreasing the extraction voltage at a scan voltage corresponding to a monitor point where the measured ion beam current density is larger, in proportion to a degree of the error, and increasing the extraction voltage at a scan voltage corresponding to a monitor point where the measured ion beam current density is smaller, in proportion to a degree of the error, thereby shaping a waveform of the extraction signal so that the error is equal to or less than the allowable error at substantially all monitor points on which the ion beam impinges; and
storing data of the shaped extraction signal, and data of the filament currents, and
(c) each of said electron-beam power sources has an amplifier which amplifies the extraction signal supplied from said controlling device, to produce the extraction voltage.

7. An ion implanter according to claim 1 or 4, further comprising:
an accelerating/decelerating device which is disposed between an analyzing electromagnet that bends the ion beam from said ion source in the X direction to analyze a momentum, and the implanting position, which bends the ion beam in the X direction by means of an electrostatic field, and which accelerates or decelerates the ion beam,
said accelerating/decelerating device having first to third electrodes which are arranged in a sequence of said first electrode, said second electrode, and said third electrode in the ion beam traveling direction with starting from an upstream side, and accelerating or decelerating the ion beam in two stages between said first and second electrodes, and said second and third electrodes,
said second electrode being configured by two electrode members which are opposed to each other in the X direction across the path of the ion beam, and to which different potentials are applied to deflect the ion beam in the X direction, said third electrode being disposed along an orbit of an ion beam having a specific energy after the deflection.

8. An ion implanter according to claim 1 or 4, further comprising:

an analyzing electromagnet which is disposed between said ion source and the implanting position, and which bends the ion beam from said ion source in the X direction to analyze a momentum, said analyzing electromagnet comprising:

a coil having: one set of body portions that are opposed to each other in the X direction across a beam path through which the ion beam passes; and at least one set of connecting portions that connect end portions of said body portions in the Z direction with each other, while avoiding said beam path, said coil generating a magnetic field which bends the ion beam in the X direction; and a yoke which collectively surrounds outer sides of said body portions of said coil, said coil having a configuration in which a notched portion is disposed in a fan-shaped cylindrical stacked coil while leaving said body portions and said connecting portions, said stacked coil being configured by: stacking laminations of an insulation sheet and conductor sheet in which a principal face extends along the Y direction, on an outer peripheral face of a laminated insulator, while winding the laminations in multiple turns; and forming a laminated insulator on an outer peripheral face of the stack.

9. An ion implanter according to claim 1 or 4, further comprising:

an analyzing electromagnet which is disposed between said ion source and the implanting position, and which bends the ion beam from said ion source in the X direction to analyze a momentum, said analyzing electromagnet comprising:

a first coil which is a saddle-shaped coil having: one set of body portions that are opposed to each other in the X direction across a beam path through which the ion beam passes, and that cover about a half or more of one side of the ion beam in the Y direction; and one set of connecting portions that connect end portions of said body portions in the Z direction with each other, while avoiding said beam path, said first coil cooperating with a second coil to generate a magnetic field which bends the ion beam in the X direction;

said second coil which is a saddle-shaped coil having: one set of body portions that are opposed to each other in the X direction across the beam path, and that cover about a half or more of another side of the ion beam in the Y direction; and one set of connecting portions that connect end portions of said body portions in the Z direction with each other, while avoiding said beam path, said second coil being disposed overlappingly with said first coil in the Y direction, and cooperating with said first coil to generate a magnetic field which bends the ion beam in the X direction; and a yoke which collectively surrounds outer sides of said body portions of said first and second coils, each of said first and second coils having a configuration in which a notched portion is disposed in a fan-shaped cylindrical stacked coil while leaving said body portions and said connecting portions, said stacked coil being configured by: stacking laminations of an insulation sheet and conductor sheet in which a principal face extends along the Y direction, on an outer peripheral face of a laminated insulator, while winding the laminations in multiple turns; and forming a laminated insulator on an outer peripheral face of the stack.

10. An ion implanter according to claim 1 or 4, further comprising:

an analyzing electromagnet which is disposed between said ion source and the implanting position, and which bends the ion beam from said ion source in the X direction to analyze a momentum, said analyzing electromagnet comprising:

an inner coil having: one set of body portions that are opposed to each other in the X direction across a beam path through which the ion beam passes; and a connecting portion which connects end portions of said body portions in the Z direction with each other, while avoiding said beam path, said inner coil generating a main magnetic field which bends the ion beam in the X direction;

one or more first outer coils which are saddle-shaped coils having: one set of body portions that are outside said inner coil, and that are opposed to each other in the X direction across the beam path; and one set of connecting portions that connect end portions of said body portions in the Z direction with each other, while avoiding said beam path, said first outer coils generating a sub-magnetic field which assists or corrects the main magnetic field;

one or more second outer coils which are saddle-shaped coils having: one set of body portions that are outside said inner coil, and that are opposed to each other in the X direction across the beam path; and one set of connecting portions that connect end portions of said body portions in the Z direction with each other, while avoiding said beam path, said second outer coils being disposed overlappingly with said first outer coils in the Y direction, and generating a sub-magnetic field which assists or corrects the main magnetic field; and a yoke which collectively surrounds outer sides of said body portions of said inner coil, and said first and second outer coils, each of said inner coil, and said first and second outer coils having a configuration in which a notched portion is disposed in a fan-shaped cylindrical stacked coil while leaving said body portions and said connecting portions, said stacked coil being configured by: stacking laminations of an insulation sheet and conductor sheet in which a principal face extends along the Y direction, on an outer peripheral face of a laminated insulator, while winding the laminations in multiple turns; forming a laminated insulator on an outer peripheral face of the stack; stacking laminations of an insulation sheet and conductor sheet in which a principal face extends along the Y direction, on an outer peripheral face of the stack, while winding the laminations in multiple turns; and forming a laminated insulator on an outer peripheral face of the stack.

11. An ion implanter according to claim 1 or 4, further comprising:

an analyzing electromagnet which is disposed between said ion source and the implanting position, and which bends the ion beam from said ion source in the X direction to analyze a momentum, said analyzing electromagnet comprising:

a first inner coil which is a saddle-shaped coil having: one set of body portions that are opposed to each other in the X direction across a beam path through which the ion beam passes, and that cover about a half or more of one side of the ion beam in the Y direction; and one set of connecting portions that connect end portions of said body portions in the Z direction with each other, while avoiding said beam path, said first coil cooperating with a second inner coil to generate a main magnetic field which bends the ion beam in the X direction;

said second inner coil which is a saddle-shaped coil having: one set of body portions that are opposed to each other in the X direction across the beam path, and that cover about a half or more of another side of the ion beam in the Y direction; and one set of connecting portions that connect end portions of said body portions in the Z direction with each other, while avoiding said beam path, said second inner coil being disposed overlappingly with said first inner coil in the Y direction, and cooperating with said first inner coil to generate the main magnetic field which bends the ion beam in the X direction;

one or more first outer coils which are saddle-shaped coils having: one set of body portions that are outside said first inner coil, and that are opposed to each other in the X direction across the beam path; and one set of connecting portions that connect end portions of said body portions in the Z direction with each other, while avoiding said beam path, said first outer coils generating a sub-magnetic field which assists or corrects the main magnetic field;

one or more second outer coils which are saddle-shaped coils having: one set of body portions that are outside said second inner coil, and that are opposed to each other in the X direction across the beam path; and one set of connecting portions that connect end portions of said body portions in the Z direction with each other, while avoiding said beam path, said second outer coils being disposed overlappingly with said first outer coils in the Y direction, and generating a sub-magnetic field which assists or corrects the main magnetic field; and a yoke which collectively surrounds outer sides of said body portions of said first and second inner coils, and said first and second outer coils, each of said first inner coil and said first outer coil having a configuration in which a notched portion is disposed in a fan-shaped cylindrical stacked coil while leaving said body portions and said connecting portions, said stacked coil being configured by: stacking laminations of an insulation sheet and conductor sheet in which a principal face extends along the Y direction, on an outer peripheral face of a laminated insulator, while winding the laminations in multiple turns; forming a laminated insulator on an outer peripheral face of the stack; stacking laminations of an insulation sheet and conductor sheet in which a principal face extends along the Y direction, on an outer peripheral face of the stack, while winding the laminations in multiple turns; and forming a laminated insulator on an outer peripheral face of the stack, and each of said second inner coil and said second outer coil having a configuration in which a notched portion is disposed in a fan-shaped cylindrical stacked coil while leaving said body portions and said connecting portions, said stacked coil being configured by: stacking laminations of an insulation sheet and conductor sheet in which a principal face extends along the Y direction, on an outer peripheral face of a laminated insulator, while winding the laminations in multiple turns; forming a laminated insulator on an outer peripheral face of the stack; stacking laminations of an insulation sheet and conductor sheet in which a principal face extends along the Y direction, on an outer peripheral face of the stack, while winding the laminations in multiple turns; and forming a laminated insulator on an outer peripheral face of the stack.

12. An ion implanter according to claim 8, wherein said analyzing electromagnet further comprises one set of magnet poles which are inwardly projected from said yoke so as to be opposed to each other in the Y direction across the beam path.

13. An ion implanter according to claim 9, wherein said analyzing electromagnet further comprises one set of magnet poles which are inwardly projected from said yoke so as to be opposed to each other in the Y direction across the beam path.

14. An ion implanter according to claim 10, wherein said analyzing electromagnet further comprises one set of magnet poles which are inwardly projected from said yoke so as to be opposed to each other in the Y direction across the beam path.

15. An ion implanter according to claim 11, wherein said analyzing electromagnet further comprises one set of magnet poles which are inwardly projected from said yoke so as to be opposed to each other in the Y direction across the beam path.

* * * * *